(12) United States Patent
Gillett et al.

(10) Patent No.: US 10,413,658 B2
(45) Date of Patent: Sep. 17, 2019

(54) HELICAL INSERTION INFUSION DEVICE

(71) Applicant: Capillary Biomedical, Inc., Irvine, CA (US)

(72) Inventors: David S. Gillett, San Diego, CA (US); Andres Dandler, Newport Beach, CA (US); Mark C. Estes, Malibu, CA (US); Kenneth C. Hsu, Tustin, CA (US)

(73) Assignee: Capillary Biomedical, Inc., Irvine, CA (US)

(*) Notice: Subject to any disclaimer, the term of this patent is extended or adjusted under 35 U.S.C. 154(b) by 0 days.

(21) Appl. No.: 15/943,517

(22) Filed: Apr. 2, 2018

(65) Prior Publication Data
US 2018/0280608 A1    Oct. 4, 2018

Related U.S. Application Data

(60) Provisional application No. 62/480,190, filed on Mar. 31, 2017, provisional application No. 62/517,825, filed on Jun. 9, 2017.

(51) Int. Cl.
*A61M 5/32* (2006.01)
*A61M 5/142* (2006.01)
(Continued)

(52) U.S. Cl.
CPC ........ *A61M 5/14248* (2013.01); *A61M 5/158* (2013.01); *A61M 5/3287* (2013.01);
(Continued)

(58) Field of Classification Search
CPC .... A61M 5/14248; A61M 2005/14252; A61M 5/158; A61M 5/3287; A61M 2005/3289; A61M 2005/1585
See application file for complete search history.

(56) References Cited

U.S. PATENT DOCUMENTS

| | | |
|---|---|---|
| 4,498,843 A | 2/1985 | Schneider et al. |
| 4,703,756 A | 11/1987 | Gough et al. |

(Continued)

FOREIGN PATENT DOCUMENTS

| | | |
|---|---|---|
| EP | 2004241 B1 | 12/2008 |
| WO | WO1996/032981 A1 | 10/1996 |

(Continued)

OTHER PUBLICATIONS

Bryant, J., Fluid dynamics—Equation of continuity and Bernoulli's principle; 37 pages; retrieved from the internet at http://www.physics.usyd.edu.au/~jbryant/Fluids/Fluidslect4.pdf on Apr. 2, 2015.

(Continued)

*Primary Examiner* — Jason E Flick
*Assistant Examiner* — Courtney B Fredrickson
(74) *Attorney, Agent, or Firm* — Shay Glenn LLP

(57) ABSTRACT

A system for delivering fluid to a user transcutaneously includes a subcutaneous infusion cannula base assembly, a cannula inserter assembly and a fluid connection assembly. The subcutaneous infusion cannula base assembly is configured to be located on the user's skin. The cannula inserter assembly is coupled to the cannula base assembly and is configured to drive an infusion cannula through the user's skin in a nominally helical trajectory. The fluid connection assembly is configured to fluidically connect the cannula base assembly to a source of delivery fluid. Cannula and stylet assemblies configured for helical or non-helical insertion are also disclosed.

15 Claims, 51 Drawing Sheets

(51) Int. Cl.
*A61M 25/06* (2006.01)
*A61M 5/158* (2006.01)

(52) U.S. Cl.
CPC ... *A61M 25/06* (2013.01); *A61M 2005/14252* (2013.01); *A61M 2005/1585* (2013.01); *A61M 2005/1586* (2013.01)

(56) References Cited

U.S. PATENT DOCUMENTS

| | | | |
|---|---|---|---|
| 4,755,173 A * | 7/1988 | Konopka | A61M 25/0606 128/DIG. 26 |
| 4,777,953 A | 10/1988 | Ash et al. | |
| 4,952,207 A * | 8/1990 | Lemieux | A61M 5/158 604/164.08 |
| 5,002,054 A | 3/1991 | Ash et al. | |
| 5,176,662 A | 1/1993 | Bartholomew et al. | |
| 5,545,152 A * | 8/1996 | Funderburk | A61M 39/14 285/376 |
| 5,584,831 A | 12/1996 | McKay | |
| 5,704,926 A | 1/1998 | Sutton | |
| 5,848,996 A | 12/1998 | Eldor | |
| 5,869,774 A | 2/1999 | Backlund et al. | |
| 5,879,367 A | 3/1999 | Latterell et al. | |
| 5,899,891 A | 5/1999 | Racz | |
| 5,919,369 A | 7/1999 | Ash | |
| 5,925,018 A | 7/1999 | Ungerstedt | |
| 5,947,953 A | 9/1999 | Ash et al. | |
| 5,995,860 A | 11/1999 | Sun et al. | |
| 6,017,361 A | 1/2000 | Mikus et al. | |
| 6,030,358 A | 2/2000 | Odland | |
| 6,042,561 A | 3/2000 | Ash et al. | |
| 6,049,727 A | 4/2000 | Crothall | |
| 6,056,718 A | 5/2000 | Funderburk et al. | |
| 6,122,536 A | 9/2000 | Sun et al. | |
| 6,261,272 B1 | 7/2001 | Gross et al. | |
| 6,302,866 B1 | 10/2001 | Marggi | |
| 6,304,766 B1 | 10/2001 | Colvin, Jr. | |
| 6,471,689 B1 | 10/2002 | Joseph et al. | |
| 6,537,241 B1 | 3/2003 | Odland | |
| 6,572,586 B1 | 6/2003 | Wojcik | |
| 6,585,695 B1 | 7/2003 | Adair et al. | |
| 6,618,603 B2 | 9/2003 | Varalli et al. | |
| 6,702,857 B2 | 3/2004 | Brauker et al. | |
| 6,736,797 B1 | 5/2004 | Larsen et al. | |
| 6,749,589 B1 * | 6/2004 | Douglas | A61M 25/0097 604/162 |
| 6,770,030 B1 | 8/2004 | Schaupp et al. | |
| 6,800,451 B2 | 10/2004 | Daniloff et al. | |
| 6,805,683 B1 | 10/2004 | Johansson | |
| 6,855,136 B2 | 2/2005 | Dorros et al. | |
| 6,862,534 B2 | 3/2005 | Sterling et al. | |
| 6,929,618 B1 | 8/2005 | Johansson | |
| 6,940,590 B2 | 9/2005 | Colvin, Jr. et al. | |
| 6,989,891 B2 | 1/2006 | Braig et al. | |
| 7,009,180 B2 | 3/2006 | Sterling et al. | |
| 7,022,071 B2 | 4/2006 | Schaupp et al. | |
| 7,157,723 B2 | 1/2007 | Colvin, Jr. et al. | |
| 7,211,068 B2 | 5/2007 | Douglas | |
| 7,235,350 B2 | 6/2007 | Schulman et al. | |
| 7,248,912 B2 | 7/2007 | Gough et al. | |
| 7,255,687 B2 | 8/2007 | Huang et al. | |
| 7,309,325 B2 | 12/2007 | Muller et al. | |
| 7,336,984 B2 | 2/2008 | Gough et al. | |
| 7,364,592 B2 | 4/2008 | Carr-Brendel et al. | |
| 7,588,558 B2 | 9/2009 | Sage, Jr. et al. | |
| 7,593,108 B2 | 9/2009 | Sterling et al. | |
| 7,613,491 B2 | 11/2009 | Boock et al. | |
| 7,621,395 B2 | 11/2009 | Mogensen et al. | |
| 7,637,918 B2 | 12/2009 | Dant | |
| 7,666,172 B2 | 2/2010 | Atil | |
| 7,699,808 B2 | 4/2010 | Marrs et al. | |
| 7,722,537 B2 | 5/2010 | Sterling et al. | |
| 7,744,570 B2 | 6/2010 | Fangrow, Jr. | |
| 7,800,078 B2 | 9/2010 | Colvin, Jr. et al. | |
| 7,822,450 B2 | 10/2010 | Colvin, Jr. et al. | |
| 7,871,456 B2 | 1/2011 | Gough et al. | |
| 7,894,870 B1 | 2/2011 | Lucisano et al. | |
| 7,905,877 B1 | 3/2011 | Jimenez et al. | |
| 7,935,092 B1 | 5/2011 | Odland et al. | |
| 7,939,332 B2 | 5/2011 | Colvin, Jr. | |
| 7,951,357 B2 | 5/2011 | Gross et al. | |
| 8,043,229 B2 | 10/2011 | Mulvihill et al. | |
| 8,073,548 B2 | 12/2011 | Colvin, Jr. et al. | |
| 8,143,068 B2 | 3/2012 | Colvin, Jr. et al. | |
| 8,157,773 B2 | 4/2012 | Tashjian | |
| 8,204,565 B2 | 6/2012 | Arnold et al. | |
| 8,206,343 B2 | 6/2012 | Racz | |
| 8,229,546 B2 | 7/2012 | Falkén et al. | |
| 8,273,061 B2 | 9/2012 | McConnell et al. | |
| 8,273,228 B2 | 9/2012 | Dall'Oglio et al. | |
| 8,303,533 B2 | 11/2012 | Regittnig et al. | |
| 8,318,193 B2 | 11/2012 | Ratner et al. | |
| 8,333,734 B2 | 12/2012 | Zohmann | |
| 8,403,911 B2 | 3/2013 | Adams et al. | |
| 8,415,184 B2 | 4/2013 | Colvin et al. | |
| 8,502,167 B2 | 8/2013 | Colvin, Jr. et al. | |
| 8,535,537 B2 | 9/2013 | Feichtner et al. | |
| 8,604,810 B2 | 12/2013 | Sheppard | |
| 8,608,922 B2 | 12/2013 | Papadimitrakopoulos et al. | |
| 8,647,393 B2 | 2/2014 | Marshall et al. | |
| 8,827,979 B2 | 9/2014 | Pesach et al. | |
| 9,084,848 B2 | 7/2015 | Schiltges et al. | |
| 9,131,960 B2 | 9/2015 | Racz | |
| 9,227,013 B2 | 1/2016 | Lacy | |
| 9,579,452 B2 | 2/2017 | Adair et al. | |
| 9,782,536 B2 | 10/2017 | Skutnik et al. | |
| 9,968,742 B2 | 5/2018 | Antwerp et al. | |
| 2002/0123740 A1 * | 9/2002 | Flaherty | A61M 5/14248 604/890.1 |
| 2004/0158207 A1 * | 8/2004 | Hunn | A61M 5/158 604/164.01 |
| 2005/0137525 A1 * | 6/2005 | Wang | A61M 37/0015 604/93.01 |
| 2005/0273076 A1 * | 12/2005 | Beasley | A61M 5/158 604/526 |
| 2006/0122536 A1 | 6/2006 | Haar et al. | |
| 2006/0135981 A1 | 6/2006 | Lenker et al. | |
| 2006/0211933 A1 | 9/2006 | Zimmermann et al. | |
| 2007/0060834 A1 | 3/2007 | Odland et al. | |
| 2007/0282269 A1 | 12/2007 | Carter et al. | |
| 2008/0108950 A1 * | 5/2008 | Rioux | A61B 17/064 604/181 |
| 2008/0243085 A1 | 10/2008 | DeStefano | |
| 2010/0063445 A1 * | 3/2010 | Sternberg | A61M 5/385 604/122 |
| 2010/0160749 A1 | 6/2010 | Gross et al. | |
| 2010/0298830 A1 * | 11/2010 | Browne | A61B 17/1615 606/79 |
| 2010/0303772 A1 | 12/2010 | McMillan et al. | |
| 2012/0265034 A1 | 10/2012 | Wisniewski et al. | |
| 2013/0126349 A1 | 5/2013 | Zhang | |
| 2015/0051583 A1 | 2/2015 | Horvath et al. | |
| 2015/0112302 A1 | 4/2015 | Chattaraj et al. | |
| 2015/0290390 A1 | 10/2015 | Ring et al. | |
| 2017/0021096 A1 | 1/2017 | Cole et al. | |

FOREIGN PATENT DOCUMENTS

| | | |
|---|---|---|
| WO | WO2012/073097 A2 | 6/2012 |
| WO | WO2012/118762 A1 | 9/2012 |
| WO | WO2017/053572 A1 | 3/2017 |
| WO | WO2018/184012 A1 | 10/2018 |

OTHER PUBLICATIONS

Calthorpe, N., The history of spinal needles: getting to the point; Anaesthesia; 59(12); pp. 1231-1241; Dec. 2004.

Campolo et al., Protocols to compare infusion distribution of wound catheters; Med. Eng. Phys.; 34(3); pp. 326-332; Apr. 2012.

(56) References Cited

OTHER PUBLICATIONS

Cho et al., On-line near-infrared spectrometer to monitor urea removal in real time during hemodialysis; Appl. Spectrosc.; 62(8); pp. 866-872; Aug. 2008.

Dziubla et al., Evaluation of porous networks of poly(2-hydroxyethyl methacrylate) as interfacial drug delivery devices; Biomaterials; 22(21); pp. 2893-2899; Nov. 2001.

Edsberg et al., Insulin bolus given by sprinkler needle: effect on absorption and glycaemic response to a meal; Br. Med. J. Clin. Res. Ed.; 294(6584); pp. 1373-1376; May 30, 1987.

Jockel et al., Insulin depot formation in subcutaneous tissue; J. Diabetes Sci. Technol.; 7(1); pp. 227-237; Jan. 2013.

Miller et al., Current state of type 1 diabetes treatment in the U.S.: updated data from the T1D Exchange clinic registry; Diabetes Care; 38(6); pp. 971-978; Jun. 2015.

Pfutzner et al., Improved Insulin Absorption by Means of Standardized Injection Site Modulation Results in a Safer and More Efficient Prandial Insulin Treatment; A Review of the Existing Clinical Data; J. Diabetes Sci. Technol.; 9(1); pp. 116-122; Jan. 2015.

Walsh et al., Insulin Pump and CGM Usage in the United States and Germany: Results of a Real-World Survey with 985 Subjects; J. Diabetes Sci. Technol.; 9(5); pp. 1103-1110; Sep. 2015.

Wootten et al., Broadband 2.4 μm superluminescent GaIn—AsSb/AlGaAsSb quantum well diodes for optical sensing of biomolecules; Semicond. Sci. Technol. (Internet); 29(11); doi: 10.1088/0268-1242/29/11/115014; Avail. from http://www.ncbi.nlm.nih.gov/pmc/articles/PMC4283575/; Nov. 2014.

Centers for Disease Control and Prevention (CDCP); National Diabetes Statistics Report, 2014—Estimates of Diabetes and Its Burden in the United States; U.S. Dept. of Health and Human Services, Atlanta, GA; 8 pgs.; (year of pub sufficiently earlier than effective US filing date and any foreign priority date) 2014.

Neithercott, T., Infusion Sets 2014—How to choose the kind of insulin delivery that's right for you; Diabetes Forecast®; (downloaded from the internet at http://www.diabetesforecast.org/2014/Jan/infusion-sets-2014.html on Dec. 6, 2018); Dec. 2013; 2 pgs.

Patel et al., Randomized trial of infusion set function: steel versus teflon; Diabetes Technol. and Ther.; 16(1); pp. 15-19; Jan. 2014.

\* cited by examiner

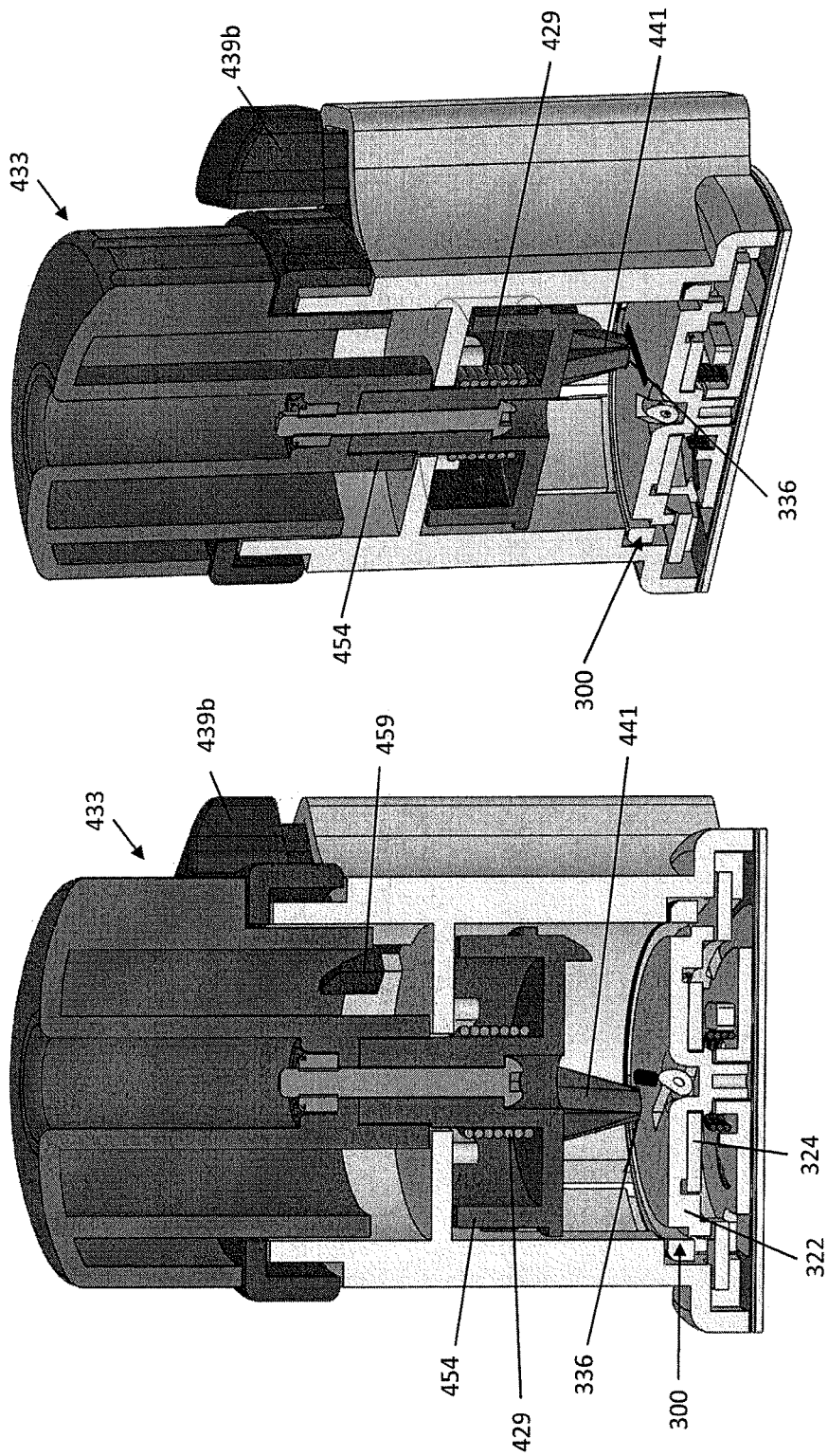

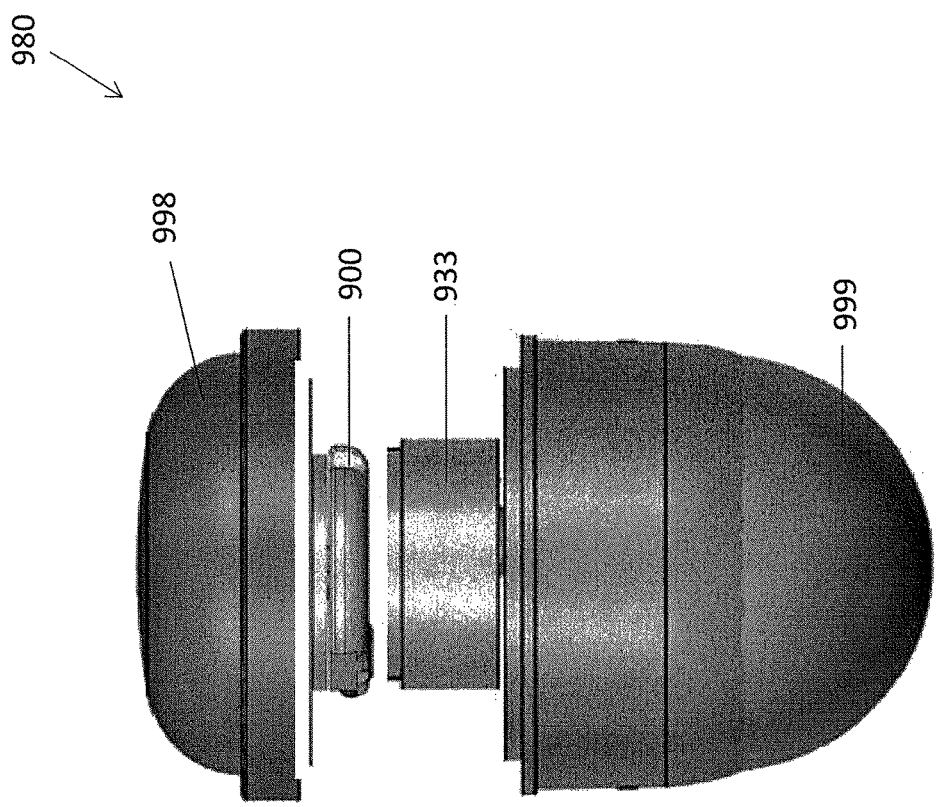

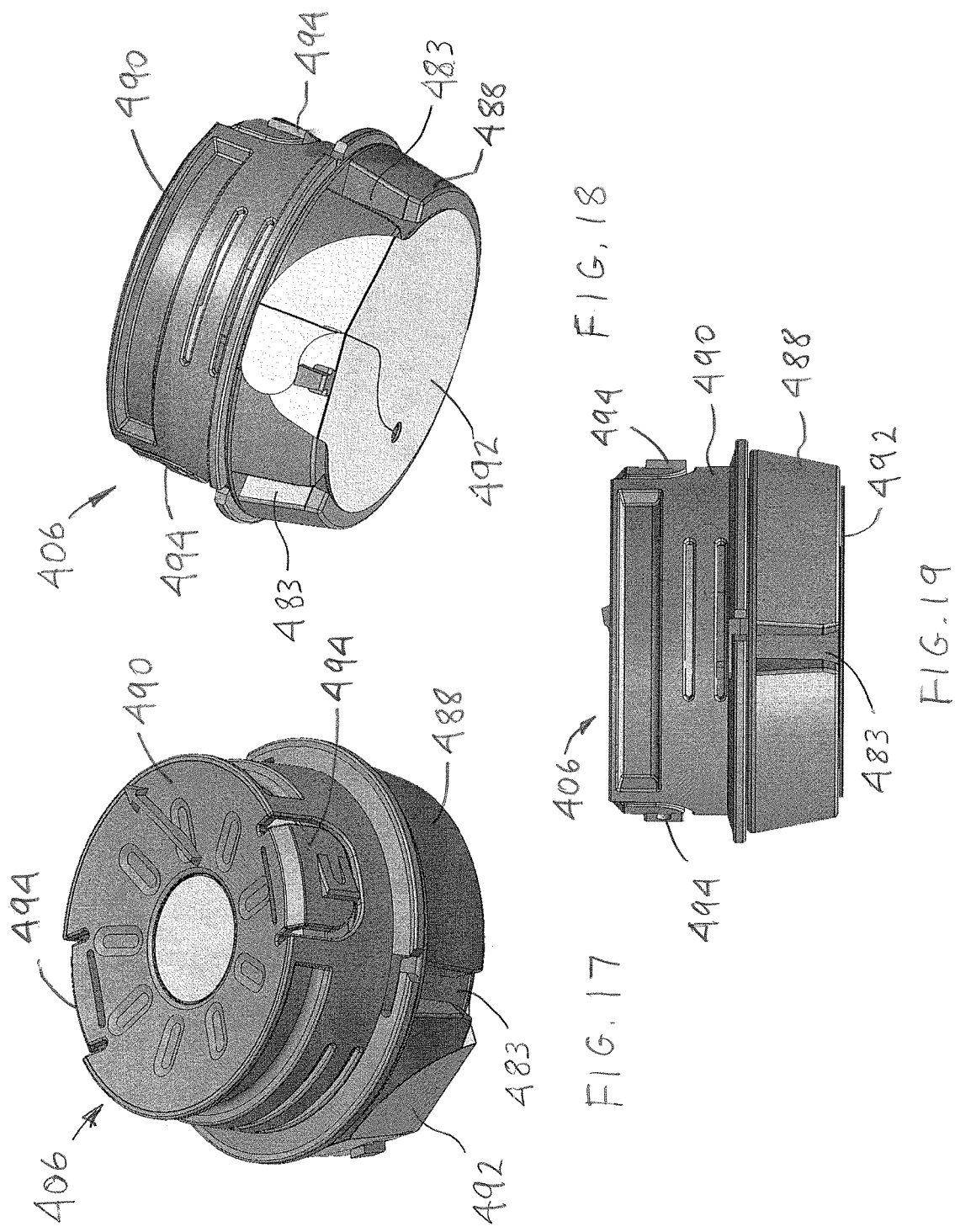

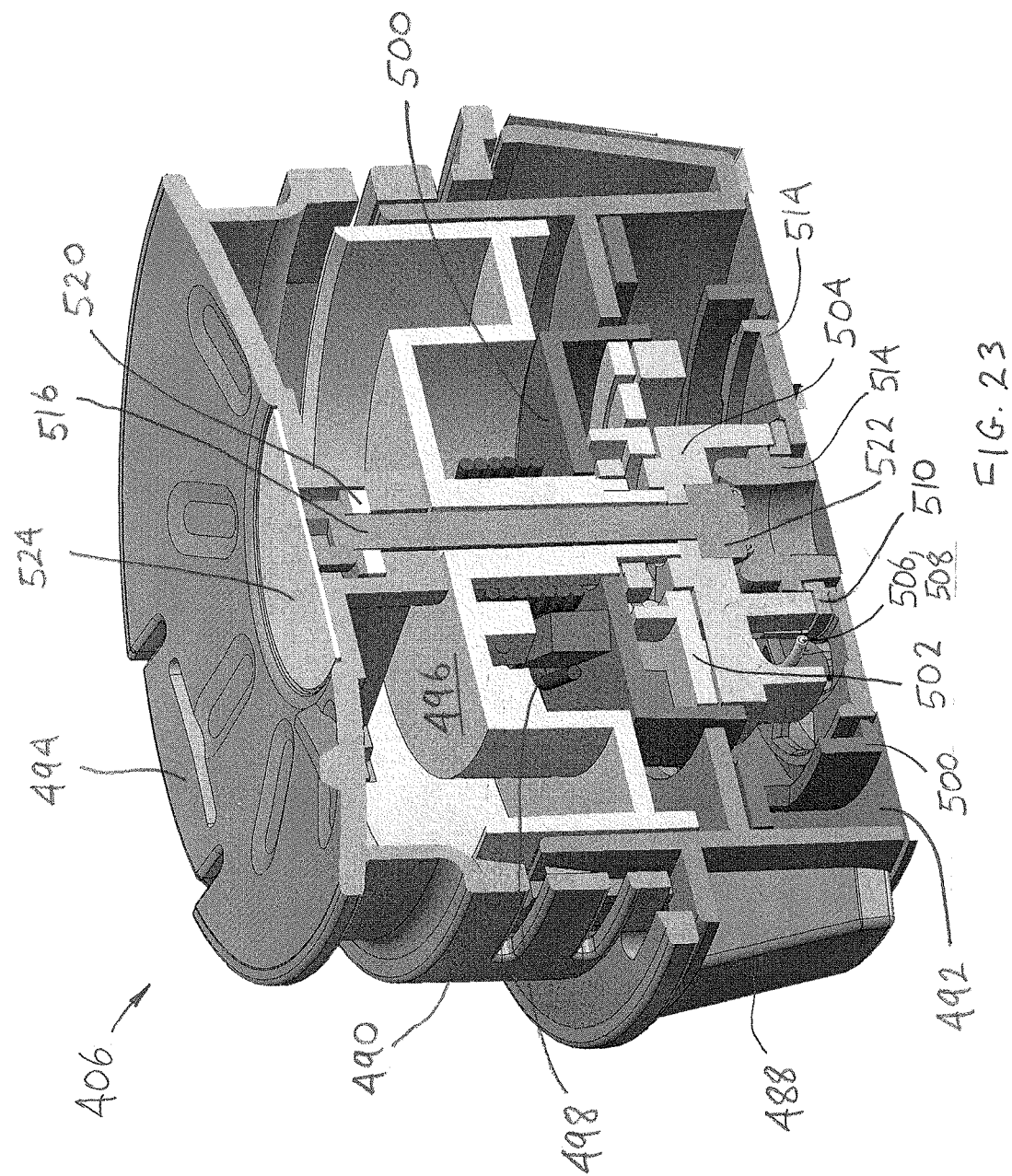

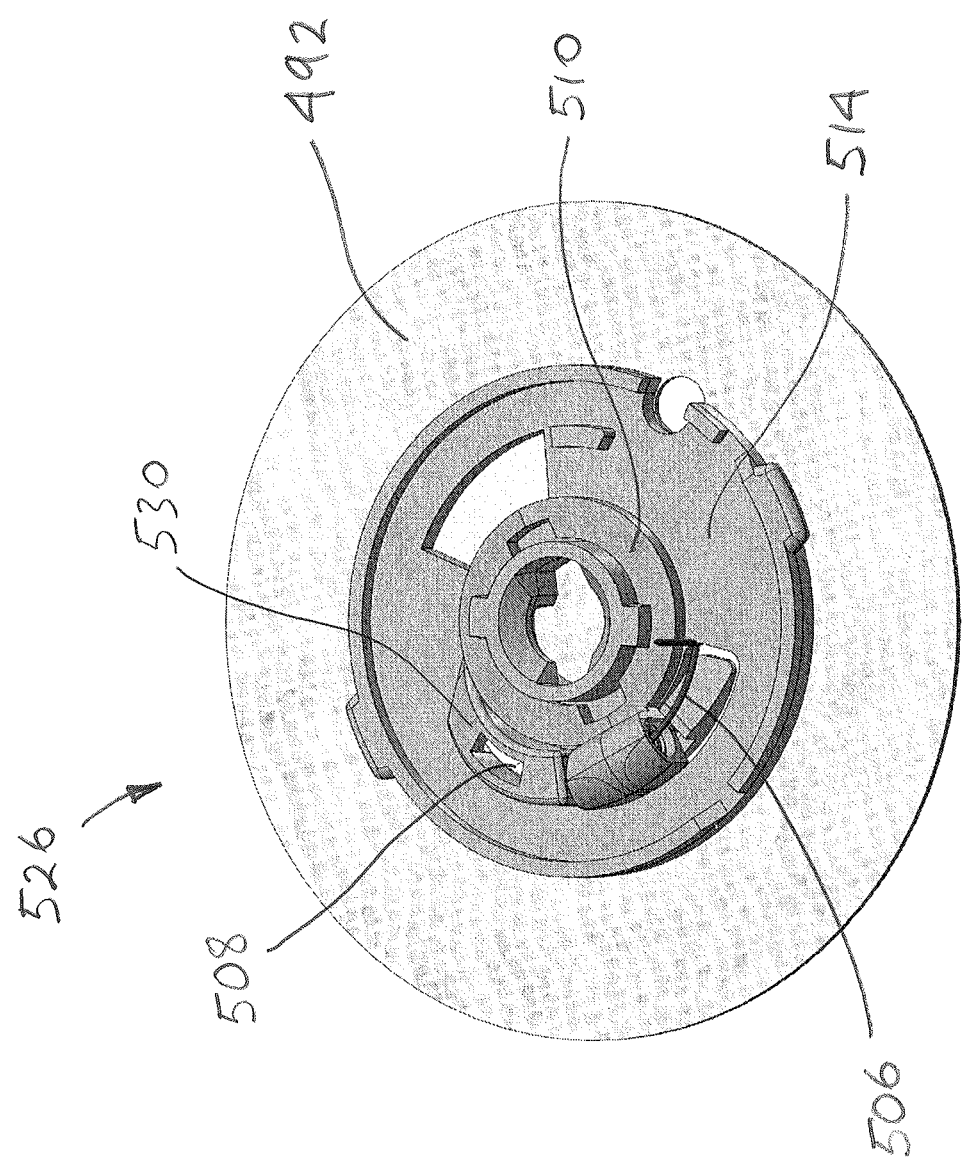

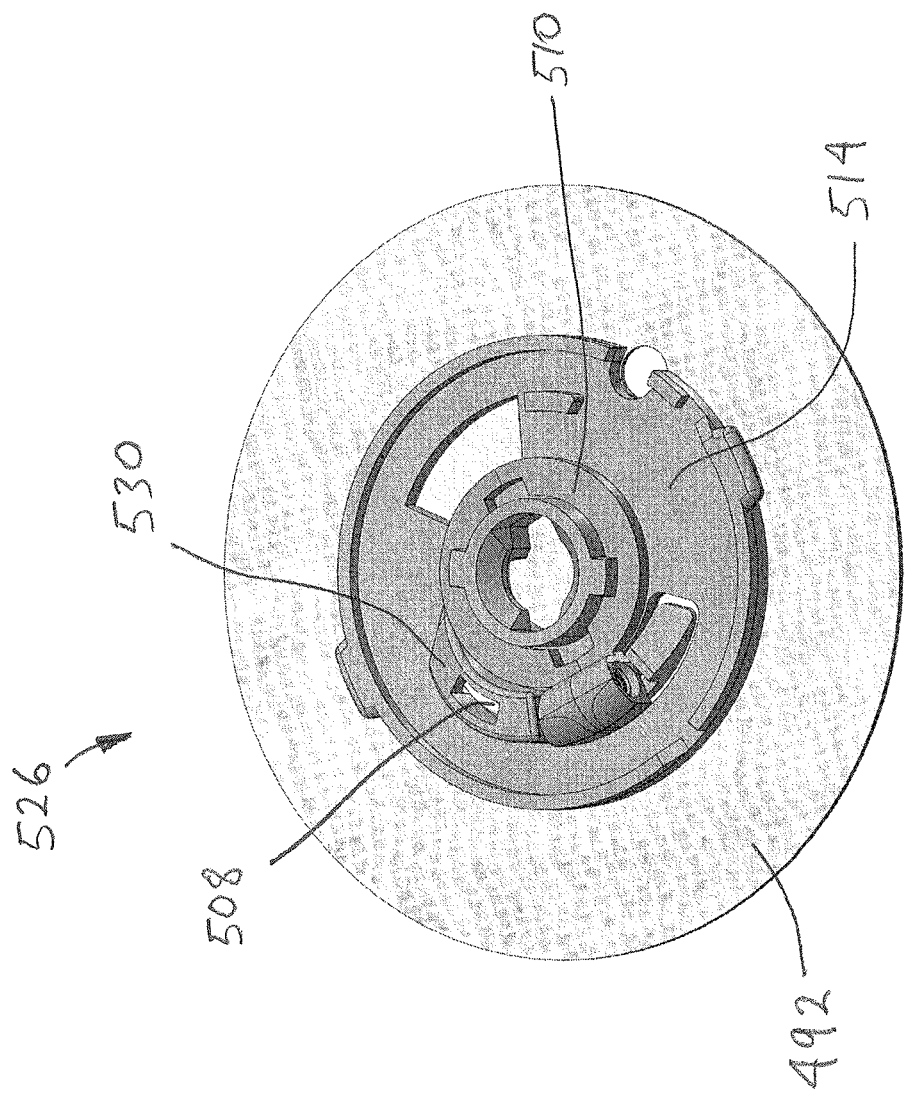

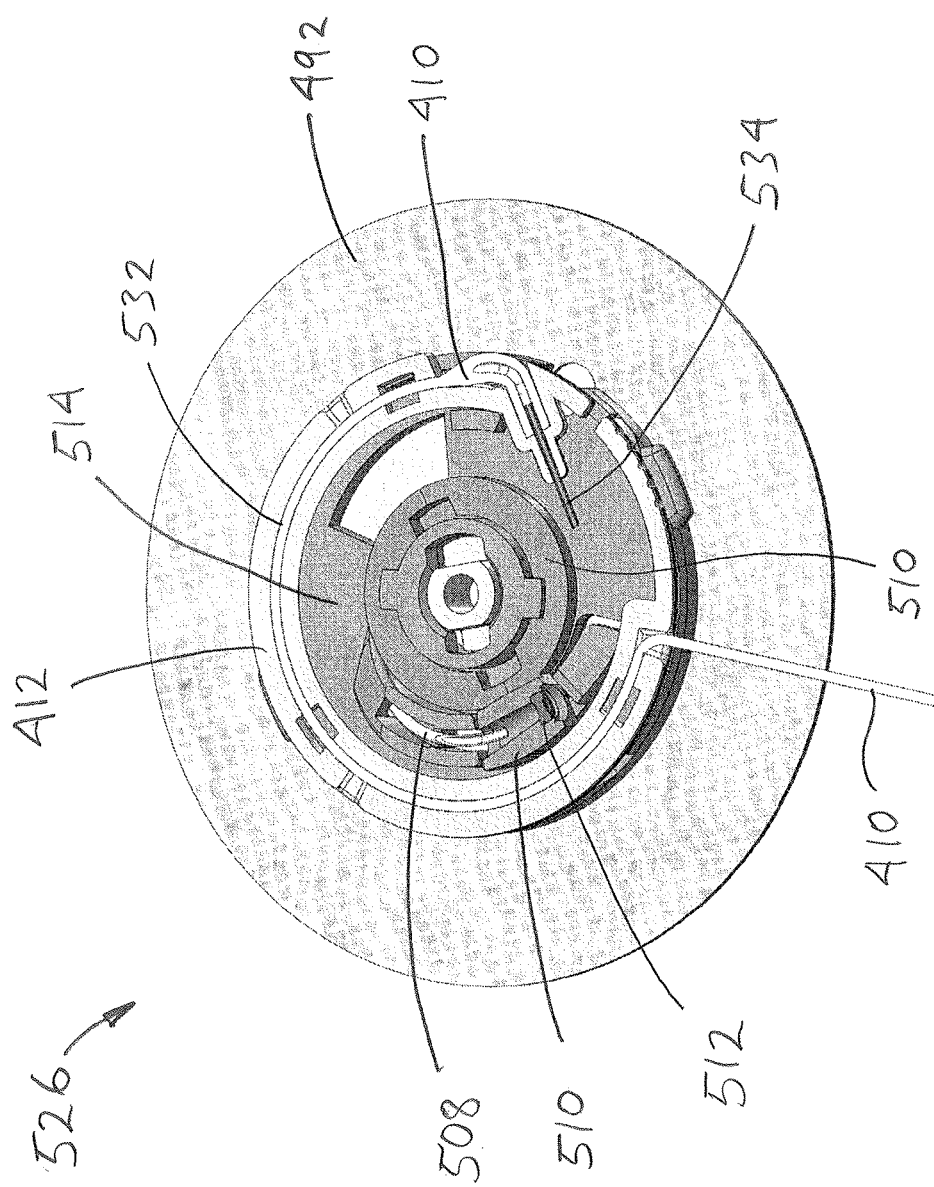

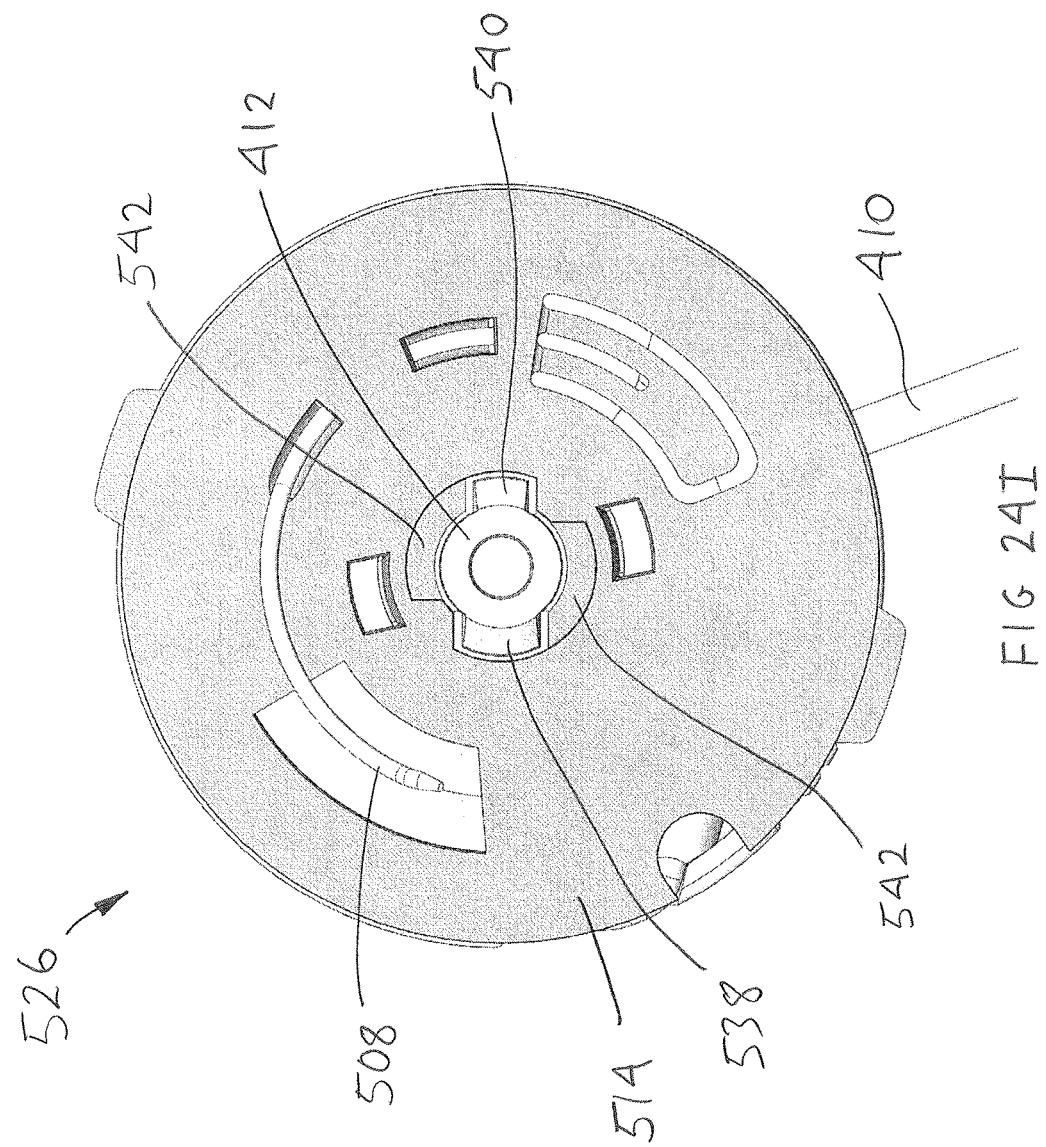

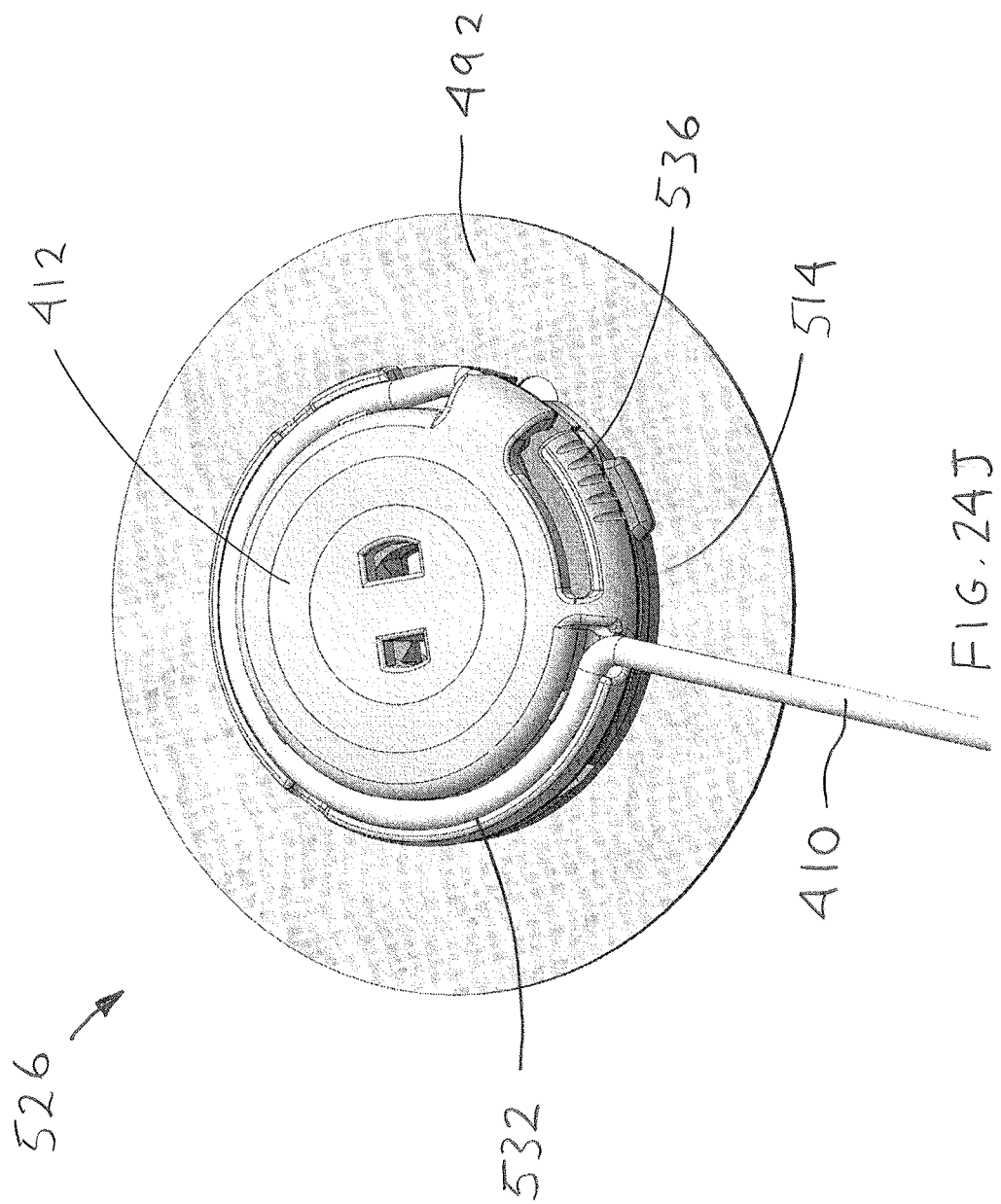

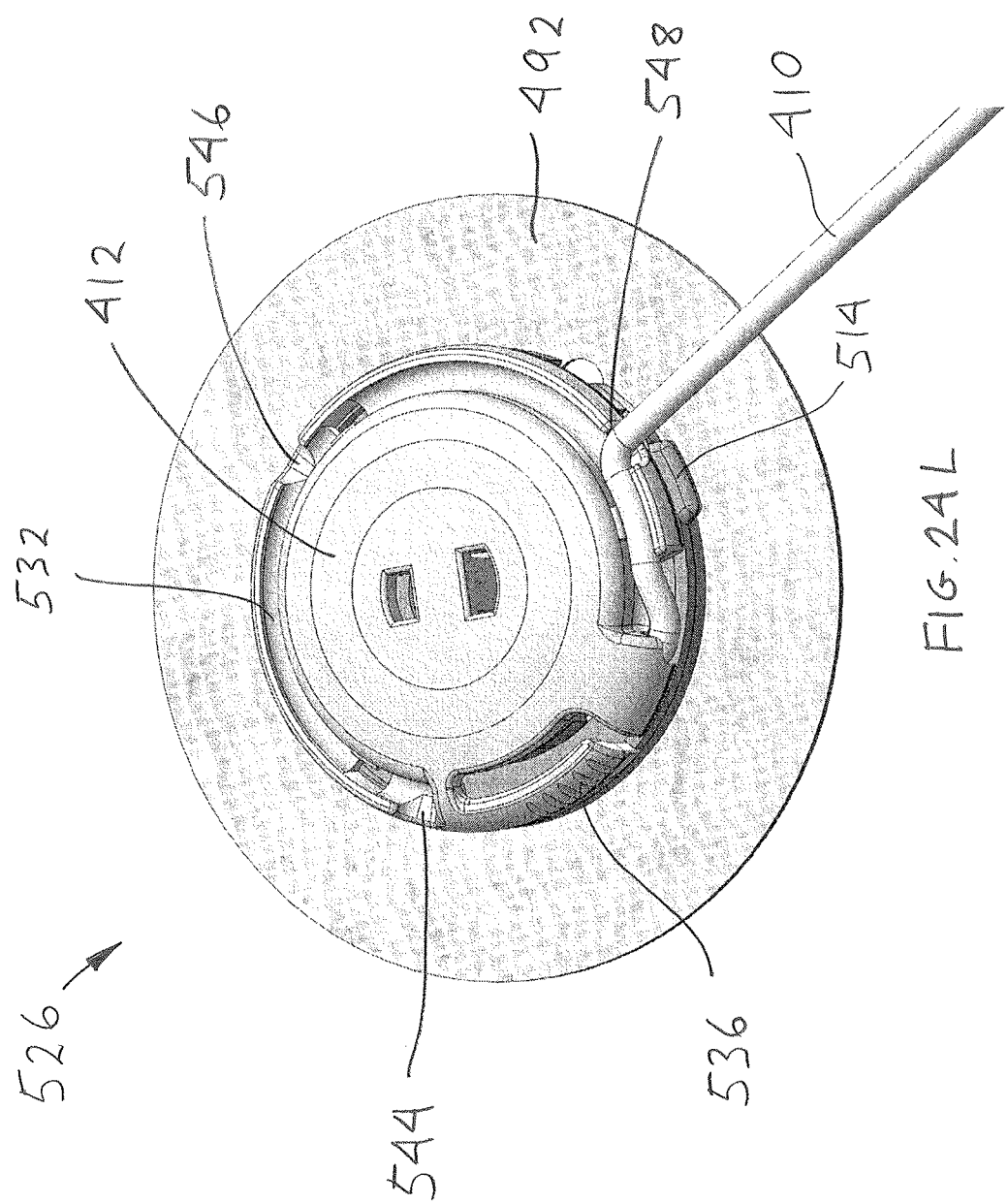

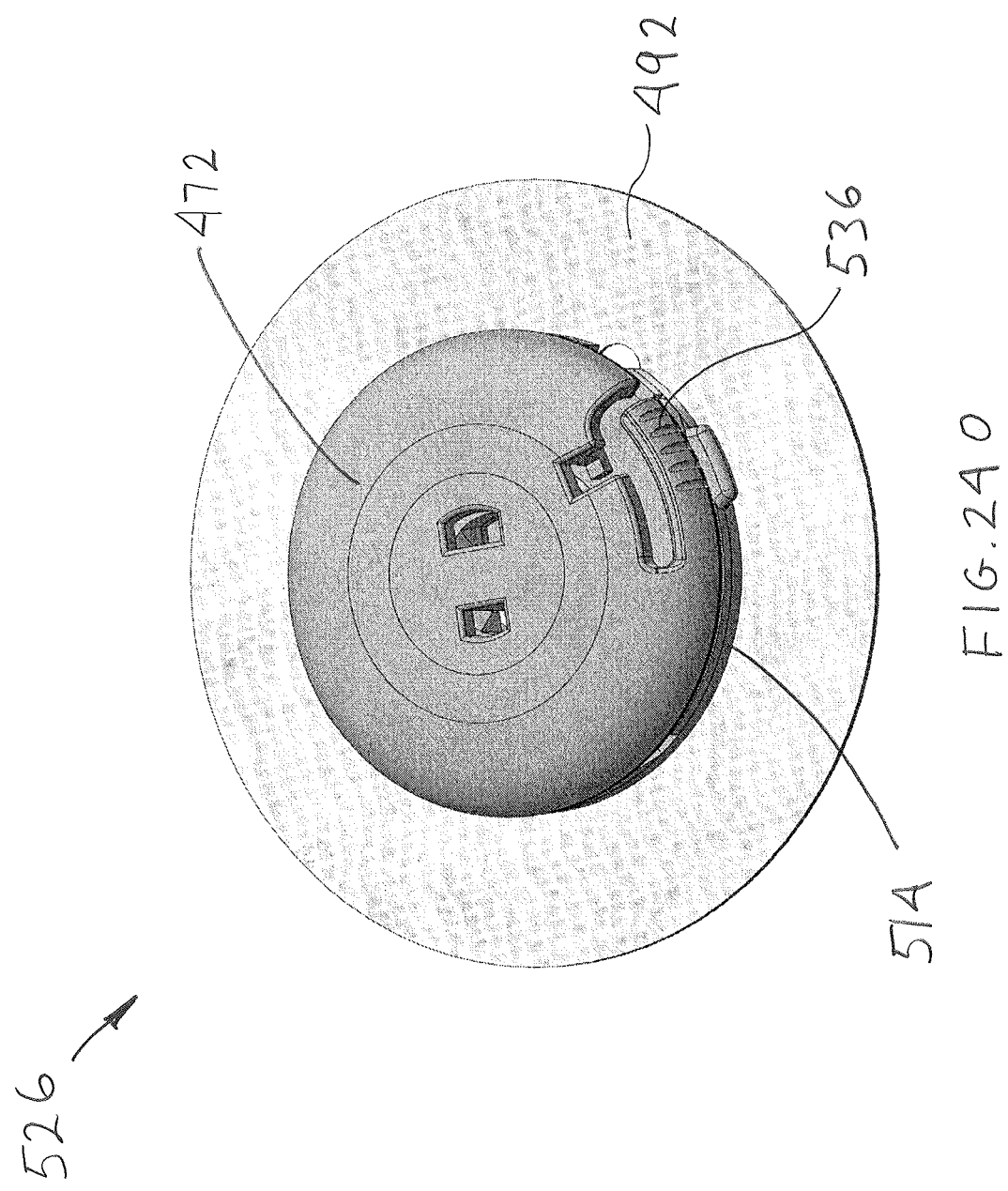

| | Depth [mm] | Cath Length [mm] | Angle [deg] | Arc Length [mm] | Sweep Angle [deg] | Pitch [mm] |
|---|---|---|---|---|---|---|
| Min | 4 | 14 | 16.60 | 13.42 | 107.59 | 13.39 |
| Nominal | 7 | 14 | 30.00 | 12.12 | 97.23 | 25.94 |
| Max | 9 | 14 | 40.01 | 10.72 | 85.99 | 37.70 |

Curve Radius [mm]: 7.15

HELICAL INSERTION INFUSION DEVICE

CROSS REFERENCE TO RELATED APPLICATIONS

This application claims the benefit of U.S. Provisional Patent Application No. 62/480,190, filed Mar. 31, 2017 and titled "SPIRAL INSERTION INFUSION DEVICE," and U.S. Provisional Patent Application No. 62/517,825, filed Jun. 9, 2017 and titled "SPIRAL INSERTION DEVICE," each of which is here incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are devices for delivering therapeutic fluids, and more particularly small, disposable, portable infusion devices and methods that can be used to transcutaneously deliver fluids safely and simply to a patient.

BACKGROUND

During drug delivery, it is often desirable to bypass the digestive system of a patient to avoid degradation of the drug's active ingredients that can be caused by the catalytic enzymes in the digestive tract and liver. Delivery of a drug other than by way of the intestines is known as parenteral delivery. Parenteral delivery of drugs in liquid form is often desired to enhance the effect of the substance being delivered, insuring that the unaltered medicine reaches its intended site at a significant concentration. Moreover, undesired side effects associated with other routes of delivery, such as systemic toxicity, can potentially be avoided by parenteral delivery. Further, many medicines are only available in liquid form, and/or the liquid may have desirable characteristics that cannot be achieved with solid or pill form. Delivery of liquid medicines may best be accomplished by infusing directly into the cardiovascular system via veins or arteries, into the subcutaneous tissue, or directly into organs, tumors, cavities, bones, or other site-specific locations within the body.

Parenteral delivery of liquid medicines into the body is often accomplished by administering bolus injections using a needle and reservoir or continuously by gravity driven dispensers or transdermal patch technologies. Bolus injections often imperfectly match the clinical needs of the patient and usually require larger individual doses than are desired at the specific time they are given. Continuous delivery of medicine through gravity feed systems compromise the patient's mobility and lifestyle and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles that can provide bolus delivery, continuous infusion, and variable flow rate delivery. Ambulatory infusion pumps, however, can be problematic, as the user is generally forced to choose between a soft delivery cannula, which tends to have high initial failure rates and is prone to kinking, or a steel needle set, which has a lower initial failure rate but is associated with increased pain and shortened time of use. Additionally, the challenge with current infusion sets is that the 90-degree (i.e., rigid cannula) infusion sets, which are easiest to insert, are also associated with the highest rates of failure, partially due to needle breakage and/or fluid leaking out of the relatively short insertion path. Further, infusion sets with a soft cannula, however, tend to be harder to insert and/or are associated with increased apprehension/intimidation.

Moreover, a necessary and important step in preparing an infusion set for use is filling the tubing with liquid medicament, such as insulin to be delivered to a person with diabetes. This is often done by attaching the infusion set tubing to either the insulin pump reservoir or the insulin pump reservoir adaptor (e.g., a device that holds the reservoir into the pump). The pump is then programmed to fill the tubing with insulin. This is not an automatic process. The user is typically either asked to hold down a button until the tubing is filled or to program an amount believed to be sufficient to fill the tubing. The user is instructed not to move on to another step until they observe insulin drops exiting the distal end of the tubing to infusion site connection or the distal end of the infusion cannula. The observation confirms that the tubing has been filled.

Tube filling carries two risk cases. The first risk case is when the user attempts to fill the tube and makes the mistake of connecting the tube to an infusion set that has already been inserted into their body. This would prevent the user from knowing when the tube had been completely filled and would result in any excess insulin delivered in an attempt to fill the tube to be delivered to the pump user, resulting in an over delivery. Over delivery carries with it a significant risk of hypoglycemia (low blood glucose levels). The second risk case is incomplete filling of the tubing. Failure to completely fill the tubing can lead to under delivery of insulin. This in turn can lead to hyperglycemia (elevated glucose levels). The amount of missed insulin (10 to 15 units) can be approximately 25 to 50% of a typical pump user's daily dose (~42 units) but could exceed the total daily dose of a pump user with higher than typical insulin sensitivity. In many cases, the missed insulin associated with a non-filled or partially filled tube causes a significant health risk to the pump user. Filling the tubing is not an easy task, especially for those with any macular degeneration, as is often associated with diabetes progression.

Accordingly, an ambulatory infusion pump set that is efficient, safe, effective, easy to insert into a patient, and easy/safe to fill is desired.

SUMMARY OF THE DISCLOSURE

In general, in one embodiment, a device for delivering fluid to a patient includes a housing assembly, a subcutaneous infusion cannula assembly extending from the housing, an insertion mechanism, and a fluid connection port. The insertion mechanism is configured to extend the infusion cannula in a helical path from the housing assembly. The fluid connection port is configured to connect the device to a source of delivery fluid.

This and other embodiments can include one or more of the following features. The infusion cannula can have a pre-set curved shape. The device can further include a sharp inner stylet configured to extend through the infusion cannula. The sharp inner stylet can have a pre-set curved shape. The insertion mechanism can further include mechanical features to define or limit the depth of extension of the infusion cannula from the housing assembly. The insertion mechanism can further include a rotational drive mechanism configured to rotate the infusion cannula as the cannula is extended from the housing assembly. The rotational drive mechanism can be a spring. The housing can include an adhesive on at least one surface thereof configured to attach the device to skin of the patient. The subcutaneous infusion cannula can be flexible. The cannula can include an outer tube and an inner reinforcement coil. The cannula can include two or more fluid exit holes at or near the distal end thereof. The insertion mechanism can include an automatic retraction mechanism for moving the stylet from the advanced position to the retracted position on completion of the insertion cycle. The housing assembly can contain a releasable fluid interconnect assembly to connect the subcutaneous cannula assembly to the source of fluid.

In some embodiments, a system for delivering fluid to a user transcutaneously includes a subcutaneous infusion cannula base assembly, a cannula inserter assembly and a fluid connection assembly. The subcutaneous infusion cannula base assembly is configured to be located on the user's skin. The cannula inserter assembly is coupled to the cannula base assembly and is configured to drive an infusion cannula through the user's skin in a nominally helical trajectory. The fluid connection assembly is configured to fluidically connect the cannula base assembly to a source of delivery fluid.

In some of the above embodiments, the inserter assembly is removably coupled to the cannula base assembly. The system may further comprise a sharp inner stylet configured to extend through the infusion cannula. The sharp inner stylet may have a pre-set curved shape. In some embodiments, the cannula base assembly includes an adhesive on at least one surface thereof configured to attach the cannula base assembly to the user's skin. In some embodiments, the subcutaneous infusion cannula is flexible. The cannula may include an outer tube and an inner reinforcement coil. In some embodiments, the cannula includes two or more fluid exit holes at or near the distal end thereof.

In some embodiments, the inserter assembly includes an automatic retraction mechanism configured to move the stylet from an advanced position to a retracted position after completion of a cannula insertion cycle. The inserter assembly may also include an automatic release mechanism configured to decouple the inserter assembly from the cannula base assembly after completion of a stylet retraction cycle. The inserter assembly may be configured to automatically perform the cannula insertion cycle, the stylet retraction cycle and a release cycle in succession after a single trigger event without further interaction from the user. In some embodiments, the inserter assembly includes a single drive spring configured to supply all energy required to drive the cannula insertion cycle, the stylet retraction cycle and the release cycle. The system may further comprise packaging for enclosing at least the inserter assembly before use. The inserter assembly may include at least one drive spring, and the inserter assembly may be configured to automatically charge the drive spring as the packaging is being opened.

In some embodiments, the fluid connection assembly of the infusion system includes tubing and an element or assembly that changes color when the tubing has been primed with fluid. The fluid connection assembly may include a releasable fluid interconnect assembly configured to releasably connect the cannula base assembly to the source of delivery fluid, and the source of delivery fluid may be external to the cannula base assembly. The releasable fluid interconnect assembly may include a needle and a septum, and the fluid interconnect assembly may be configured to insert an end of the needle through the septum after a cannula stylet is withdrawn from the septum.

In some embodiments, a system for delivering fluid to a user transcutaneously includes a subcutaneous infusion cannula base assembly, a cannula inserter assembly and a fluid connection assembly. The cannula base assembly is configured to be located on the user's skin and includes an infusion cannula having a central lumen therethrough. The cannula includes a reinforcing coil extending along a portion of the central lumen. The coil has at least two different pitches along its length. The cannula inserter assembly is coupled to the cannula base assembly and includes a sharp stylet configured to pass through the central lumen of the cannula. The inserter assembly is configured to drive the stylet and infusion cannula together through the user's skin without a needle placed over the cannula. The fluid connection assembly is configured to fluidically connect the cannula base assembly to a source of delivery fluid.

In some of the above embodiments, the reinforcing coil has a first section with a first coil pitch and a second section with a second coil pitch, the first section being located more distally in the cannula than the second section. In these embodiments, the first coil pitch is greater than the second coil pitch. In some embodiments, the first coil pitch is an open pitch and the second coil pitch is a closed pitch. In some embodiments, the first section includes a plurality of holes though a side wall of the cannula. The inserter assembly may be configured to drive the stylet and infusion cannula together through the user's skin at a 90 degree angle. The inserter assembly may be configured to drive the stylet and infusion cannula together through the user's skin at an angle of less than 45 degrees.

In some embodiments, a system for delivering fluid to a user transcutaneously includes a subcutaneous infusion cannula base assembly, a cannula inserter assembly and a fluid connection assembly. The cannula base assembly is configured to be located on the user's skin and includes an infusion cannula formed from a polyether block amide thermoplastic elastomer having a central lumen therethrough. The cannula has a nominal outside diameter no greater than 0.56 mm. The cannula includes a reinforcing coil extending along a portion of the central lumen. The reinforcing coil has a nominal inside diameter and a nominal outside diameter. The nominal outside diameter is the same as a nominal inside diameter of the central lumen it resides in. The reinforcing coil has a first section with a first coil pitch and a second section with a second coil pitch. The first coil section is located more distally in the cannula than the second section. The first coil pitch is an open pitch and the second coil pitch is a closed pitch. The first section includes a plurality of holes though a side wall of the cannula. The cannula includes a distalmost section having an outer taper of between 10 and 30 degrees and no reinforcing coil located in the distalmost section. A portion of the cannula is siliconized to reduce insertion force. The cannula inserter assembly is coupled to the cannula base assembly and includes a sharp stylet configured to pass through the central lumen of the cannula. The stylet has a nominal outside diameter that is the same as the nominal inside diameter of the reinforcing coil. The stylet has a sharpened distal tip that extends from the distalmost section of the cannula. The inserter assembly is configured to drive the stylet and cannula together through the user's skin without a needle placed over the cannula. The fluid connection assembly is configured to fluidically connect the cannula base assembly to a source of delivery fluid.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIGS. 5B and 5C are cross-sections of FIG. 5A taken along a vertical plane.

FIGS. 9A-9C show an infusion device and an external inserter combined in a single packaging element.

FIG. 17 is a top perspective view showing the inserter assembly of the infusion system of FIG. 11.

FIG. 18 is a bottom perspective view showing the inserter assembly of the infusion system of FIG. 11.

FIG. 19 is a side view showing the inserter assembly of the infusion system of FIG. 11.

FIG. 23 is a cross-sectional view taken between the release buttons of the inserter assembly of the infusion system of FIG. 11.

DETAILED DESCRIPTION

Described herein are subcutaneous infusion devices that promote wearability, increase wear-life, and effectively deliver fluid transcutaneously. The in-dwelling infusion devices may include a multi-orifice soft cannula and a user-depth controlled curved insertion cannula that provides for a spiral or helical insertion path through the tissue.

Figure 1A:
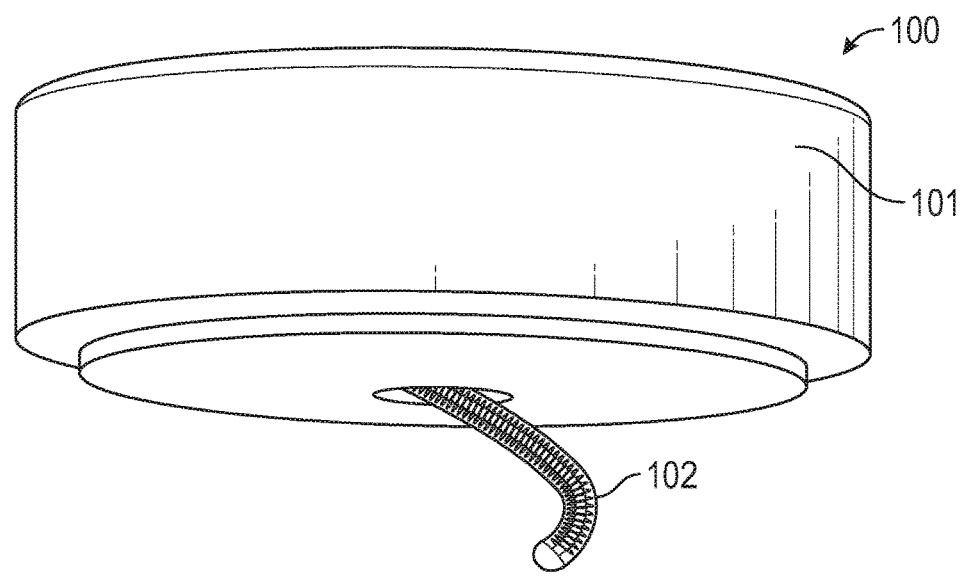
FIG. 1A shows an exemplary infusion device.
Figure 1B:
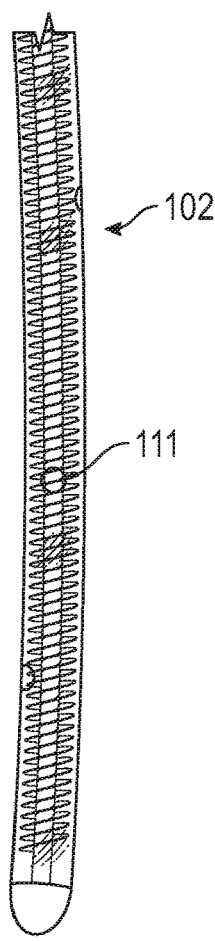
FIG. 1B shows an exemplary cannula for use with the infusion device of FIG. 1A.

As shown in FIGS. 1A and 1B, an exemplary infusion device 100 includes a housing assembly 101, a hollow curved cannula 102, and a driver to which the hollow curved cannula 102 is attached. The driver rotates the hollow curved cannula 102 and simultaneously translates the hollow curved cannula 102 into the soft tissue. The device 100 is configured to insert the curved cannula 102 spirally or helically into soft tissue, thereby better fixing the cannula 102 in the soft tissue. In some embodiments, the infusion device 100 can be configured to interface with an infusion pump.

In some embodiments, the hollow curved cannula 102 can be a 24 Ga catheter (0.56 m outer diameter) made of a polymer-coated stainless steel coil. In other embodiments, the cannula 102 can be made entirely of metal, e.g., stainless steel. The curved shape can, for example, be heat set into the cannula 102. The curved shape of the cannula 102 can, for example, have a radius of curvature of between 0.5 inches and 1.25 inches. Further, the curved shape of the cannula 102 can have a pitch, for example, of between 10 mm and 30 mm. In some embodiments, the cannula 102 can end in a sharpened tip. The hollow curved cannula 102 can further include a series of perforations, including one or more fluid exit holes 111 along the length thereof in a variety of patterns. Further, the hollow curved cannula 102, due to its curvature, can be inserted at a 30°-60° angle relative to the plane of the skin surface in a spiral or helical path that accommodates target insertion depths ranging from 6 to 10 mm. Further, in some embodiments, the curve of the hollow curved cannula can provide for a 1-3 cm diameter insertion path.

Figure 2A:
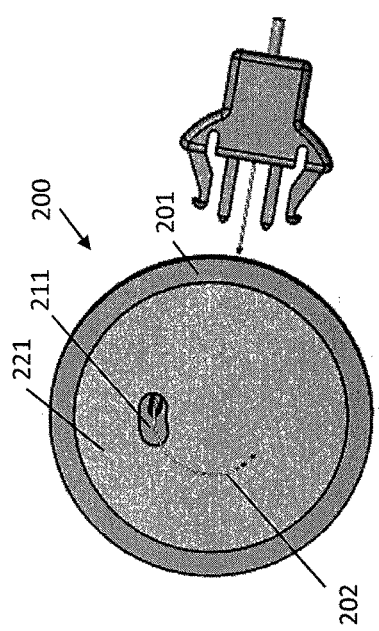
FIG. 2A shows the bottom surface of another exemplary infusion device.
Figure 2B:
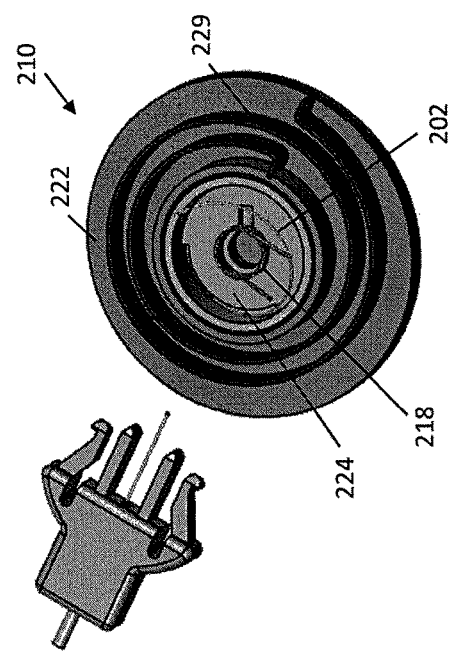
FIG. 2B shows a cannula release mechanism that can be positioned within the infusion device of FIG. 2A.

A similar infusion device 200 is shown in FIGS. 2A-2B. The infusion device 200 includes a housing 201. The underside 221 of the housing can be flexible and include an adhesive thereon for attachment to the skin. A release mechanism 210 can be positioned inside the housing 201 (FIG. 2B shows the housing removed for clarity). Further, the release mechanism 210 can include an rotatable disk 222 and an inner disk 224 that are rotatable with respect to one another. The cannula 202 can extend from the outer disk 222 and can be wound or curled up within the inner radius of the outer disk 222. The inner disk 224 can be fixed relative to the housing 201. A coiled or torsion spring 229 can be positioned within the release mechanism 210 and attached to both the inner disk 224 and the outer disk 222. Further, the spring 229 can be held in a loaded position when the cannula 202 is wound and positioned within the housing 201. Upon release of the spring 229 (e.g., by a user-activated button), the outer disk 222 can rotate relative to the inner disk 224, thereby causing the cannula 202 to rotate relative to the housing 201. As the cannula 202 rotates, it can extend from an aperture 211 on the bottom surface 221 of the housing 201, thereby allowing the sharp tip of the cannula 202 to pierce the skin and extend in a spiral or helical path through the subcutaneous tissue. A second coiled spring 218 within the release mechanism 210 can be loaded so as to rotate the outer disk 222 in the opposite direction relative to the inner disk 224 when released (e.g., by a user-activated button), thereby permitting the cannula 202 to be retracted into the housing 201 by the user as desired.

Figure 3A:
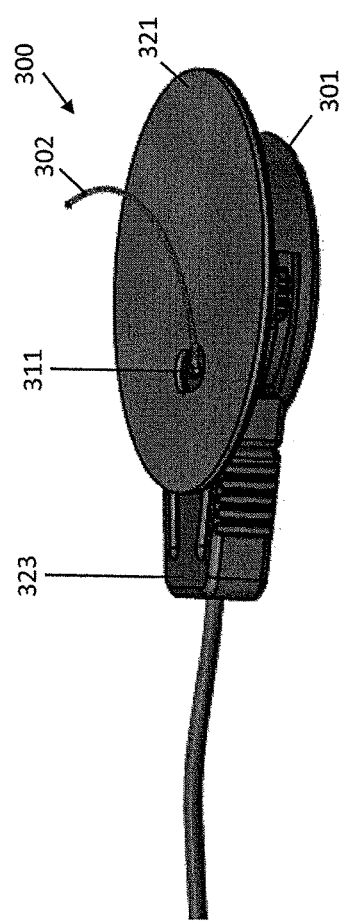
FIG. 3A shows another exemplary infusion device.
Figure 3B:
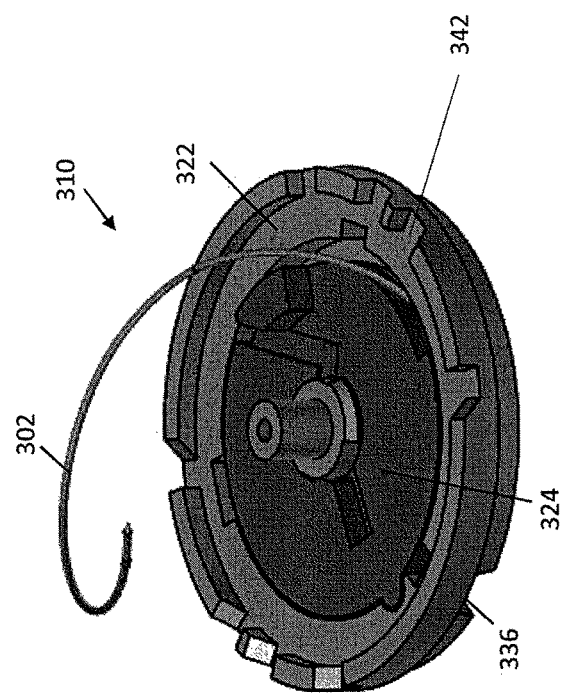
FIG. 3B shows a cannula release mechanism of the infusion device of FIG. 3A.
Figure 3C:
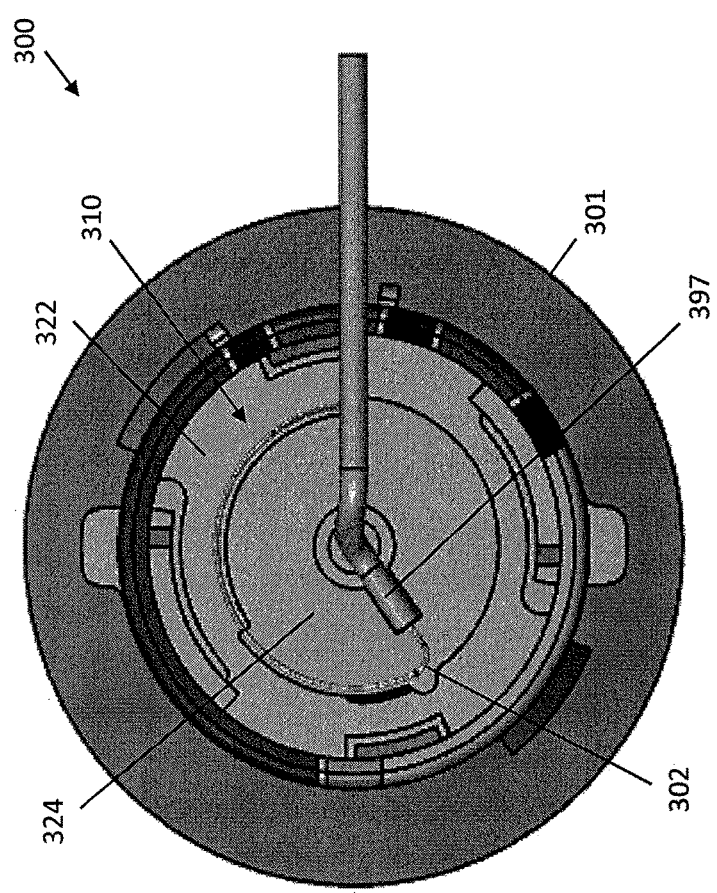
FIG. 3C is a cross section of the infusion device of FIG. 3A.
Figure 3D:
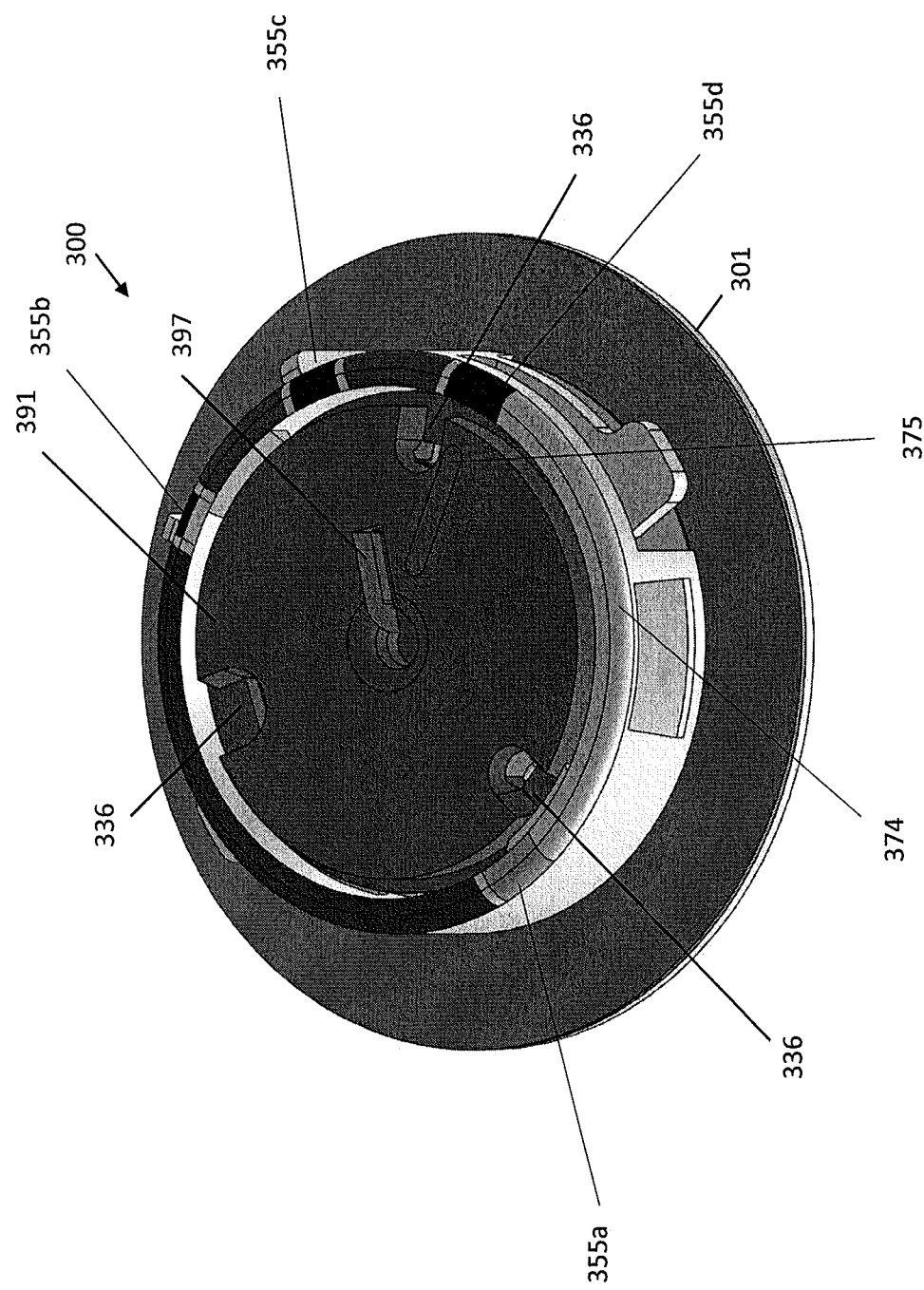
FIG. 3D shows the top of an infusion device of FIG. 3A.

Another similar infusion device 300 is shown in FIGS. 3A-3E. In contrast to infusion device 200, however, device 300 is intended to be used with a separate external insertion device. The infusion device 300 includes a housing 301 configured to house a release mechanism 310 and a curved cannula 302. Similar to the release mechanism 210, release mechanism 310 can include two disks 324, 322 that are rotatable relative to one another to allow the curved cannula 302 (fixed relative to the outer disk 322) to rotate and extend through the aperture 311 on the bottom surface 321 of the housing 301. This rotation can be activated, for example, through an external device such as that shown and described with respect to FIGS. 4A-4C. Further, the release mechanism 310 can include a second spring (see FIG. 3F) configured to retract the cannula 302 when released. The underside 321 of the housing 301 can be flexible and include an adhesive thereon for attachment to the skin. As shown in FIG. 3C, a fluid inlet 397 can provide delivery fluid to the needle 302 (e.g., through a detachable fluid connection 323).

The fluid inlet 397 can be fixed to the stationary inner disk 324, thereby maintaining a fixed position relative to the fluid reservoir.

Figure 4B:
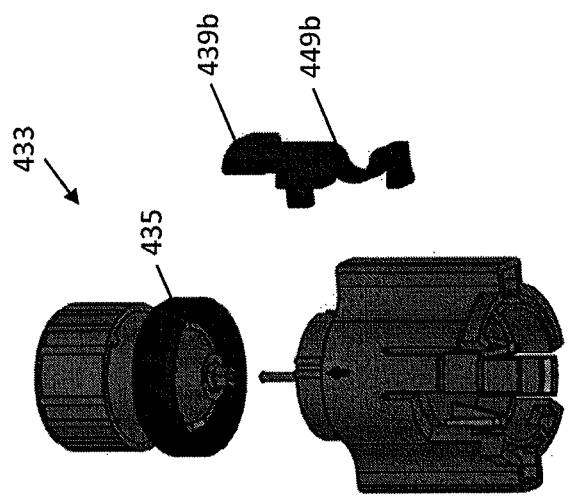
FIG. 4B is an exploded view of the external insertion device of FIG. 4A.
Figure 4A:
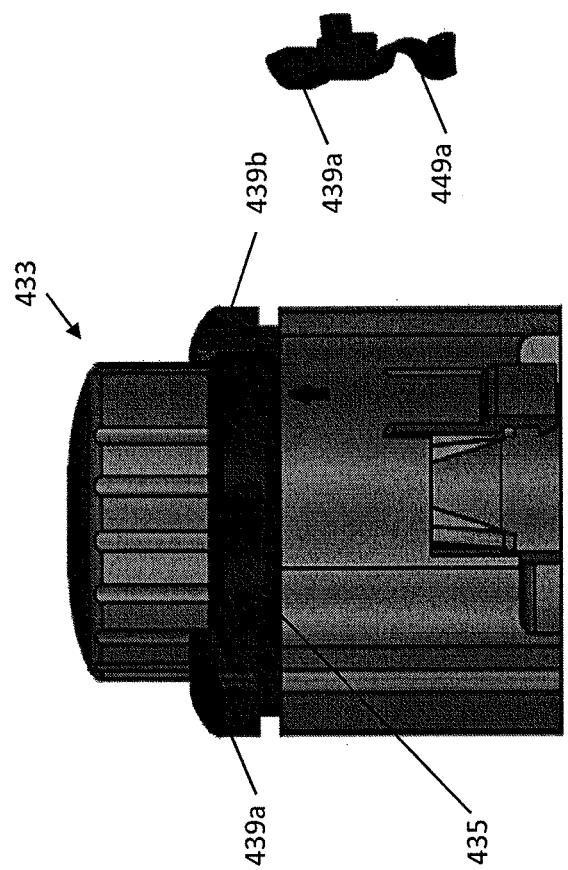
FIG. 4A shows an exemplary external insertion device.
Figure 4C:
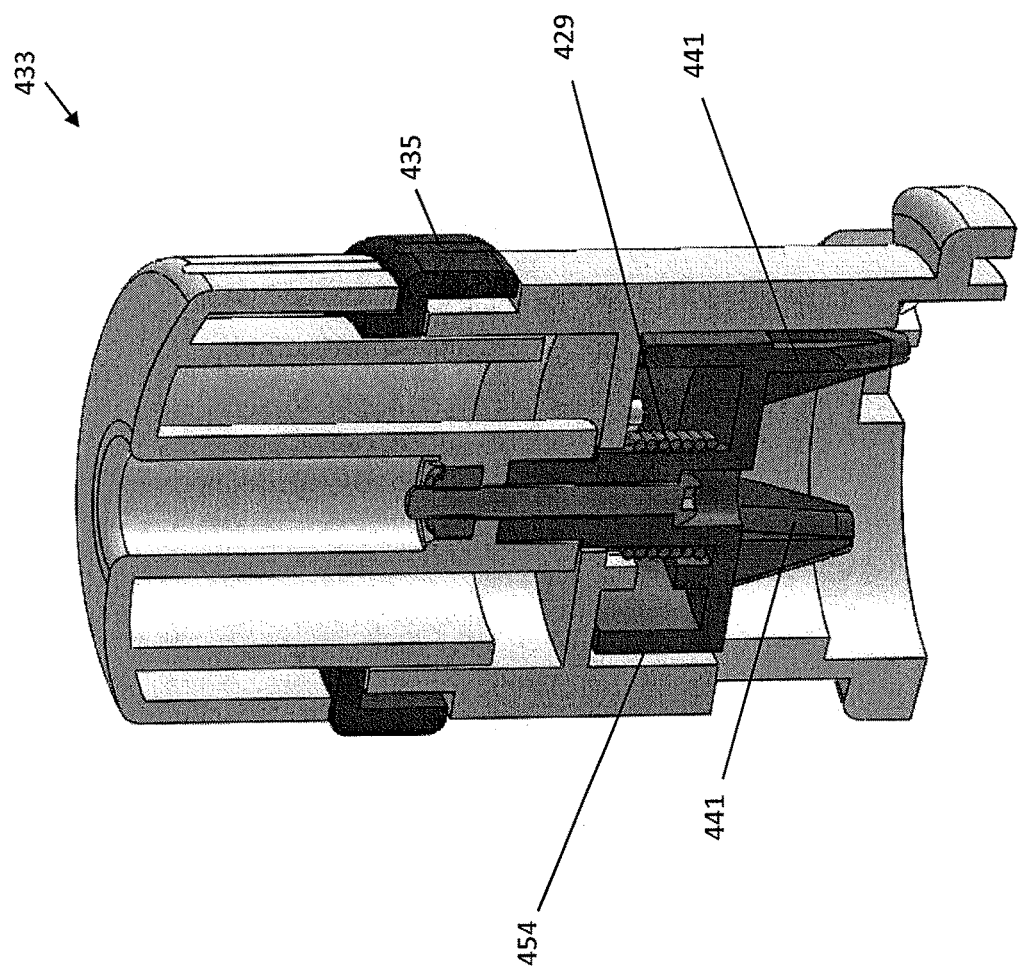
FIG. 4C is a cross section of the external insertion device of FIG. 4A.

As shown in FIGS. 4A-4C, an insertion device 433 can be configured to be used with the infusion devices (such as device 300) described herein. The insertion device 433 can separately house the torsion spring 429 and a rotatable portion 454. Buttons 439a,b can allow the user to release the spring 429 to provide rotation of the rotatable portion 454. Further, the insertion device 433 can include a user-adjustable knob 435 configured to allow the user to set the depth of insertion (e.g., at 6, 8, or 10 mm). The insertion device 433 can include features configured to positively engage with the infusion device. For example, legs 441 (see FIG. 4C) of the insertion device 433 can be configured to sit within indents 336 (see FIGS. 3B and 3D) on the cover 391 of the release mechanism 310.

Use of the insertion device 433 with the infusion device 300 is described with respect to FIGS. 5A-5E. To begin, the infusion device 300 is adhered to the skin. The inserter 433 can then be coupled with the device 300 such that the legs 441 of the insertion device 433 extend within the indents 336 of the device 300. To release the cannula 302 from the device 300 for insertion into the skin, the buttons 439a,b (two are included for redundancy, but only one may be used) can be pushed downwards. Pushing the buttons 439a,b downwards pushes on the compression springs 449a,b associated with the buttons 439a,b, which causes the internal fixation element(s) 459 (see FIG. 5B) to release from the rotatable portion 454. The torsion spring 429 will then release, causing the rotatable portion 454 to rotate, and thus the outer disk 322 of the insertion device 300 (and attached cannula 302) to rotate. Such rotation of the cannula 302 results in unwinding the cannula 302 and inserting the cannula 302 into the skin in a spiral/helical manner (consistent with the curvature of the cannula 302). Pushing of the buttons 439a,b downwards can also advantageously help adhere the device 300 to the patient's skin during insertion of the cannula 302.

Figure 5A:
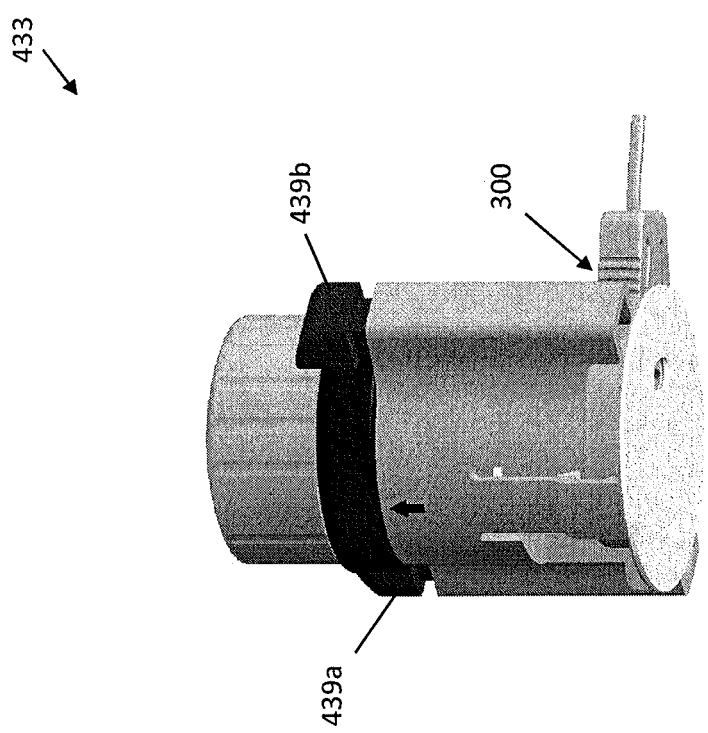
FIG. 5A shows an external insertion device mated with an infusion device.
Figure 5D:
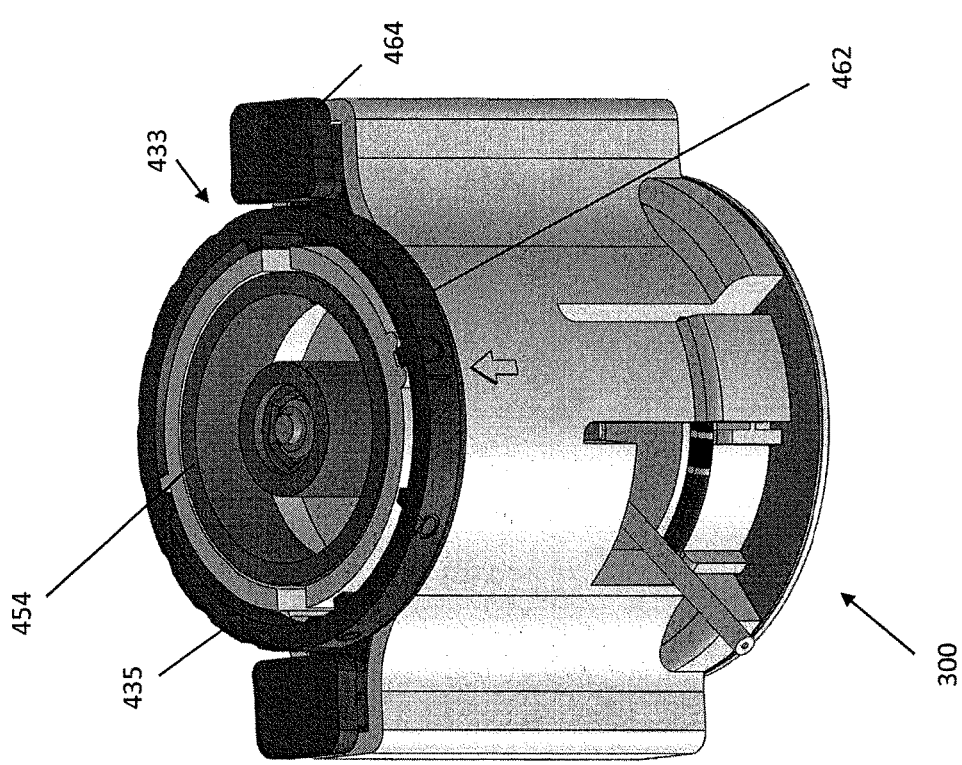
FIGS. 5D and 5E are cross-sections of FIG. 5A taken along a horizontal plane.
Figure 5E:
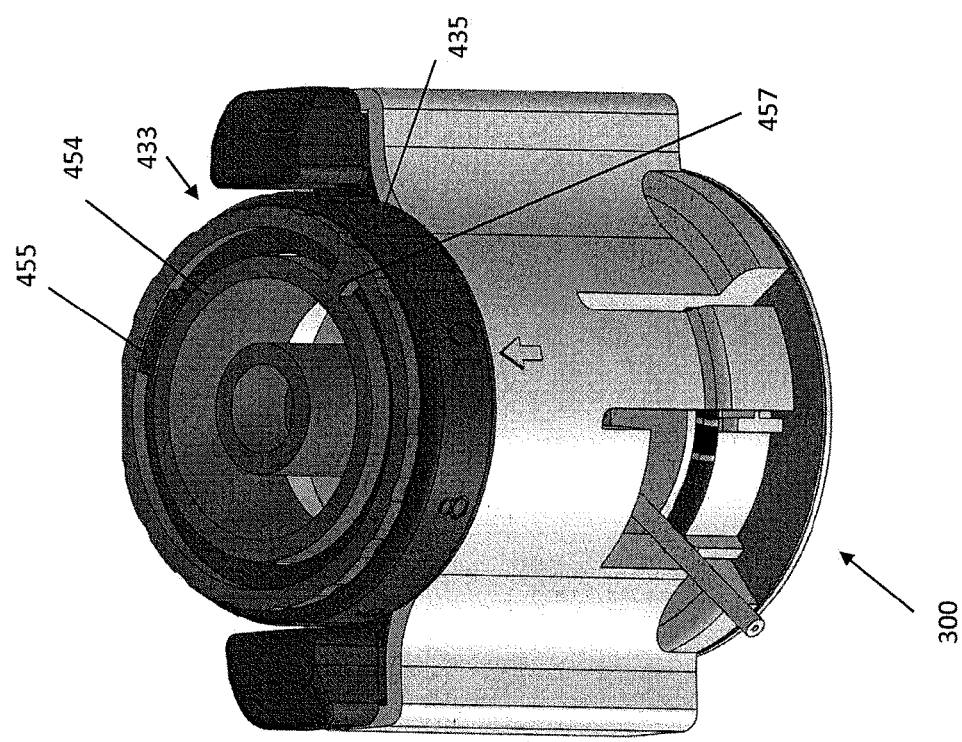
Figure 6C:
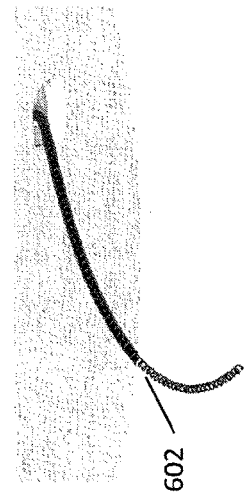
FIGS. 6A-6D show an exemplary cannula for use with the infusion devices described herein.
Figure 6D:
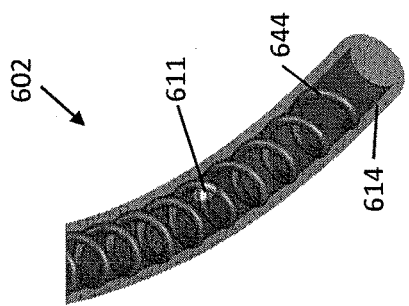
Figure 6A:
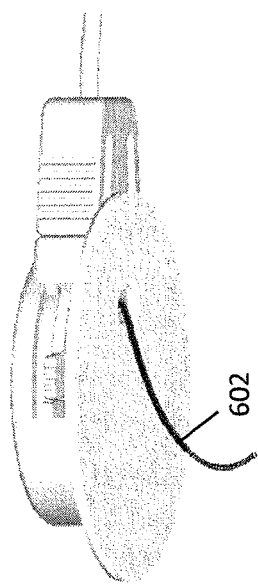
Figure 6B:
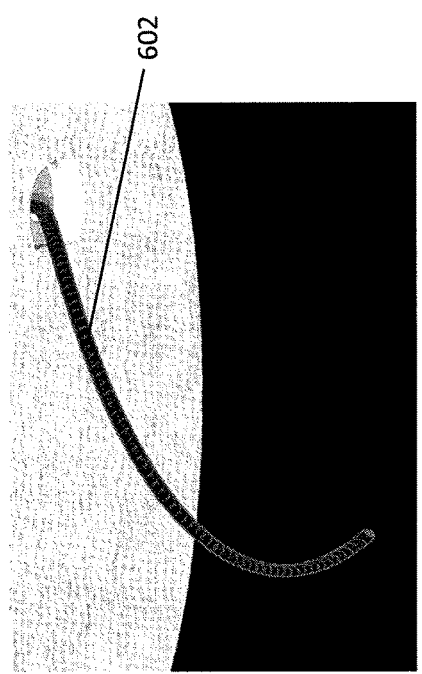

In some embodiments, the user can preselect the insertion depth using the knob 435 prior to inserting the cannula 302. As shown in FIGS. 5D-5E, as the knob 435 is rotated to the desired position, extensions 462 on the internal radius thereof engage with mating teeth 464 on an internal fixed portion of the device 433. Doing so establishes the position of a stop 455 (that rotates with knob 435). As such, when the rotatable portion 454 rotates, it will be allowed to rotate only until the mating stop 457 hits the stop 455, thereby controlling the length of the cannula 302 that is released, and thus controlling the depth of insertion.

Figure 3E:
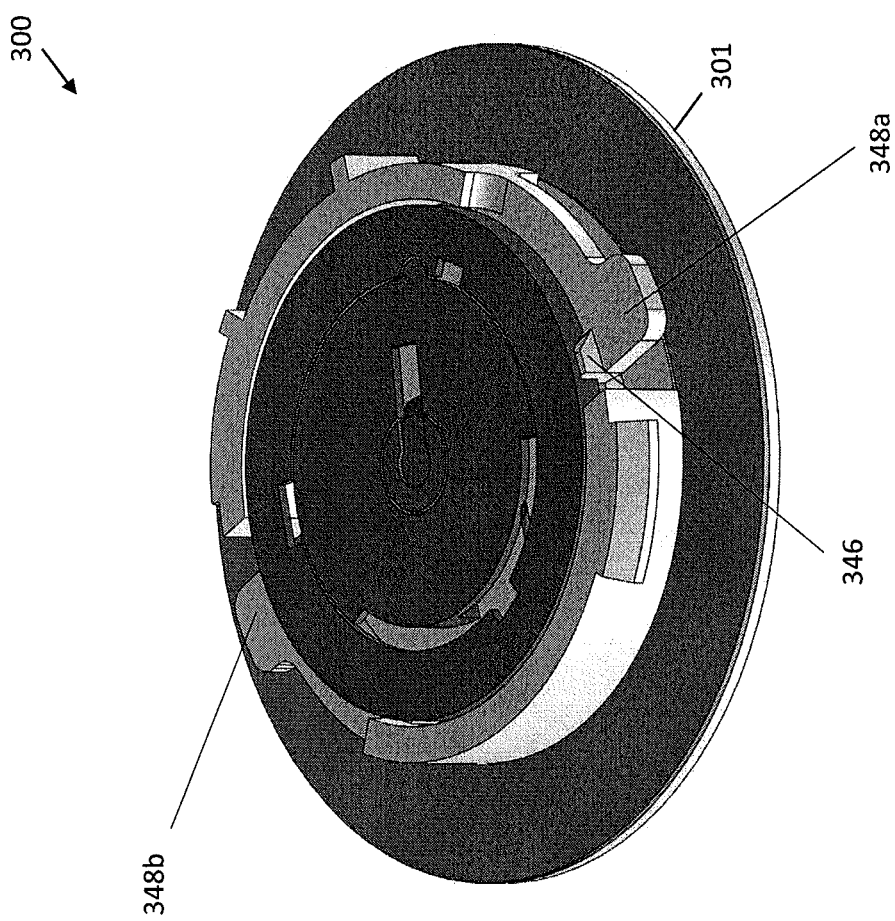
FIG. 3E is a cross section of the infusion device of FIG. 3A.
Figure 3F:
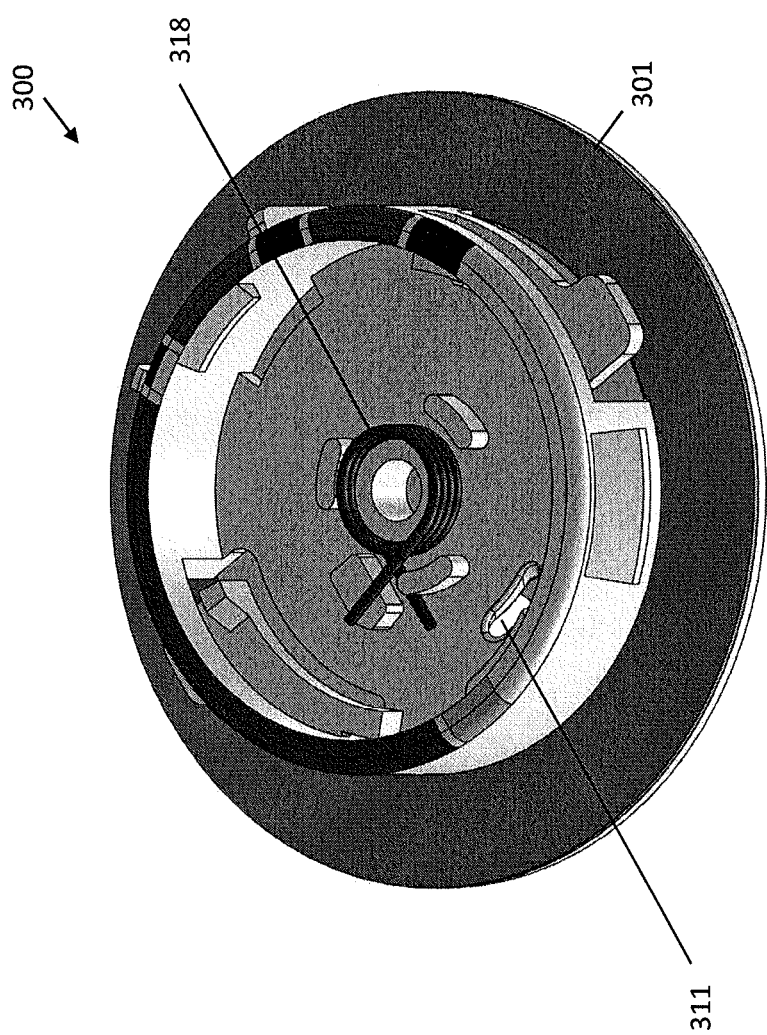
FIG. 3F shows the top of the infusion device of FIG. 3A with the cover removed.

In some embodiments, to remove the cannula 302 from the patient, the cannula 302 can be retracted back into the body 301. For example, as shown in FIG. 3E, the infusion device 300 can include two tabs 348a,b. When the tabs 348a is pushed inwardly, the hook 346 (which is usually engaged with teeth 342 on the outer surface of the outer disk 322) can move inwards to release from the teeth 342 (see FIG. 3B). When this occurs, the loaded spring 318 can release. The spring 318, in turn, which is connected to the inner and outer disks 324, 322, can then cause the outer disk 322 to rotate, pulling the cannula 302 back into the body 301. In such an embodiment, the second spring 318 (see FIG. 3F) can be coiled or loaded in an opposite direction as the spring used for insertion (e.g., spring 429), thereby permitting rotation of the disk 322 and cannula 302 in the opposite direction. In some embodiments, both tabs 348a,b must be pushed simultaneously to activate the retraction mechanism, thereby preventing accidental retraction.

Another infusion device 1000 that is similar to infusion device 300 is shown in FIGS. 10A-10E. Similar to infusion device 300, however, device 1000 is intended to be used with a separate external insertion device. The infusion device 1000 includes a rotational body 1010 configured to rotate to extend cannula 1002 spirally or helically into the tissue, as described above. The infusion device 1000 further includes a fixed base plate 1024. The fixed base plate 1024 is attached to an adhesive layer 1021 for adhering the device 1000 to the skin. As shown best in FIGS. 10D and 10E, the fixed base plate 1024 includes a cannula guidance and support feature 1072 (e.g., a curved cut-out) therein, a detent lock feature 1073, and a central post 1075 that acts as a rotational axis for the rotational body 1010 and as a lumen for the passage of fluid to the cannula 1002. The detent lock feature 1073 is configured to engage when the rotational body 1010 reaches its full rotational travel distance. The fixed base plate 1024 advantageously provides rigidity to the adhesive layer 1021, cannula guidance during the insertion operation, attachment for the rotational body 1010, and cannula support during normal operation. Further, in some embodiments, the fixed base plate 1024 can include a region of alternating color and/or alpha-numeric characters that are only visible through a rotational body window at specific angular sectors indicating a binary state (e.g., ready/deployed/etc.).

Figure 9B:
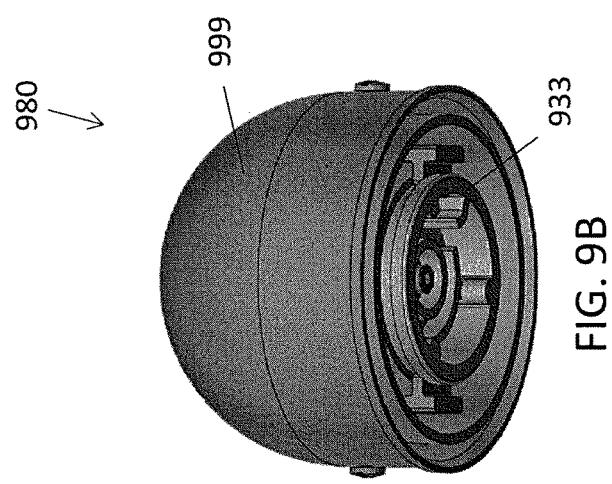
Figure 9A:
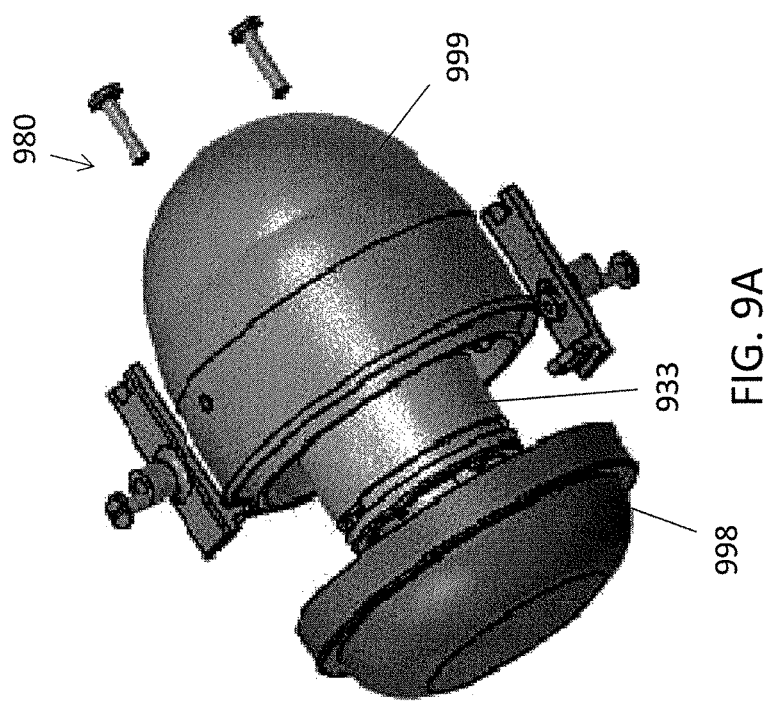
Figure 10B:
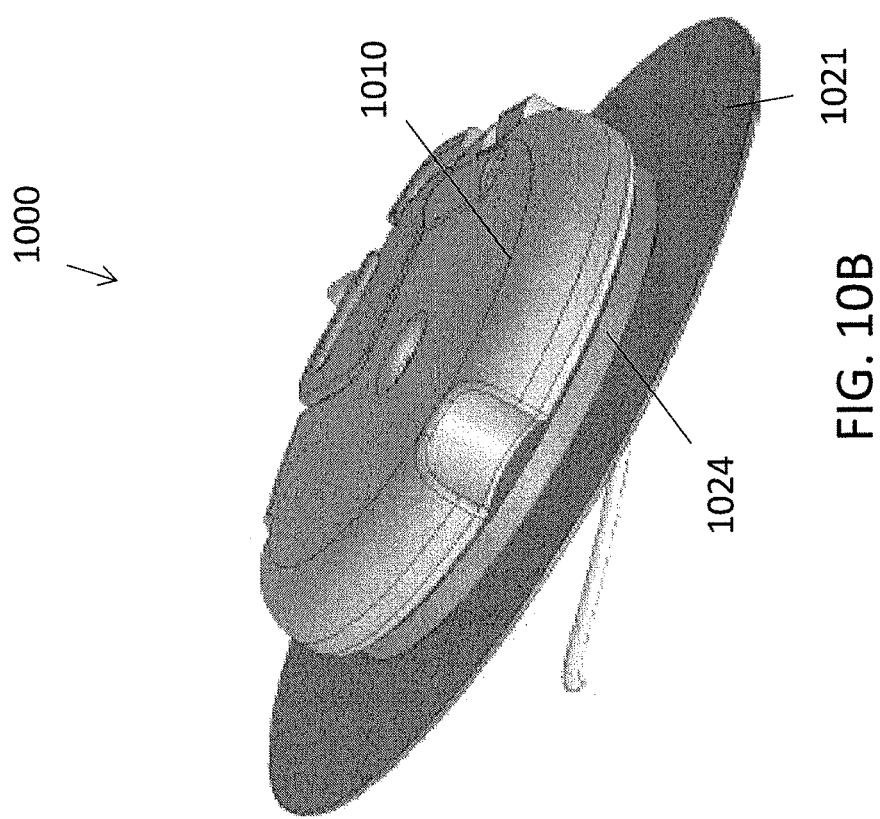
FIGS. 10A-10E show another exemplary infusion device.
Figure 10A:
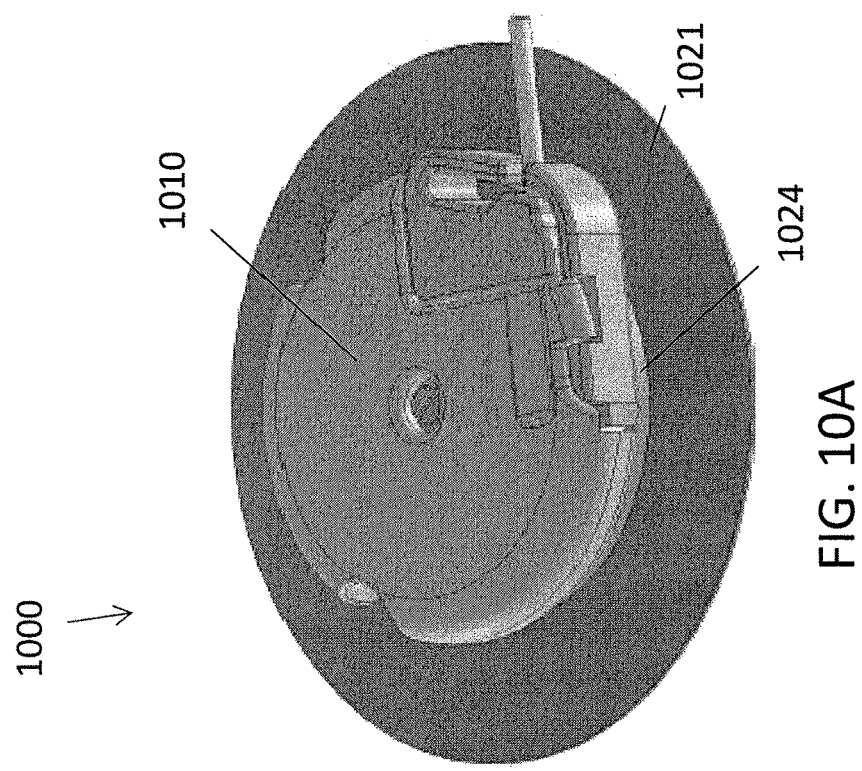
Figure 10C:
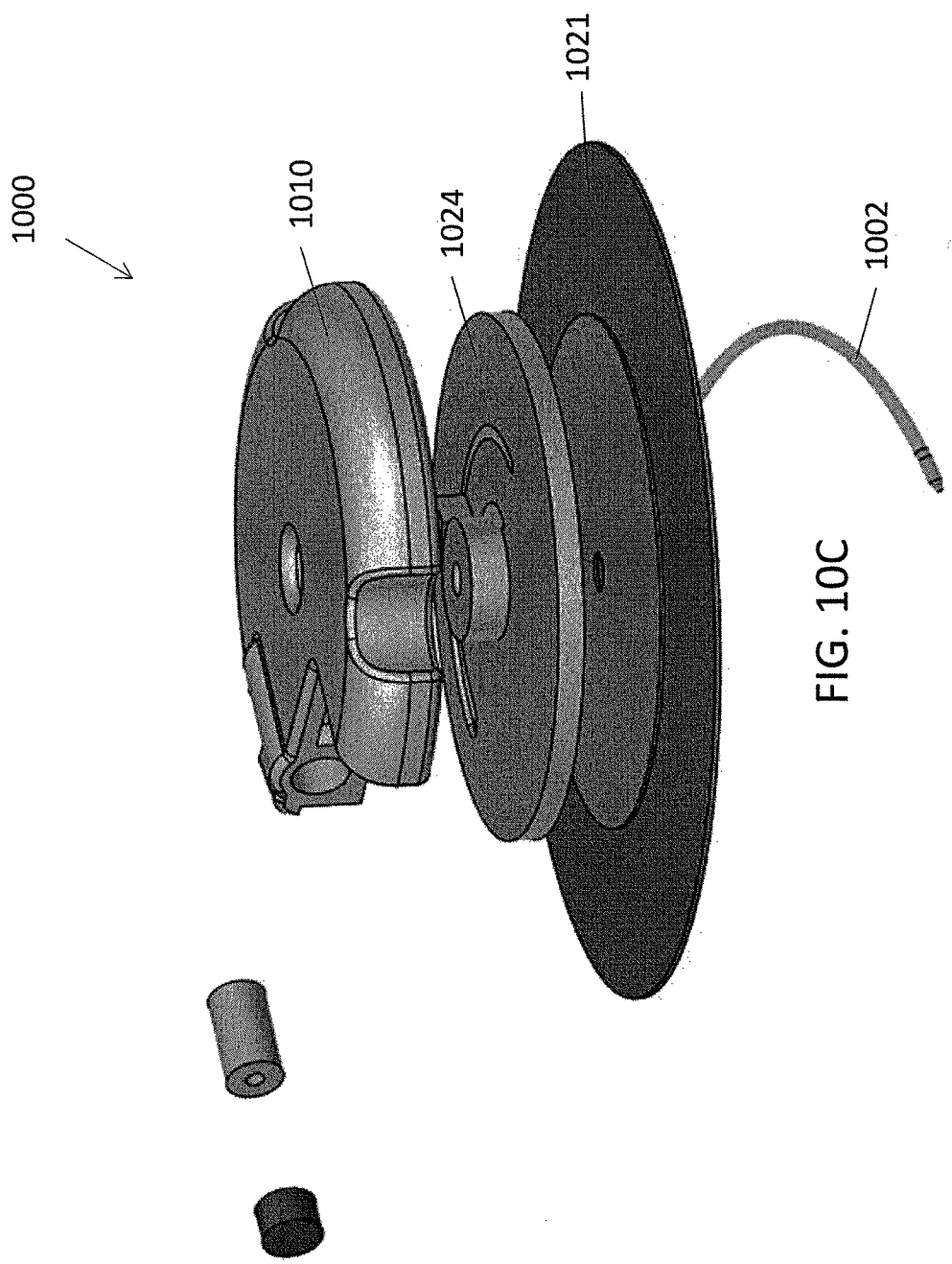
Figure 10D:
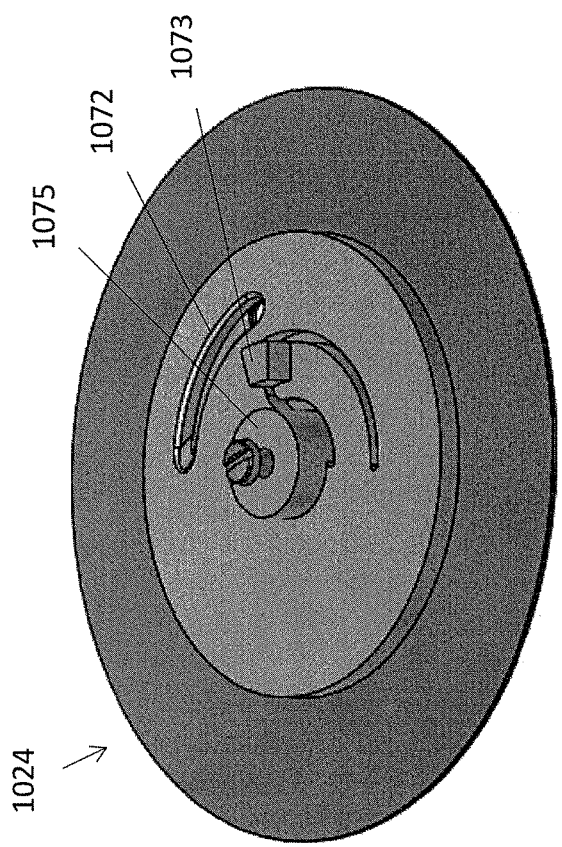
Figure 10E:
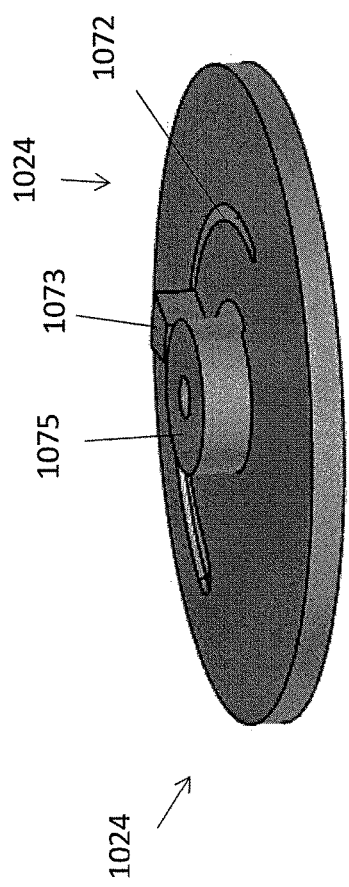

A package 980 holding a combined insertion device 933 and infusion set 900 is shown in FIGS. 9A-9C. The insertion device 933 is similar to insertion device 433, and the infusion set 900 is similar to infusion set 1000. A packaging element 999 is used to surround the insertion device 933 and infusion set 900. The packaging 999 further includes a removable cap 998.

The exterior packaging 999 of the insertion device 933 advantageously facilitates or promotes a specific user operational sequence that encourage proper use of the product and help ensure patient safety. That is, the insertion device 933 is packaged so as to encourage the tubing of the infusion device to be filled with fluid before inserting the set. As shown in FIGS. 9A-9B, the insertion device 933 thus includes external packaging 999 such that the tubing is presented to the user first (after removal of the cap 998) and the infusion set base and cannula are "behind" the tubing in the packaging 999 (i.e. can only be accessed once the tubing has been removed from the packaging 999).

The connection for tube to the pump is in an easy to reach location that presents itself to the use upon opening the packaging 999, thereby advantageously encouraging the user to grab it first when unpacking the set. Further, the tubing-to-pump connection and the portion of the tubing immediately attached to it can be positioned/held within the external packaging 999 so that the tubing to pump connection can be removed from the packaging 999 without removing the bulk of the tubing (i.e., the first foot or so of tubing comes lose with the tubing to pump connection but the rest of the tubing stays in place until intentionally removed). This allows the user to fill the tube without removing the bulk of it from the packaging 999 and without exposing the rest of the infusion device 900 until after the tubing is filled. In concert with positioning the pump connection at an easily accessible location, the tube-to-infusion set hub connection can be positioned in a less accessible location. This discourages the user from grabbing that end first and helps ensure the flow of fill tubing before inserting the infusion set.

In some embodiments, the packing 999 can further include a material thereon that changes color when droplets of insulin or diluent contact it. This advantageously helps the user know that the tubing has been filled. In some embodiments, the color changing material can be located so that when the package is resting on a flat surface, gravity directs any droplets exiting the distal end of the tubing towards the material. In an alternative embodiment, the distal portion of the tube to infusion set hub connector can contain the material that changes color when in contact with insulin or diluent.

Close-ups of an exemplary curved cannula 602 for use with any of the infusion devices described herein are shown in FIGS. 6A-6D. The curved cannula 602 can include a hollow tube 614 made of a with a soft bio-compatible material. A spiraled or helical coil 644 can extend within the tube 614 to provide reinforcement thereto. In some embodiments, the tube 614 can be made of a plastic material, such as Teflon or Nylon. In some embodiments, the coil 644 can be made of a plastic having a higher stiffness than the material of the tube 614 or can be made of a metal. In some embodiments, the tube 614 is made of metal. In some embodiments, the coil pitch can be equal to or greater than the wire diameter. In some embodiments, an extruded reinforcement can be used in place of the coil 644. The curved cannula 602 can further include a plurality of exit holes 611 at or near the distal end thereof. The holes 611 can be of a defined pattern, size, and shape (e.g., circular or elongated slots). In some embodiments, the holes 611 can vary in diameter by linear distance from the distal end of the cannula.

Figure 7A:
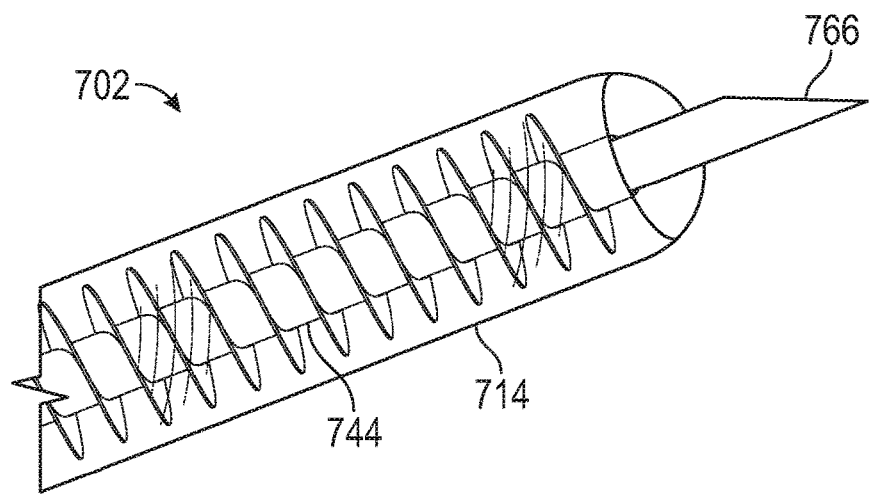
FIG. 7A shows a cannula with a stylet extending therethrough.
Figure 7B:
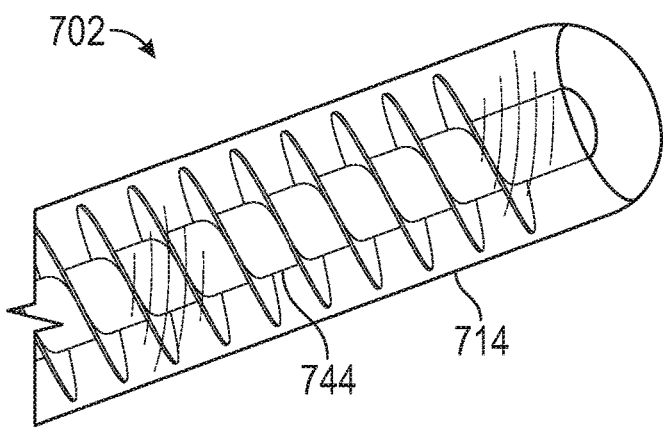
FIG. 7B shows the stylet retracted.

Referring to FIGS. 7A and 7B, in some embodiments, a solid and pointed stylet 766 can be extended coaxially through the hollow cannula 702 (including outer tube 714 and coil 744) and retracted during fluid delivery. The solid wire stylet 766 can advantageously be used to pierce the derma during use. Further, in some embodiments, the stylet 766 can have the curved shape that allows for spiral or helical insertion of the cannula 702 rather than the cannula 702 itself having the curved shape. In such an embodiment, the cannula 702 can be flexible so as to take the curved shape of the stylet 766. In some embodiments, the stylet 766 can have a sharpened distal tip that is a single bevel, has multiple bevel facets, that has a pencil-type tip, and/or a conical tip. Where a stylet, such as stylet 766, is used, the retraction mechanism described above (e.g., using a second user-activated spring), can be used only to remove the stylet, leaving the outer tube in place.

In some embodiments, the cannula can be replaced with a spirally or helically inserted body analyte sensor. For example, the body analyte sensor can be a wire assembly including chemistry components.

Further, in some embodiments, the cannula, once inserted in a spiral or helical fashion, can function as a spring member to provide three-dimensional strain relief. Thus, for example, the infusion set adhesively attached to the dermis can freely move without transferring moment energy to the cannula.

In some embodiments, the cannula is soft and semi-rigid and is coated with a lubricating element, such as a liquid, a conformal coating applied by dipping and drying, or a coating applied by gas or vapor deposition.

In some embodiments, the cannula can include an anti-inflammatory agent, an anti-biotic agent, and/or an anti-clotting agent thereon.

Figure 8:
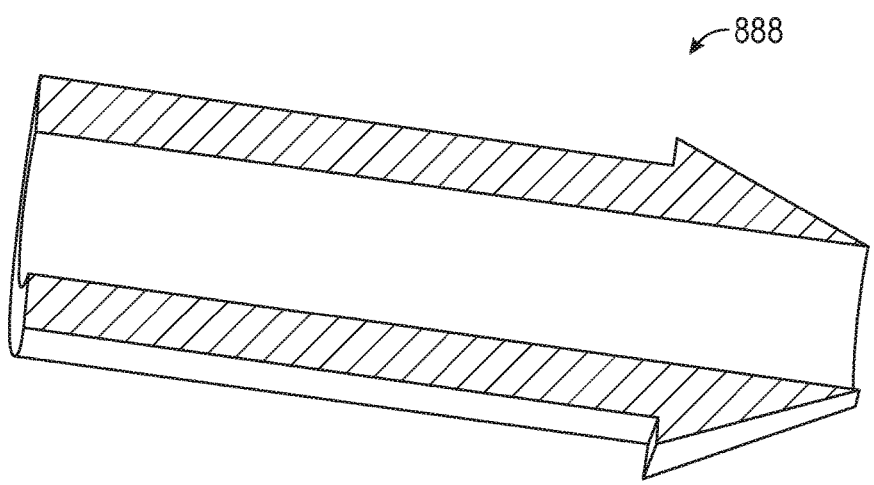
FIG. 8 shows an exemplary distal tip of a cannula.

Referring to FIG. 8, in some embodiments, the distal tip 888 of the cannula can include a molded or shaped form that promotes tissue insertion. For example, as shown in FIG. 8, the distal tip can be cone shaped. The included angle formed by opposite sides of the cone can be, for example, an angle of greater than 10° and less than 40°. Further, the cone can have an axial lumen with dimensions that support a slip-fit internal stylet.

In some embodiments, the reinforcing coil can have a fixed pitch from the proximal to the distal ends. In other embodiments, the reinforcing coil can have a variable pitch from the proximal to distal end. For example, the pitch can vary from 1:1 to 1:n over a defined region and at a defined distance from either the distal or the proximal end. The reinforcing coil can be made of stainless steel or of an engineering polymer. Further, the reinforcing coil can be a round wire or a flat wire. In some embodiments, the reinforcing coil can be injection molded. In some embodiments, the cannula can have a fixed durometer from the proximal to the distal end. In other embodiments, the cannula can have a varied durometer from the proximal to the distal end.

Although the depth control mechanism is described above with respect to an external insertion device, the depth control mechanism can also be used as part of an internal insertion mechanism, such as that described with respect to device 200.

In embodiments where a separate external insertion device (such as device 433) is used, the insertion device can be either reusable or single-use. For single use designs, the insertion device can include the cannula therein. In such an embodiment, a locking mechanism may be used that prevents the cannula from being released again.

In some embodiments, the fluid connections described herein can be attachable and detachable from the fluid source. The fluid connection can include, for example, a standard Luer lock or Minimed Paradigm connection point for connection to the pump and/or fluid reservoir. In some embodiments, the connection can include a valve, such as a septum valve, that ensures that the connection remains in a closed state until initiation of an external fluid supply physical connection. The connection can be reusable, can have only one correct insertion direction, can include features to prevent accidental disconnect, and/or can allow for connection to commercially available infusion tube sets. In some embodiments, various lengths of pump tubing may be provided (e.g. 23, 32 and 43 inch long tubing) to accommodate patient comfort and convenience.

In some embodiments, the devices described herein can have a visual indicator to show that the cannula has been fully inserted. For example, there can be a window in the hollow body to allow the user to see the indicator. The indicator can be, for example, a visual color change or a visual indicator symbol. Similarly, the devices described herein can have a visual indicator to show that the cannula has been fully retracted. This visual indicator can also be, for example, a window in the hollow body and can include a color change or visual indicator symbol For example, referring to FIG. 3D, the cover 391 of the infusion device 300 can include an indicator 375 thereon that rotates as the outer disk 322 rotates. Further, the stationary housing 301 can include a ring 374 thereon with color-coded or other visual markers 355*a*,*b*,*c*,*d*. As the outer disk 322 rotates (either to retract or insert the cannula), the indicator 375 can rotate to align with one or more of the markers 355*a*,*b*,*c*,*d* on the ring 374. For example, the first marker 355*a* can indicate that the cannula is retracted, the second marker 355*b* can indicate that the cannula is at 6 mm, the third marker 355*c* can indicate that the cannula is at 8 mm, and the fourth marker 355*d* can indicate that the cannula is at 10 mm. In FIG. 3D, the indicator 375 is at the fourth marker 355*d*, indicating that the cannula is at 10 mm.

Advantageously, the infusion delivery device and system described herein can be simple to use yet provide enhanced fluid delivery capabilities. For example, the system can allow for controlled delivery of fluid to different and precise depths, thereby permitting delivery to areas with both thin and thick layers of fat or tissue. Further, the spiral or helical insertion path of the cannula can advantageously help reduce tissue trauma from insertion relative to devices that insert the cannula at 90 degrees relative to the surface of the skin. Insertion along a long spiral or helical path also helps prevent leakage of delivered fluid, which can otherwise occur along short (e.g., 90 degree) insertion paths. The described system can therefore reduce thrombus formation, inflammation, infiltration of the wound, and encapsulation.

Advantageously, the infusion delivery devices described herein can also have a small footprint, small packaging, and/or a small profile about the skin while providing for an angled insertion path (i.e., non-90 degree insertion). For example, the height of the device (i.e., distance it extends about the skin) can be less than 0.5 inches, such as less than 0.4 inches or less than 0.3 inches. The device body can have a diameter of less than 1.5 inches, such as less than 1.2 inches, such as less than 1.0 inches. Further, the adhesive attachment patch can have a diameter of less than 1.5 inches, such as less than 1.4 inches.

Figure 12:
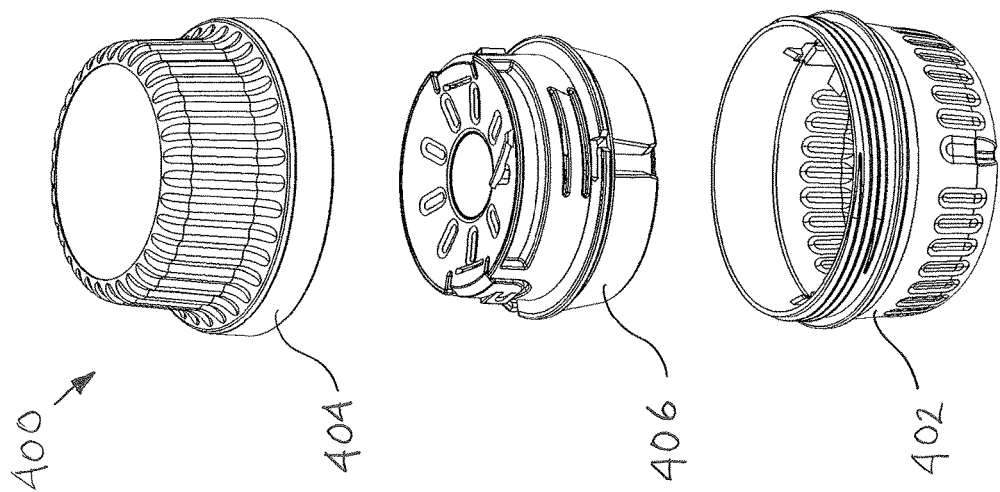
FIG. 12 is an exploded view showing the infusion system of FIG. 11 with the packaging opened and the inserter assembly removed.
Figure 11:
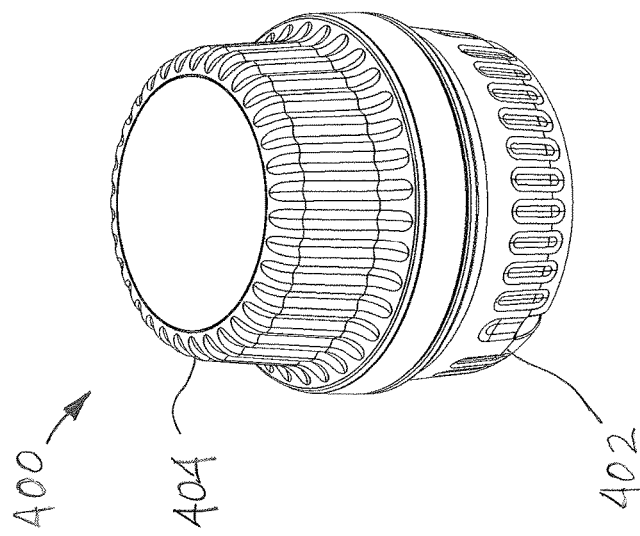
FIG. 11 is a perspective view showing the outer packaging for an exemplary transcutaneous infusion system.

Referring now to FIGS. 11-29B, another exemplary infusion system 400 will be described. System 400 is similar in construction and method of use to the previously described systems. As shown in FIG. 11, all of the working components of system 400 may be packaged within a generally cylindrical container having two cup-shaped halves that thread together. The lower portion of the container is referred to herein as jar 402 and the upper portion as lid 404. FIG. 12 shows lid 404 unscrewed and removed from jar 402, and inserter assembly 406 removed from within jar 402 where it resides until use.

Figure 13:
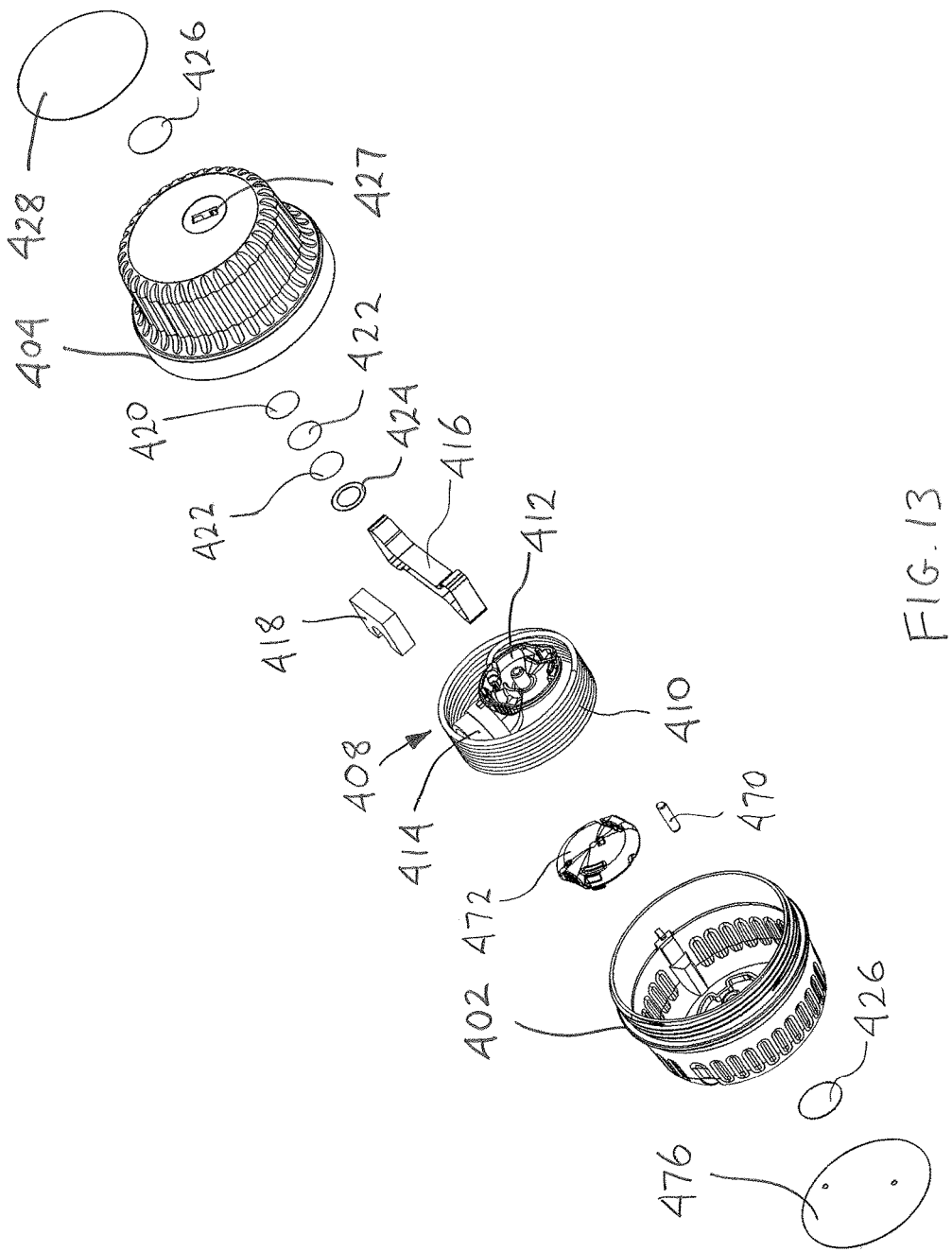
FIG. 13 is an exploded top view showing the components of the infusion system of FIG. 11 without the inserter assembly.
Figure 14:
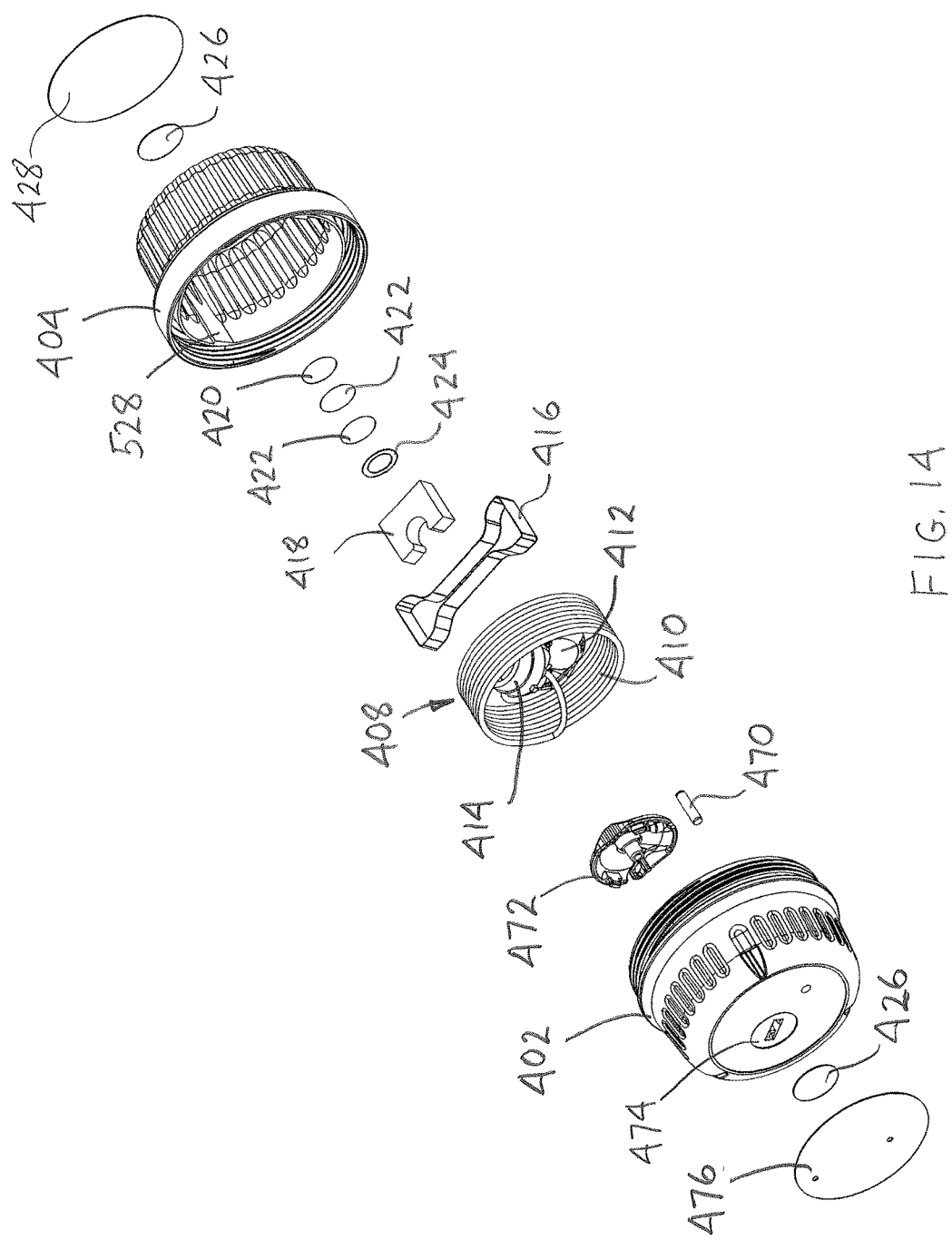
FIG. 14 is an exploded bottom view showing the components of the infusion system of FIG. 11 without the inserter assembly.

Referring to FIGS. 13 and 14, the other components of system 400, in addition to inserter assembly 406 (not shown in FIGS. 13 and 14), that are housed by jar 402 and lid 404 are shown. As with previously described embodiments, a tubing assembly 408 may be provided within the packaging in a manner that encourages the user to fill the tubing with fluid, such as insulin, before inserting a transcutaneous cannula. Tubing assembly 408 includes a coiled length of tubing 410, a connector assembly 412 located at one end of tubing 410, and a pump connector 414 located at the opposite end of tubing 410. A tubing strip 416 may be provided to help maintain tubing 410 coiled in a fashion that fits within lid 404. An adapter 418 may also be provided to receive pump connector 414 and secure it in lid 404, as will be subsequently described in more detail. This arrangement allows the user to easily remove just the pump connector end of tubing 410 for connecting it to an infusion pump reservoir for priming the tubing 410. Color dot 420, two filter membranes 422, and a gasket 424 may also be installed in the underside of lid 404 as will be subsequently described in more detail to aid the user in priming the tubing 410. In other embodiments, the tubing set may be located on top of the inserter assembly or elsewhere in the packaging rather than in lid 404.

In this exemplary embodiment, a Tyvek label 426 is used during the manufacture of system 400 to cover aperture 427 in lid 404. Aperture 427 is one of several apertures used to allow sterilization gas (such as Ethylene Oxide) to freely circulate within the closed package during product sterilization. After sterilization, label 426 is applied to lid 404 to ensure infusion system 400 remains sterile. A larger label 428 is then used to cover the top of lid 404.

Underneath removable inserter assembly 406 (not shown in FIGS. 13 and 14), an anti-rotation pin 470 may be permanently attached to the bottom of jar 402 for mating with the bottom of inserter assembly 406, as will be subsequently explained in more detail. A blank connector 472, similar to the main portion of connector assembly 412, may be releasably attached to the bottom of jar 402 underneath inserter assembly 406. Blank connector 472 may be removed from jar 402 by the user to replace connector assembly 412 on the cannula base when not in use, as will be subsequently described in more detail. Another Tyvek label 426 is used during the manufacture of system 400 to cover aperture 474 in jar 402 (used for circulation of sterilization gas, as described above), and a larger label 476 is used to cover the bottom of jar 402.

Figure 15:
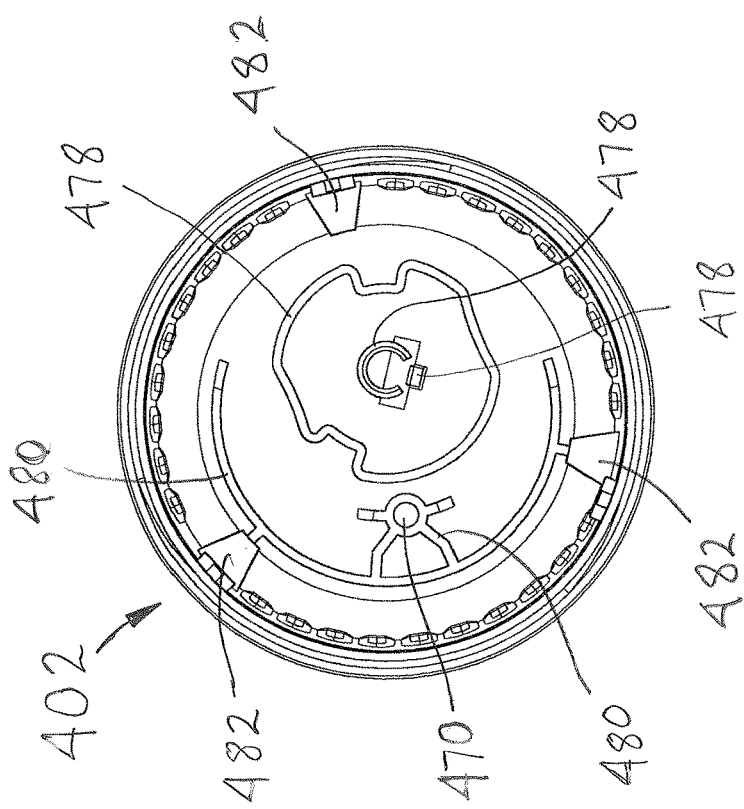
FIG. 15 is a top view showing the inside of the packaging jar of the infusion system of FIG. 11.
Figure 20:
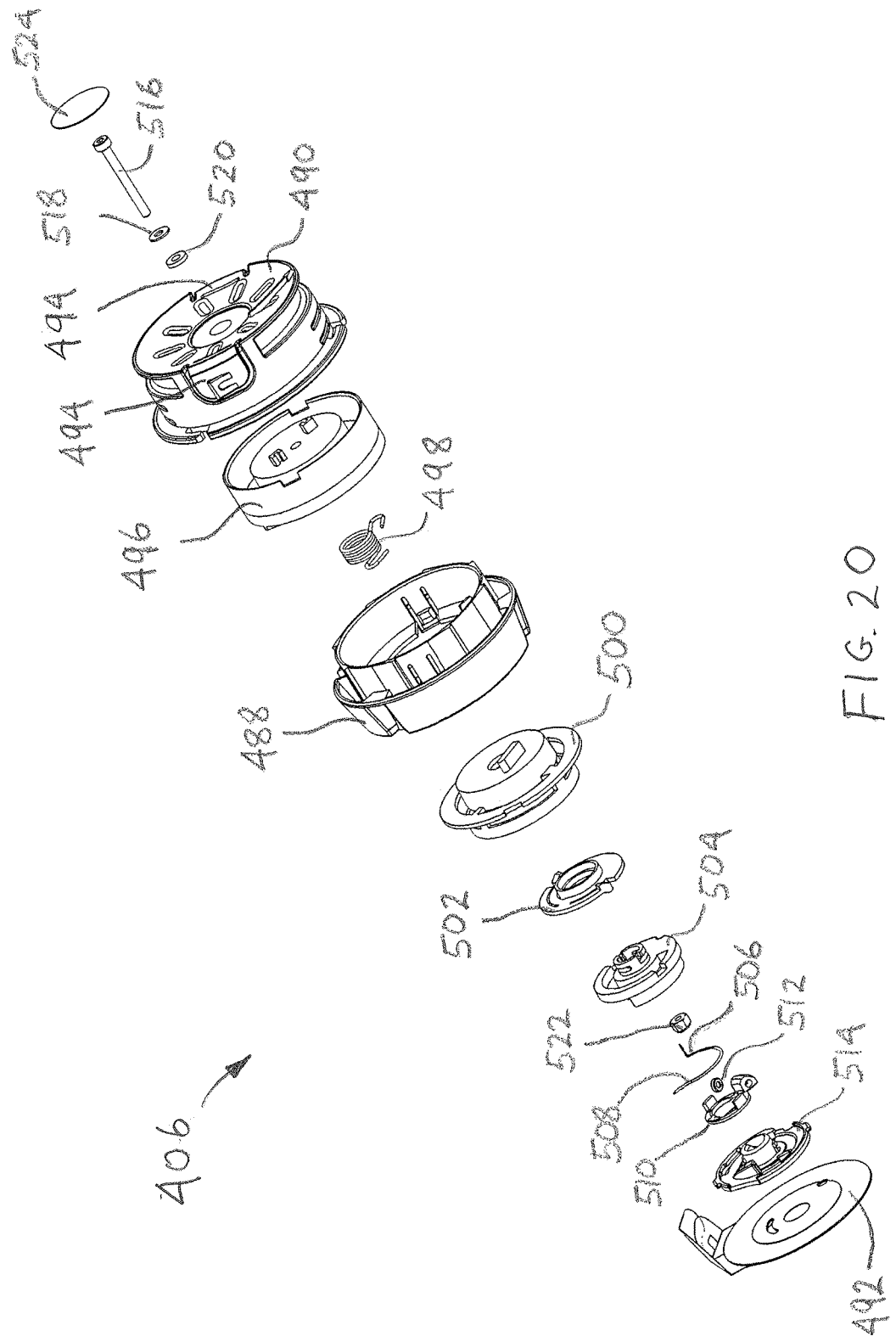
FIG. 20 is a top exploded view showing the components of the inserter assembly of the infusion system of FIG. 11.
Figure 21:
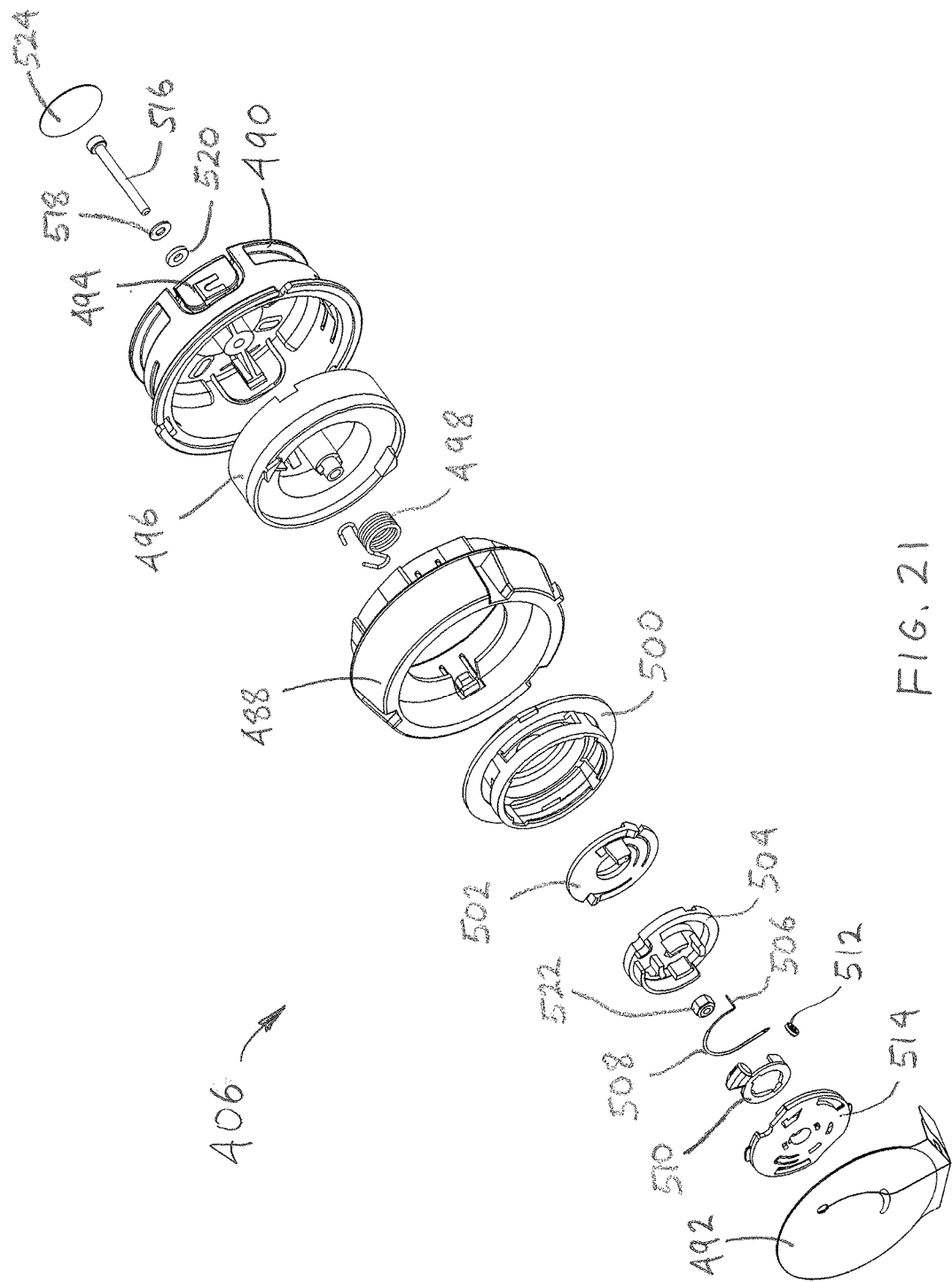
FIG. 21 is a bottom exploded view showing the components of the inserter assembly of the infusion system of FIG. 11.
Figure 22:
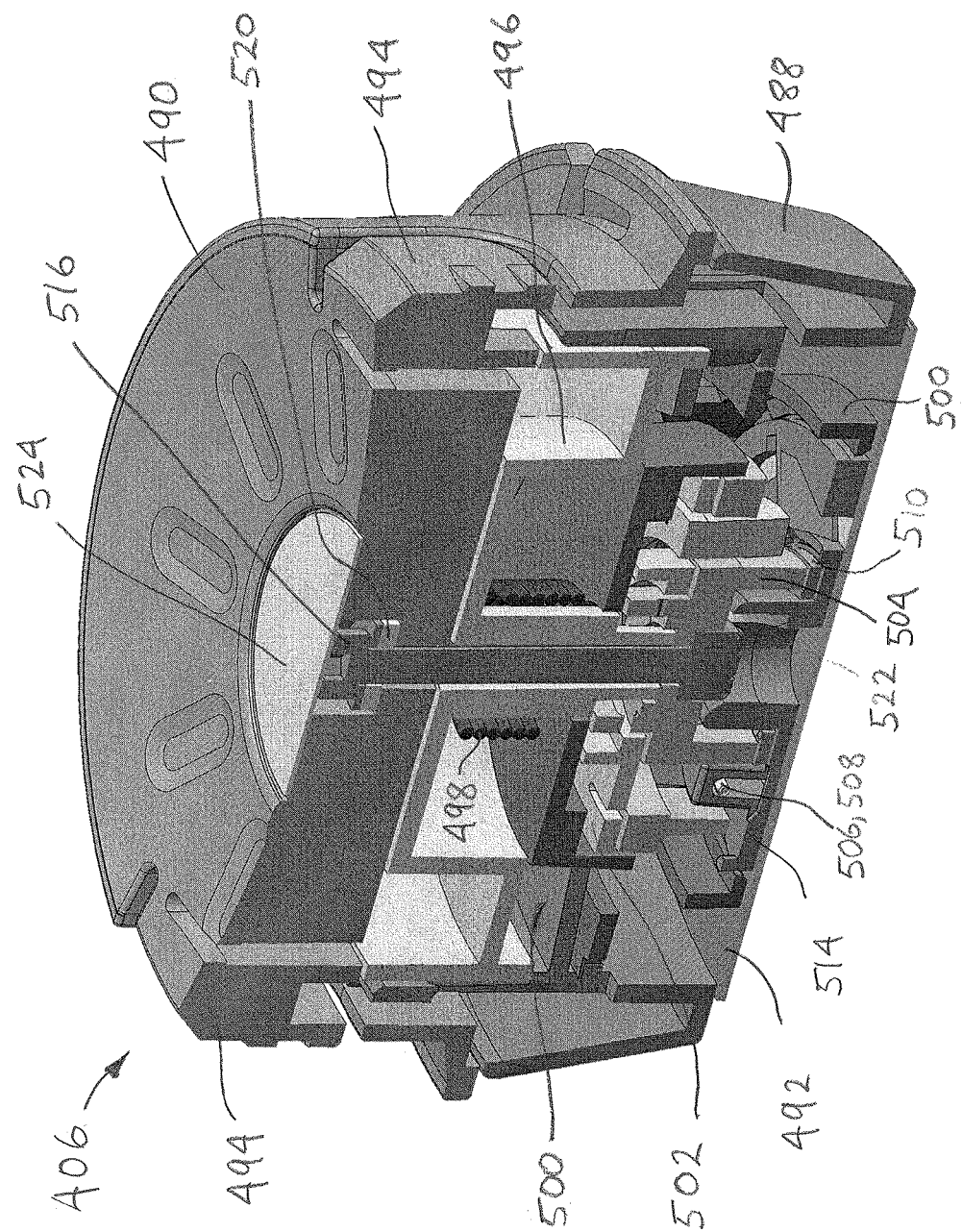
FIG. 22 is a cross-sectional view taken through the release buttons of the inserter assembly of the infusion system of FIG. 11.

Referring to FIG. 15, the inside of jar 402 is shown. The bottom inside surface of jar 402 may be provided with upwardly extending ribs 478 configured to receive blank connector 472 (shown in FIGS. 13 and 14) when not in use. In some embodiments, ribs 478 extend 1 to 2 mm above the inside bottom of jar 402. Connector 472 may snap into place over ribs 478 and may be released by pressing a release lever on connector 472. The bottom of jar 402 may also be provided with upwardly extending ribs 480 to support the bottom of inserter assembly 406 (shown in FIG. 12) above connector 472. In some embodiments, ribs 480 extend about 6 mm above the inside bottom of jar 402. A portion of ribs 480 also serve as a boss to securely hold pin 470 in place. One or more inwardly extending ridges 482 (three are shown in FIG. 15) may be provided on the inside of the vertical walls of jar 402. Ridges 482 are configured to mate with recesses 483 spaced around the lower periphery of inserter 406, as shown in FIGS. 17-19. These mating ridges 482 and recesses 483 serve to keep inserter 406 from rotating with respect to jar 402 when the inserter 406 is being charged, as will be subsequently explained in more detail.

Figure 16:
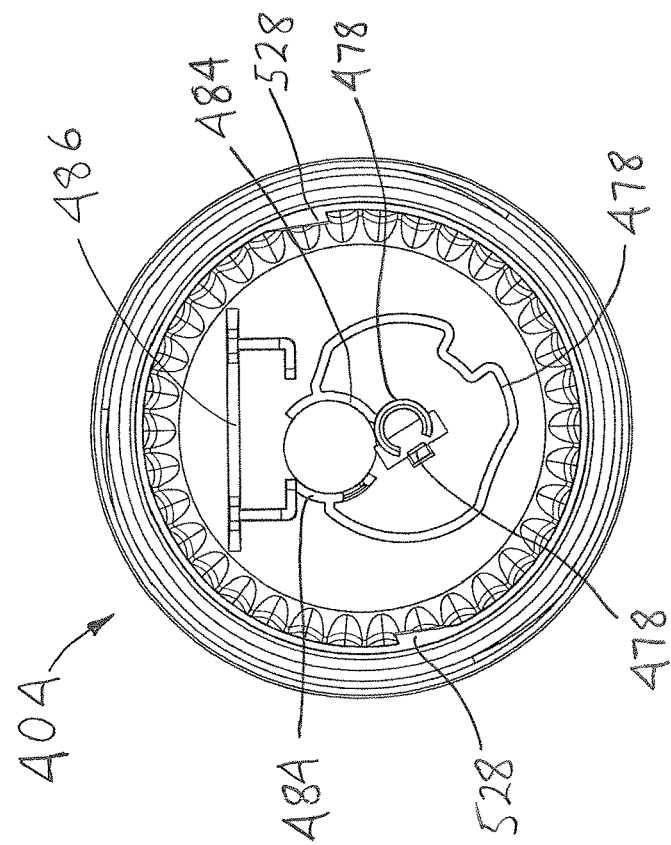
FIG. 16 is a bottom view showing the inside of the packaging lid of the infusion system of FIG. 11.

Referring to FIG. 16, the inside of lid 404 is shown. In a similar manner to the bottom of jar 402 as previously described, the bottom of lid 404 (i.e. the underside of the top surface) may be provided with downwardly extending ribs 478 configured to receive connector assembly 412 (shown in FIGS. 13 and 14) before use. In some embodiments, ribs 478 extend 1 to 2 mm below the inside bottom surface of lid 404. Connector assembly 412 may snap into place over ribs 478 and may be released by pressing a release lever on connector assembly 412. A portion of ribs 478 (shown with reference numerals 484) may be configured to hold color dot 420, two filter membranes 422, and gasket 424 (shown in FIGS. 13 and 14.) Ribs 484 hold these four circular items directly below the needle of connector assembly 412 such that when lid 404 is inverted (e.g. resting on a horizontal surface like a cup) and tubing assembly 408 is being primed, liquid drips from the needle onto the filter membranes 422 and travels down through them into color dot 420 to change its color and indicate to the user that the tubing has been primed. Alternatively, color dot 420 may start as a brightly colored piece of PVC laminating film that is not readily visible through filter membranes 422 until the membranes become wet. The bottom of lid 404 may also be provided with downwardly extending ribs 486 configured to receive adapter 418 (shown in FIGS. 13 and 14) such that pump connector 414 may be removably held in lid 404 until ready for use. In some embodiments, ribs 486 extend about 8 and 11 mm below the inside bottom of lid 404.

Referring to FIGS. 17-23, various views of the inserter assembly 406 are shown. As best seen in FIGS. 17-19, inserter assembly 406 is provided with a bottom housing 488, and a top housing 490 that can rotate in a limited manner about a vertical axis with respect to bottom housing 488 to charge/wind the inserter. An adhesive patch 492 is provided on the bottom surface of bottom housing 488 for first attaching the entire inserter assembly 406 to an insertion site of a user's skin while an infusion cannula is inserted, and then for retaining a portion of inserter assembly 406 on the insertion site. Release buttons 494 are provided on opposite sides of top housing 490 for triggering the cannula insertion sequence after the inserter assembly 406 has been charged/wound and attached to the user's skin.

Referring to FIGS. 20-23, other components of inserter assembly 406 include middle fork 496, torsion spring 498, bottom rotor 500, top rotor 502, bottom fork 504, stylet 506, cannula 508, rotor 510, septum 512, base 514, M2×20 mm hex screw 516, M2 stainless steel washer 518, M2 PTFE washer 520, M2 locknut 522 and label 524. Bottom fork 504 is provided with a hexagonal recess in the center of its bottom surface for receiving locknut 522. Screw 516 and locknut 522 captivate top housing 490, middle fork 496, bottom housing 488, bottom rotor 500, top rotor 502 and bottom fork 504 therebetween, and each component is permitted to rotate in a limited manner with respect to the other components. Torsion spring 498 is engaged between the bottom of middle fork 496 and the top of bottom rotor 500, initially in a relaxed state. When the inserter assembly 406 is charged, this single spring 498 is wound up and urges middle fork 496 in a clockwise direction (when viewed from above) relative to stationary bottom housing 488, and urges bottom rotor 500 in a counter-clockwise direction.

When inserter assembly 406 is assembled, base 514 is adhered to the top side of adhesive patch 492. Rotor 510 is rotatably retained on the center hub of base 514. Septum 512 is located in a curved circumferential channel through a radially extending wing of rotor 510. Cannula 508 is located on stylet 506 such that a short tip portion of stylet 506 extends from the distal end of cannula 508 and a proximal portion of stylet 506 including a 90 degree bend extends from the proximal end of cannula 508. The distal end of stylet 506 and cannula 508 extend from the curved circumferential channel in a clockwise direction (when viewed from above). The proximal end of cannula 508 terminates inside the curved channel in a sealed manner with the channel, while the proximal end of stylet continues through the channel and septum 512, and extends out the opposite end of the channel in the counter-clockwise direction.

Throughout the insertion process and later use of the infusion set, the adhesive patch 492, base 514, rotor 510, septum 512 and cannula 508 remain together as a unit referred to as the base assembly 526. Base assembly 526 is first releasably attached to the rest of inserter assembly 406 by way of bottom rotor 500. Once the distal end of cannula 508 is inserted through a user's skin and stylet 506 is retracted, base assembly 526 is released from inserter assembly 406 and becomes a separate unit that remains on the user's skin.

Inserter assembly 406 may be provided to a user in a sterilized and sealed state inside closed jar 402 and lid 404 (as shown by FIGS. 11 and 12), such as with a plastic seal (not shown) that can cover the junction between jar 402 and lid 404. In some embodiments, a plastic seal is not needed since an airtight seal may be formed when jar 402 and lid 404 are screwed together, but a tamper resistant label may be applied to indicate that the packaging remains unopened. In any of these shipping or storage states, torsion spring 498 is provided in a relaxed state. This prevents the plastic parts of inserter assembly 406 from sitting in a stressed state for a long period of time, which could result in the parts changing shape and not functioning consistently or reliably. According to aspects of the present disclosure, torsion spring 498 is automatically charged/wound as the packaging for inserter assembly 406 is opened. After any plastic seal is removed from around jar 402 and lid 404, lid 404 is unscrewed from jar 402. The rotation of unscrewing lid 404 simultaneously charges spring 498 by rotating top housing 490 counter-clockwise (as viewed from above) relative to bottom housing 488. As previously indicated, bottom housing 488 and jar 402 are provided with mating features that rotationally lock the two components together. The inside of vertical sidewalls of lid 404 may be provided with a pair of ratchet tabs 528 (shown in FIGS. 14 and 16) configured to engage with opposing ratchet tabs located on release buttons 494 when lid 404 is rotated in a counter-clockwise direction, so that top housing 490 is turned counter-clockwise as lid 404 is unscrewed from jar 402. In this state, middle fork 496 is rotationally locked to top housing 490 so that it also rotates with top housing 490 and lid 404. Also, anti-rotation pin 470 (shown in FIGS. 13 and 14) extends from jar 402 up into the bottom of inserter assembly 406 to prevent base 514, bottom fork 504 and bottom rotor 500 from rotating during charging. Therefore, when container lid 404 is unscrewed, top housing 490 and middle fork 496 are the only components that rotate with it, along with the top portion of torsion spring 498. Top housing 490 and middle fork 496 both rotate about 360 degrees counter-clockwise before they each lock into place and inserter assembly 406 is fully charged. Top housing 490 will not rotate again during the cannula/stylet insertion and stylet retraction process, but middle fork 496 will rotate back about 120 degrees in the clockwise direction, as will be further described below. Once lid 404 is unscrewed from jar 402 (as shown in FIG. 12), the automatically charged inserter assembly 406 may be removed from jar 402.

As previously described, once lid 404 is unscrewed from jar 402, pump connector 414 located at one end of tubing 410 (shown in FIG. 13) may be removed from lid 404, connected to an infusion pump, and tubing 410 may be primed with fluid from the pump reservoir. After the charged inserter assembly 406 is removed from jar 402, the lining of adhesive patch 492 (shown in FIG. 18) may be removed to expose the adhesive. The bottom of inserter assembly 406 may then be applied to an insertion site on the skin of the user and held in place with adhesive patch 492.

Still referring to FIGS. 20-23, once the charged insertion assembly 406 has been applied to the skin of a patient, it may be activated to automatically insert the enclosed cannula under the skin. In this exemplary embodiment, both release buttons 494 are pushed inwardly to activate the firing sequence. The release buttons 494 rotationally unlock middle fork 496 from top housing 490, allowing torsion spring 498 to drive middle fork 496 about 120 degrees in the clockwise direction. Middle fork 496 is provided with radially protruding features on a central hub (best seen in FIG. 21) that allow it to simultaneously drive bottom fork 504 about 120 degrees in the clockwise direction. Bottom fork 504 in turn drives rotor 510 clockwise, causing stylet 506 and cannula 508 to be driven into the user's skin in a helical fashion, as will be subsequently described in more detail. Both middle fork 496 and bottom fork 504 stop rotating and are locked in place.

When bottom fork 504 reaches the end of its clockwise travel (marking the end of the stylet and cannula insertion cycle), tabs on the top of middle fork 496 force arms in bottom housing 488 to disengage bottom rotor 500 from its locked position, initiating the start of the stylet retraction cycle. At this point, the top of torsion spring 498 has been wound about 360 degrees in counter-clockwise direction by the charging cycle and unwound about 120 degree in the clockwise direction by the stylet and cannula insertion cycle. This leaves enough stored energy in spring 498 to drive the bottom rotor 500 about 240 degrees in the counter-clockwise direction during the stylet retraction cycle. Bottom rotor 500 drives top rotor 502 which in turn drives stylet 506 about 240 degrees in the counter-clockwise direction, which removes stylet 506 from cannula 508 and withdraws stylet 506 out of sight into the inserter, as will be subsequently described in more detail. Once bottom rotor 500 reaches the end of its counter-clockwise travel, locking features on bottom rotor 500 release base 514 so that inserter assembly 406 can be removed from the user, leaving adhesive patch 492, base 514, rotor 510 and cannula 508 intact on the user.

As disclosed above, once release buttons 494 are pressed, the aforementioned components cooperate to automatically insert cannula 508 and stylet 506 through the skin in a clockwise direction, then retract stylet 506 in a counter-clockwise direction, and then release the base assembly from the inserter assembly without further interaction from the user. A single spring 498 provides all of the energy required for this automatic insertion and retraction process. Before, during and after this process, the user is never able to see or touch stylet 506 or cannula 508, providing further safety and comfort to the user. In other embodiments, only one release button 494 may be provided, or if multiple release buttons are provided only one needs to be pressed to automatically activate the insertion, retraction and release cycles. This may be referred to as a single "trigger event", regardless of how many buttons need to be pushed.

Figure 24A:
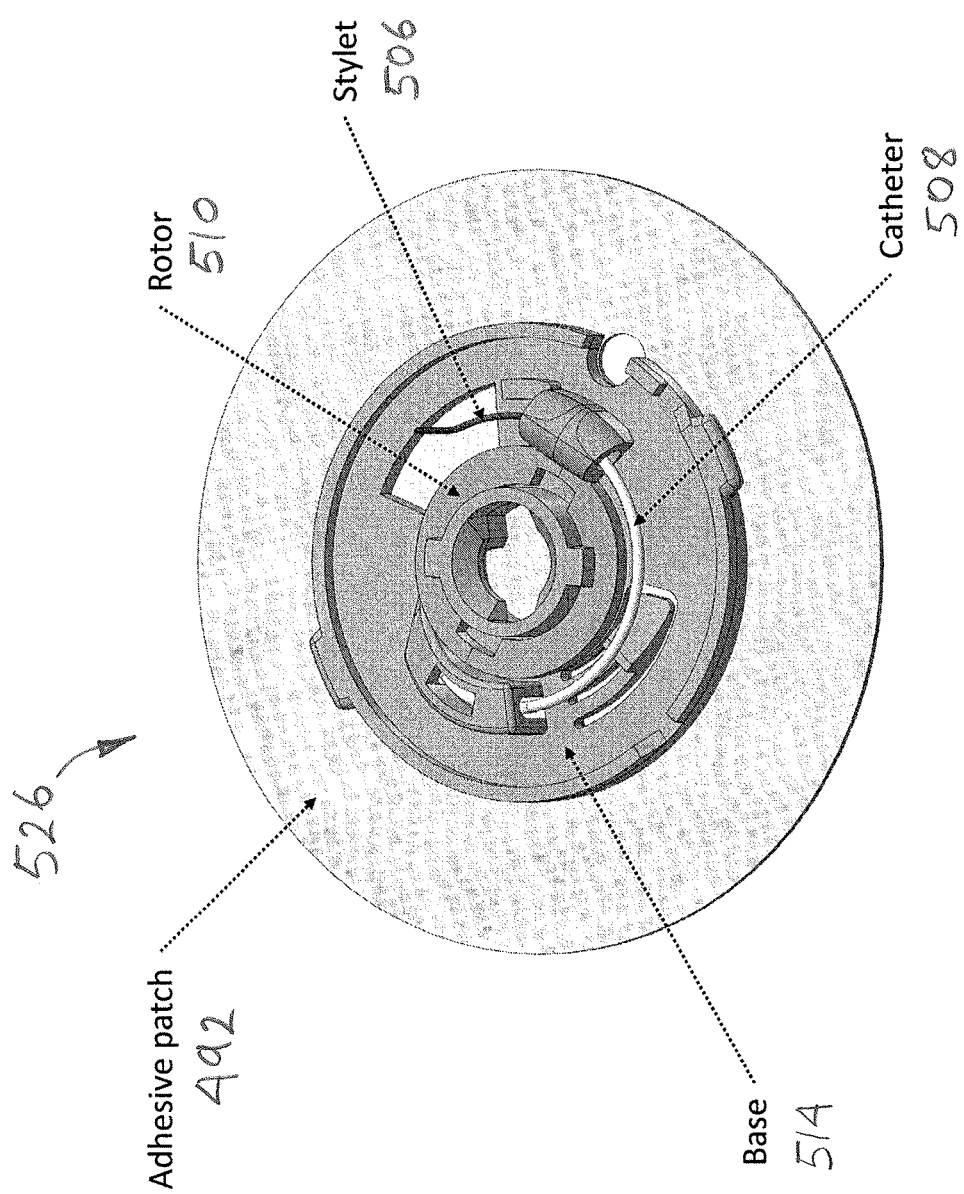
FIGS. 24A-24P are a series of views of the base assembly of the infusion system of FIG. 11 showing a sequence of events starting with the base assembly first being attached to the user's skin and through use of the infusion system.
Figure 24C:
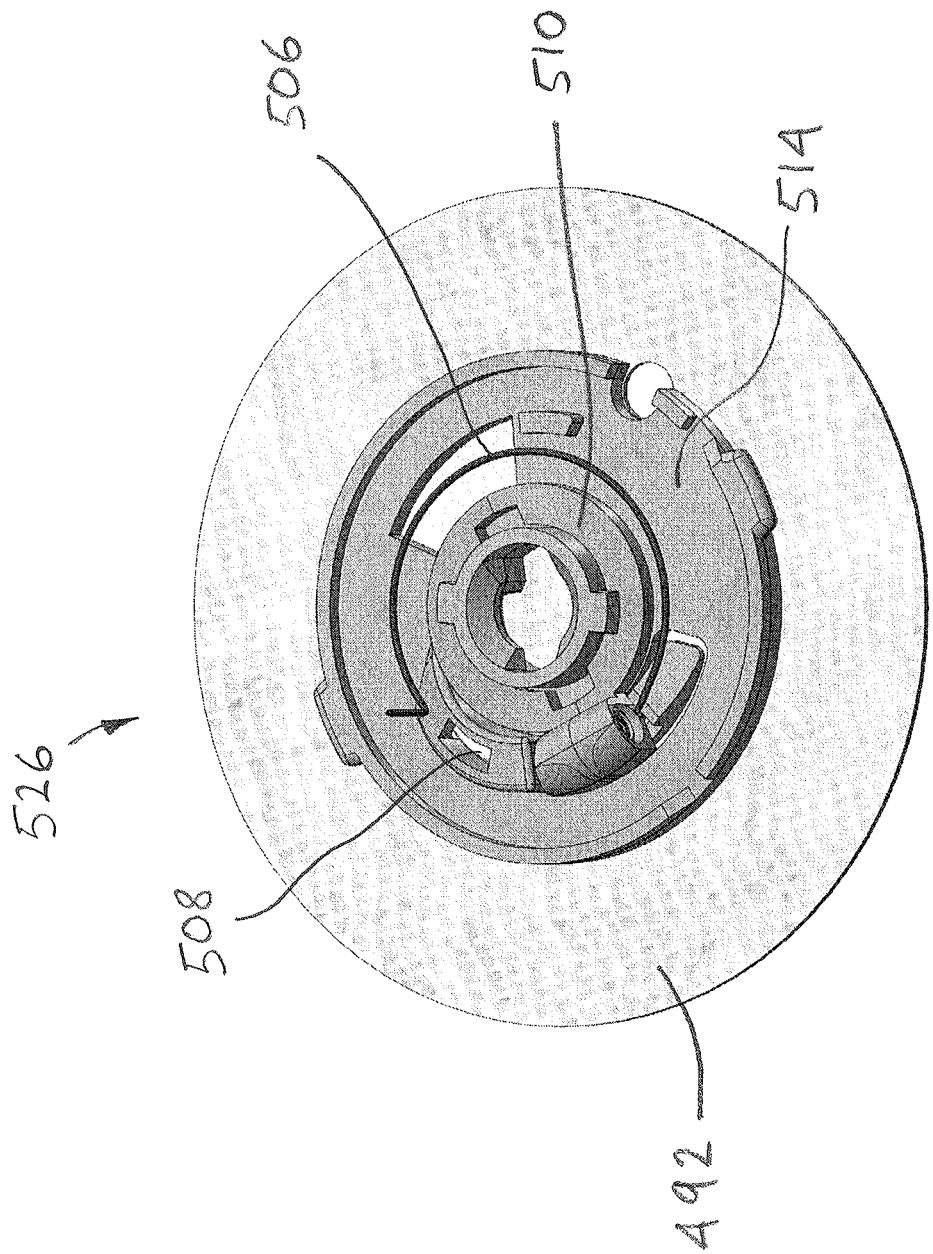
Figure 24E:
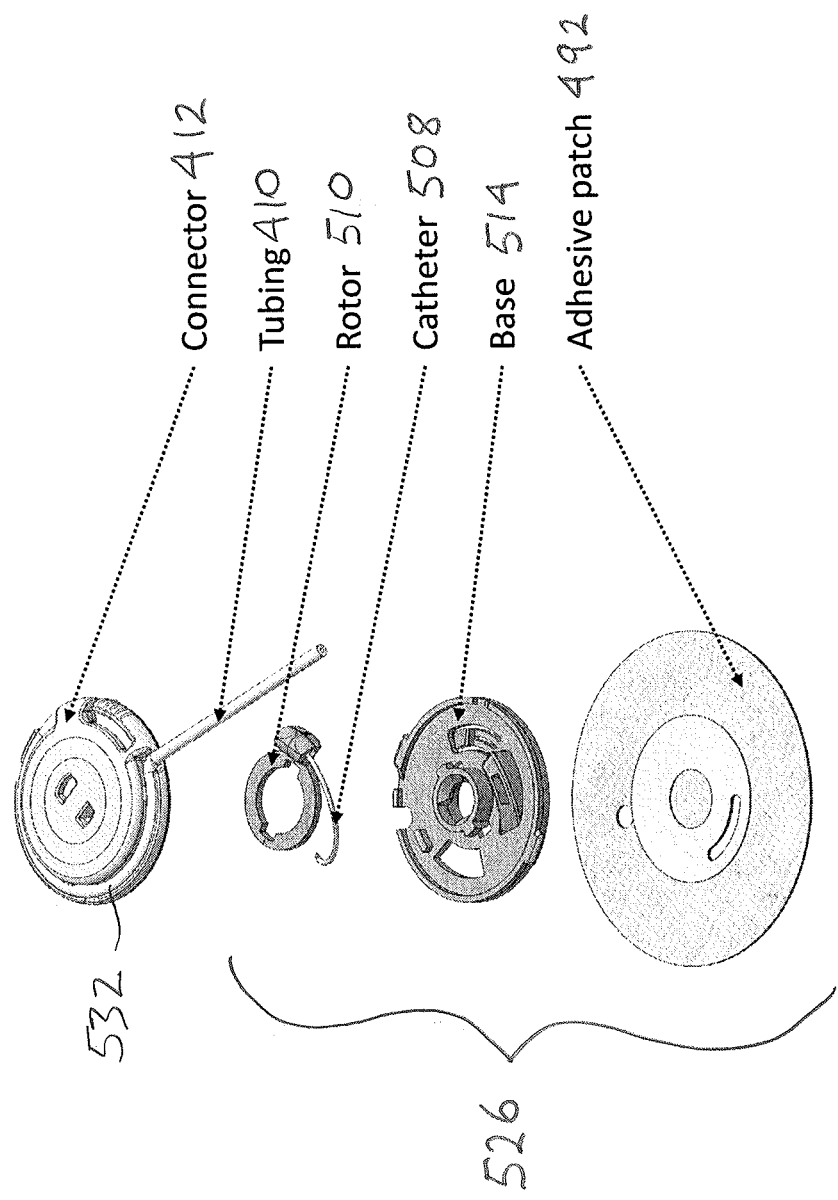
Figure 24F:
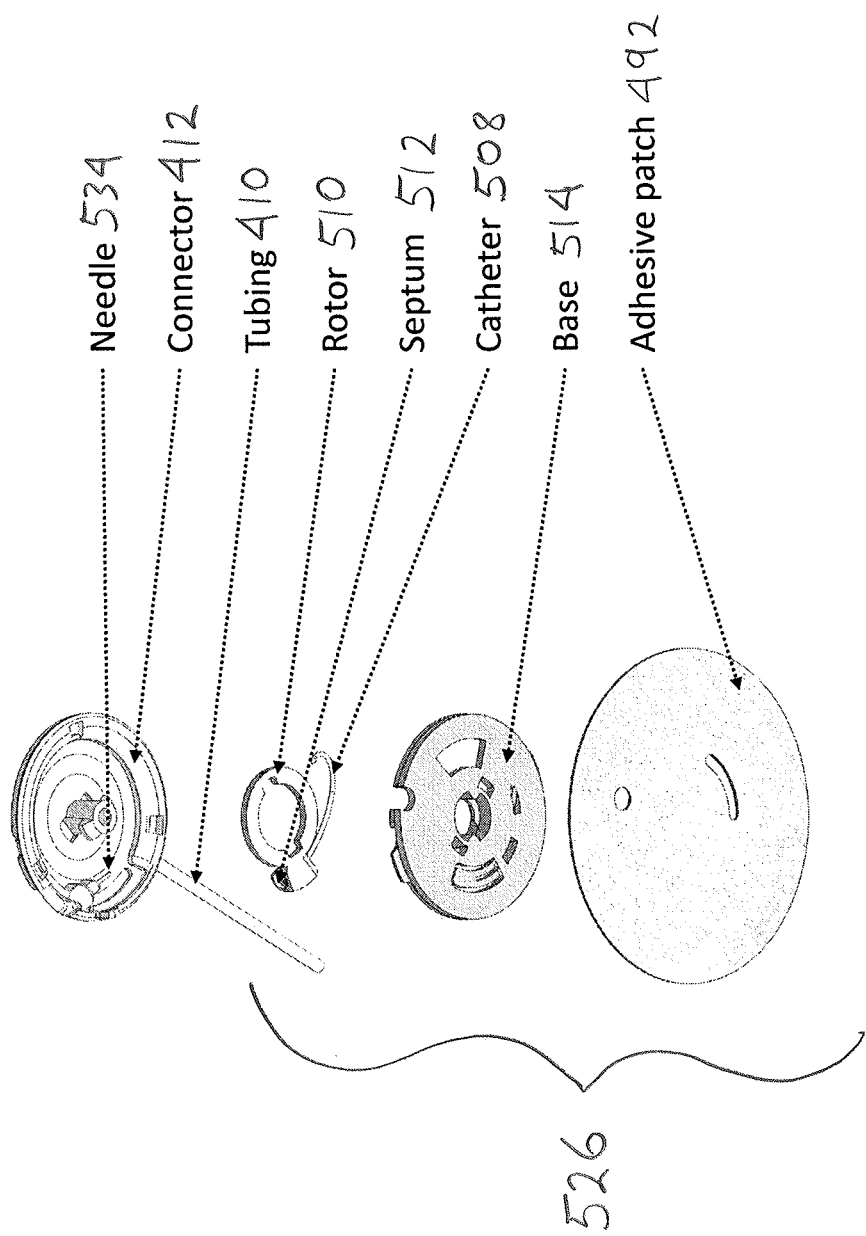
Figure 24H:
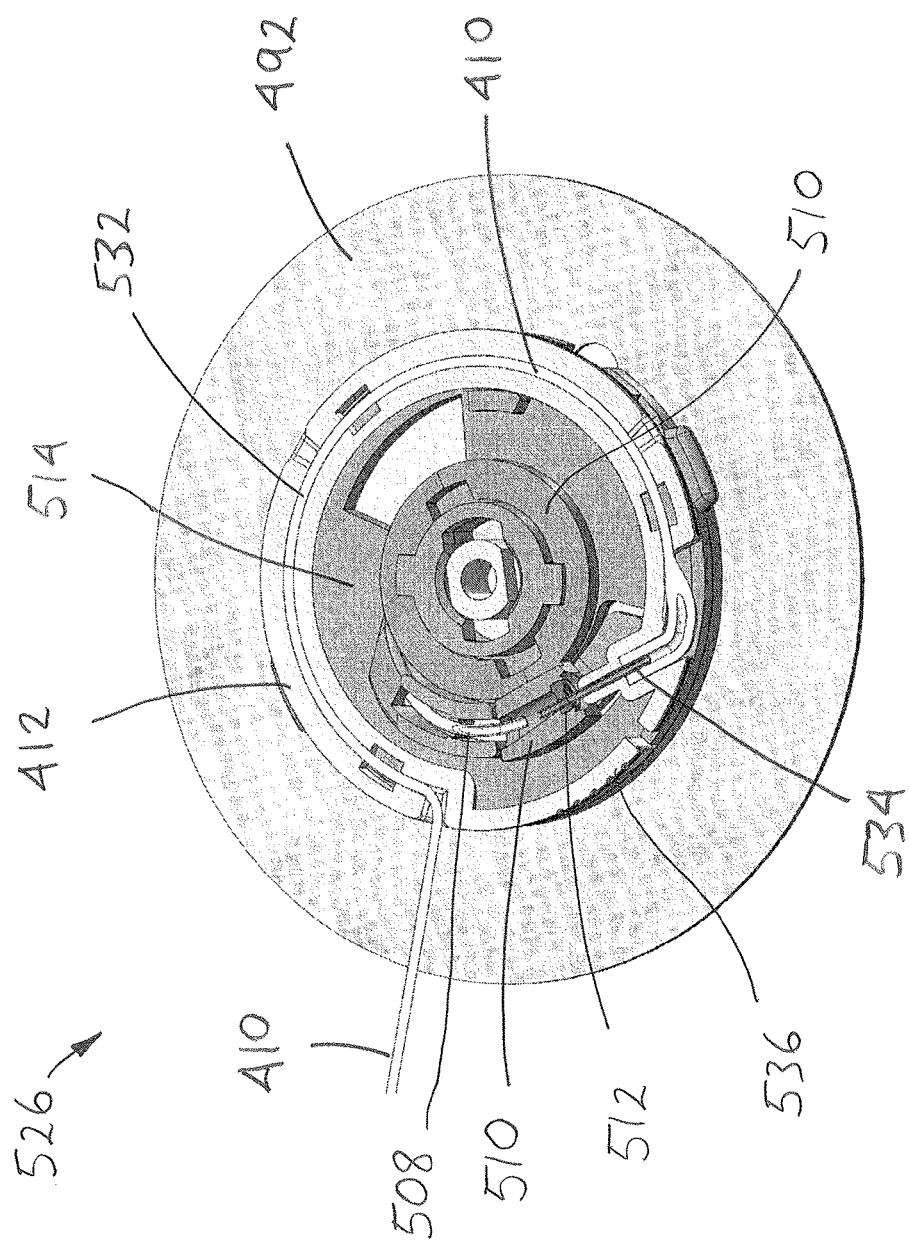
Figure 24K:
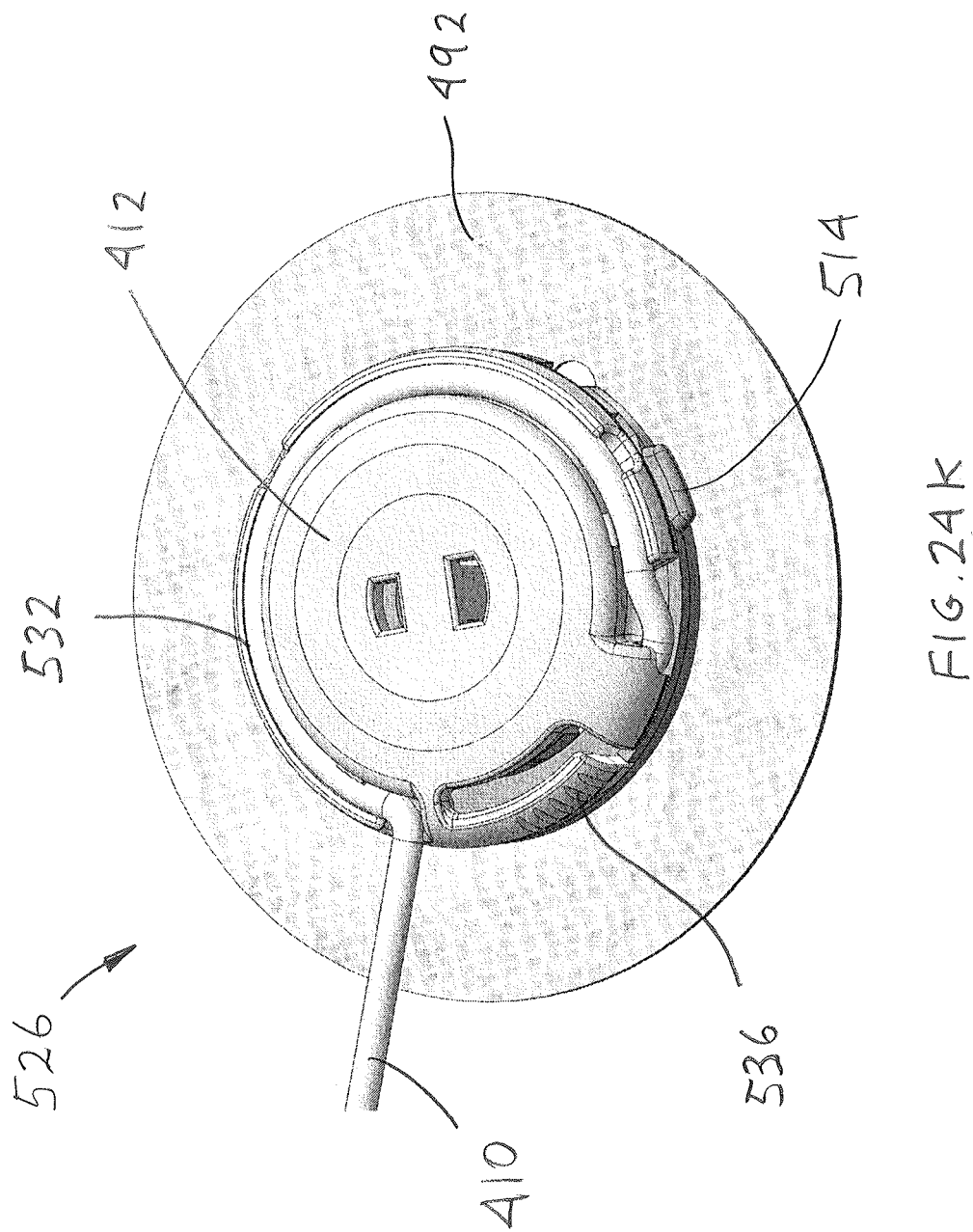
Figure 24M:
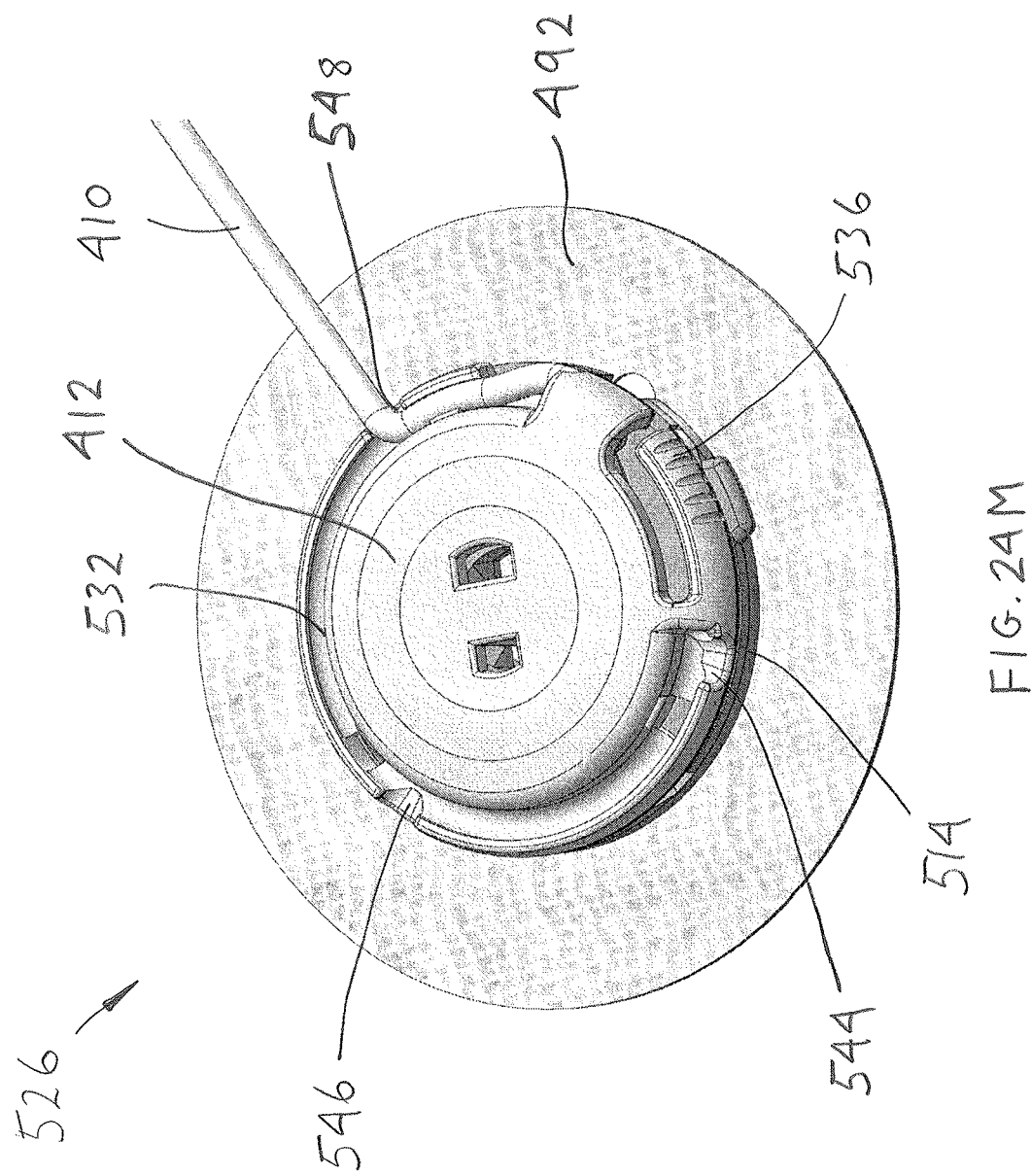
Figure 24N:
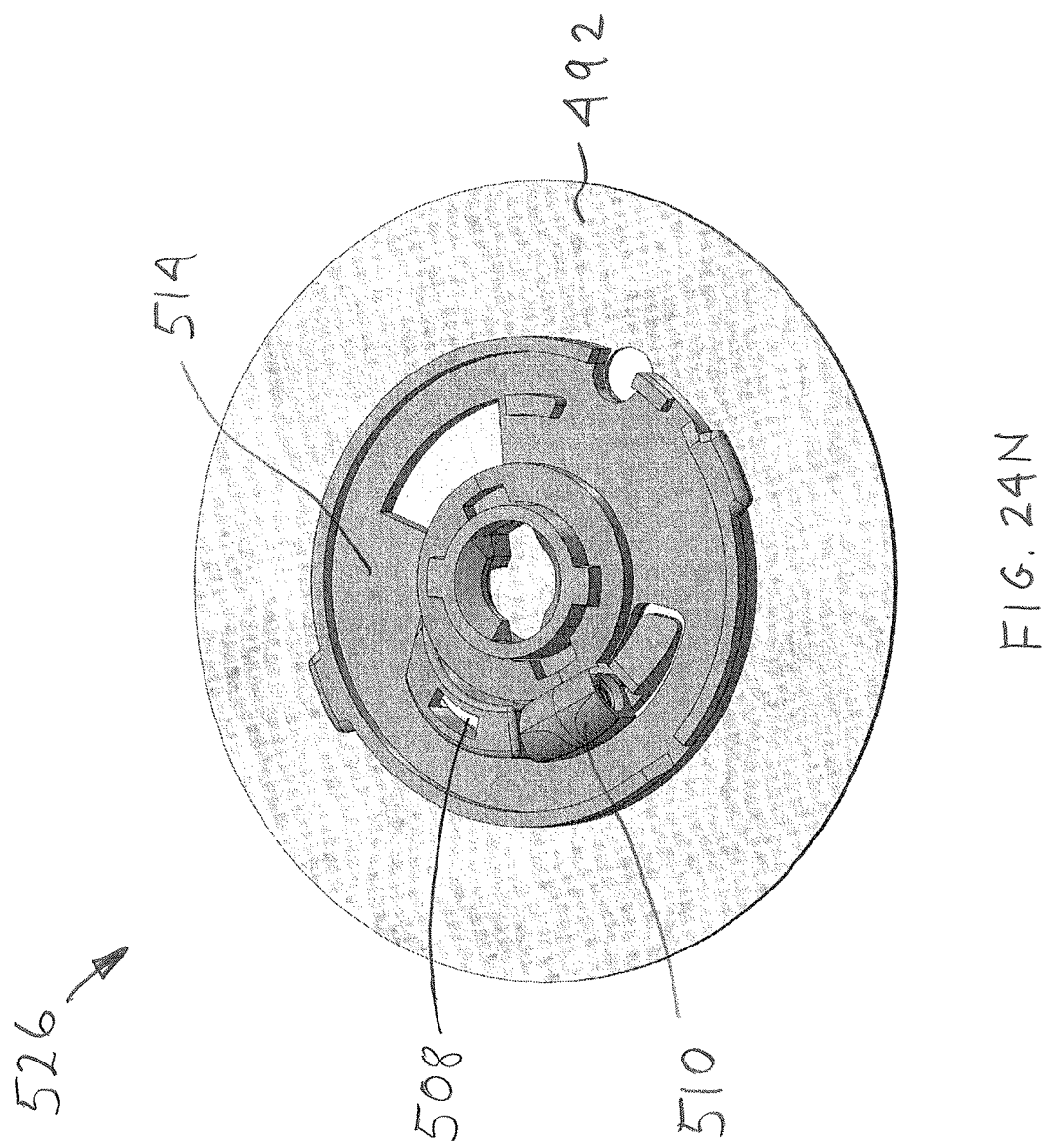
Figure 24P:
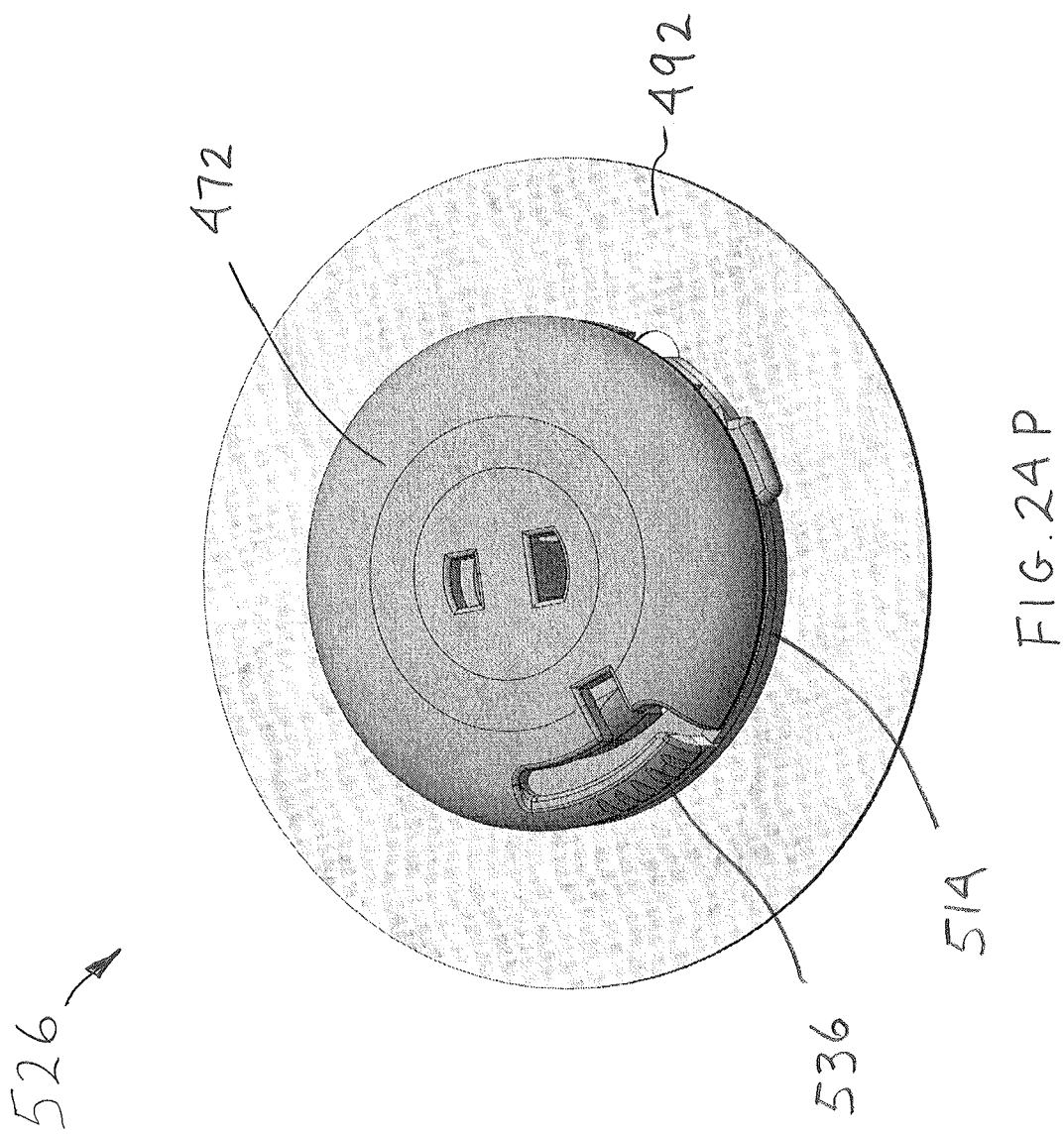

Referring to FIGS. 24A-24P, the steps of applying base 514 to a user, automatically inserting cannula 508, and connecting the primed infusion pump tubing to base 514 are shown. The steps shown in FIGS. 24A-24D correspond to some of the steps described above in reference to FIGS. 20-23, but focus on what is occurring with the components in base assembly 526 rather than the components in the rest of inserter assembly 406. FIG. 24A shows base assembly 526 in a ready to deploy state, when inserter assembly 406 is first applied to the user's skin. The rest of inserter assembly 406 (shown in FIGS. 20-23) is still attached to base assembly 526 at this point but is removed from FIGS. 24A-24D for clarity. As previously indicated, base assembly 526 includes adhesive patch 492, base 514, rotor 510, septum 512 and cannula or catheter 508.

Referring to FIG. 24A, when the inserter is in the ready to deploy state as shown, cannula 508 is mounted over stylet 506, with the pointed distal tip (not shown) of stylet 506 protruding slightly from the distal end of cannula 508. The proximal end of cannula 508 terminates inside the circumferential channel of rotor 510, while the proximal bent end of stylet 506 extends through septum 512 (not shown) and out through the opposite end of the channel. At this stage, the distal ends of stylet 506 and cannula 508 are retracted within base 514 rather than extending through adhesive patch 492.

Referring to FIG. 24B, base assembly 526 is shown with the distal ends (not shown) of stylet 506 and cannula 508 deployed downwardly into the skin (not shown but located beneath adhesive patch 492.) Comparing FIG. 24B with FIG. 24A, it can be seen that rotor 510, catheter 508 and stylet 506 have been rotated together about 120 degrees in the clockwise direction, as previously described in reference to FIGS. 20-23. Stylet 506 and cannula 508 follow a generally helical path through and beneath the skin due to the stylet 506 and/or the cannula 508 having been preformed in a helical shape and due to the downwardly sloped cam surface 530 of base 514 that guides stylet 506 and cannula 508 down into the skin. In this exemplary embodiment, stylet 506 and cam surface 530 each have a 30 degree angle relative to the surface of the skin, and stylet 506 has a constant nominal radius of 7.15 mm.

Referring to FIG. 24C, base assembly 526 is shown with stylet 506 rotated back alone and retracted from cannula 508 and from the channel in rotor 510. As previously described in reference to FIGS. 20-23, stylet 506 is retracted about 240 degrees in the counter-clockwise direction.

Referring to FIG. 24D, base assembly 526 is shown with stylet 506 removed completely, as occurs when base 514 is released from the rest of inserter assembly 406 and the inserter is removed with stylet 506 retracted within it.

Referring to FIGS. 24E and 24F, an exploded top view and exploded bottom view, respectively, show details of connector assembly 412 before it is mated with base assembly 526. As shown in FIG. 24E, tubing 410 enters radially into a groove 532 that extends around the periphery of the top surface of connector assembly 412. Groove 532 and tubing 410 extend about 270 degrees around connector assembly 412 before tubing 410 passes into the interior of connector assembly 412. As shown in FIG. 24F, when the tubing passes into the interior of connector assembly 412, it connects with needle 534 which continues to extend tangentially into the interior of connector assembly 412.

Referring to FIG. 24G, a cross-section view shows connector assembly 412 placed onto base assembly 526 in an unlocked position. This view more clearly shows tubing 410 extending along periphery groove 532, and an enlarged portion formed on the distal end of tubing 410 for receiving the proximal end of needle 534. As shown, connector assembly 412 includes an internal boss configured to hold a middle portion of needle 534 in a controlled orientation such that the distal end of needle 534 can pass through septum 512 when the connector assembly 412 is rotated clockwise with respect to base assembly 526.

Referring to FIG. 24H, a cross-section view similar to FIG. 24G is shown, but with connector assembly 412 rotated from the unlocked position to the locked position. To move to the locked position, connector assembly 412 is rotated 90 degrees clockwise relative to base assembly 526. As connector assembly 412 is rotated, the distal end of needle 534 pierces septum 512 to enter the channel of rotor 510, such that it is in fluid communication with the proximal end of cannula 508 as shown. Locking arm 536 prevents connector assembly 412 from rotating back to the unlocked position until it is pressed radially inward.

Referring to FIG. 24I, a bottom view of FIG. 24G shows connector assembly 412 coupled with base assembly 526 in an unlocked position (with adhesive patch 492 removed for clarity.) A center post which depends from the bottom of connector 412 can be seen protruding through an aperture in the center of base 514. Radially extending tabs 538 and 540 may be provided on this center post of base 514, which pass through mating apertures in base 514 when connector 412 is aligned with it in the unlocked position. As connector 412 is rotated towards the locked position (counter-clockwise as viewed from below in FIG. 24I), tabs 538 and 540 travel along ramps 542 to retain connector 412 on base 514.

Referring to FIG. 24J, a top view similar to FIG. 24G but not in cross-section shows connector assembly 412 placed onto base assembly 526 in an unlocked position.

Referring to FIG. 24K, a top view similar to FIG. 24H but not in cross-section shows connector assembly 412 rotated 90 degrees clockwise with respect to base assembly 526 into a locked position.

Referring to FIG. 24L, a top view similar to FIG. 24K is shown. This figure illustrates that peripheral groove 532 of connector assembly 412 may be provided with multiple tubing exit points. In this exemplary embodiment, three tubing exit points 544, 546 and 548 are provided. In other embodiments, a greater or lesser number of tubing exit points may be provided. The user may choose to leave tubing 410 in exit point 544, as shown in FIG. 24K. If instead the user prefers that tubing 410 extends in a different direction from connector 412 toward the infusion pump (not shown), the user may lift a portion of tubing 410 out of peripheral groove 532 and lock the tubing into exit point 546, or lock the tubing into exit point 548 as shown. In embodiments with or without these multiple tubing exit points, an indicator may be provided on inserter assembly 406, such as the arrow shown on top of inserter assembly 406 in FIG. 17, to indicate to the user before applying the inserter assembly to the skin which direction the tubing will be exiting the base assembly 526.

In the state shown in FIG. 24K or 24L, the infusion set is ready to use and the infusion pump may be activated.

Referring to FIG. 24M, a top view similar to FIG. 24L is shown. In this view, release arm 536 has been pressed inwardly and connector assembly 412 has been rotated 90 degrees counter-clockwise relative to base assembly 526 into the unlocked position. In this position, tubing 410 is removed from fluid communication with cannula 508 (not shown but still inserted under the user's skin), and connector assembly 412 may be removed from base 514.

Referring to FIG. 24N, this top view shows base assembly 526 remaining on the user's skin after connector assembly 412 has been unlocked and removed.

Referring to FIG. 24O, this top view shows blank connector 472 placed onto base assembly 526 in an unlocked position. A user may wish to temporarily replace connector assembly 412 with blank connector 472 to protect base assembly 526 when not in use, such as when the infusion pump and tubing is removed for showering. As previously described in reference to FIGS. 13-15, blank connector 472 may be stored in jar 402 until needed.

Referring to FIG. 24P, a top view similar to FIG. 24O. This view shows blank connector 472 after it has been rotated 90 degrees clockwise relative to base assembly 526 into the locked position. To remove blank connector 472, release arm 536 is pressed in and blank connector is rotated 90 degree counter-clockwise. When the user is ready to remove base assembly 526 completely, adhesive patch 492 is peeled back from the user's skin and pulled off, taking the cannula and other components with it.

In some embodiments, inserter assembly 406 has a maximum diameter no greater than 2.25 inches and a height no greater than 1.5 inches. In some embodiments, when connector assembly 412 is coupled to base 514, the combined assembly has a maximum diameter no greater than 1.25 inches and a height above the user's skin no greater than 0.3 inches.

Figure 25A:
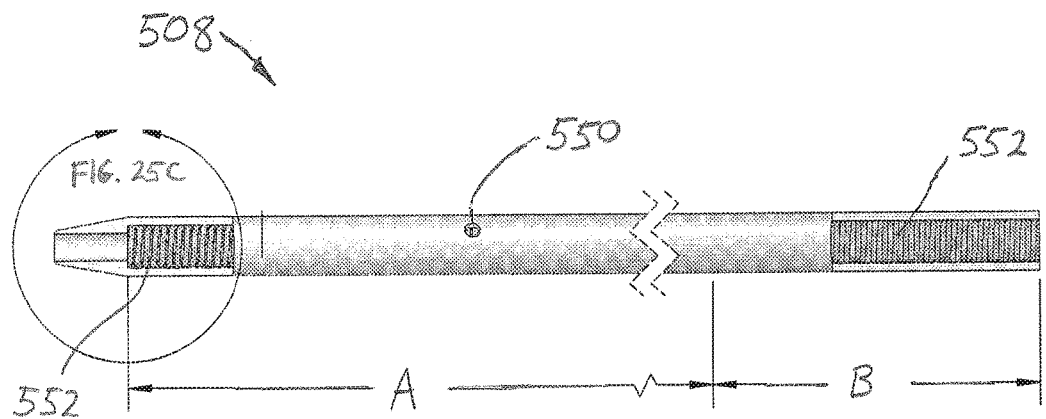
FIG. 25A is a fragmentary top view in partial cross-section showing the cannula of the infusion system of FIG. 11.
Figure 25B:
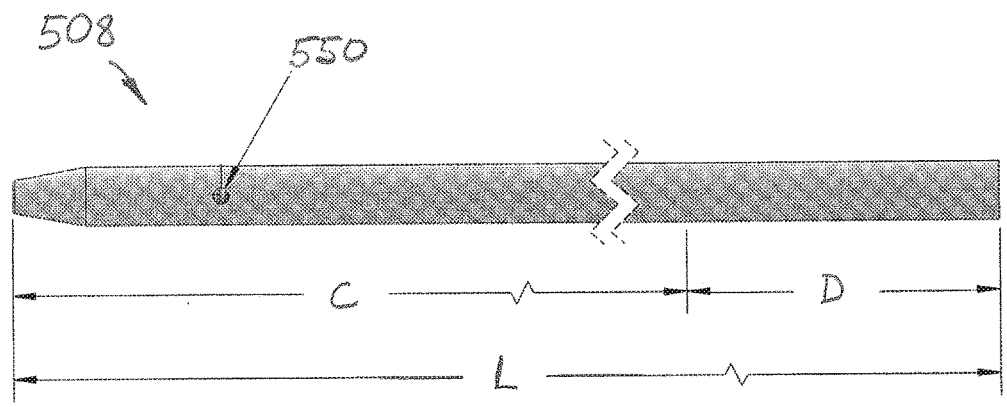
FIG. 25B is a fragmentary side view of the cannula shown in FIG. 25A.
Figure 25C:
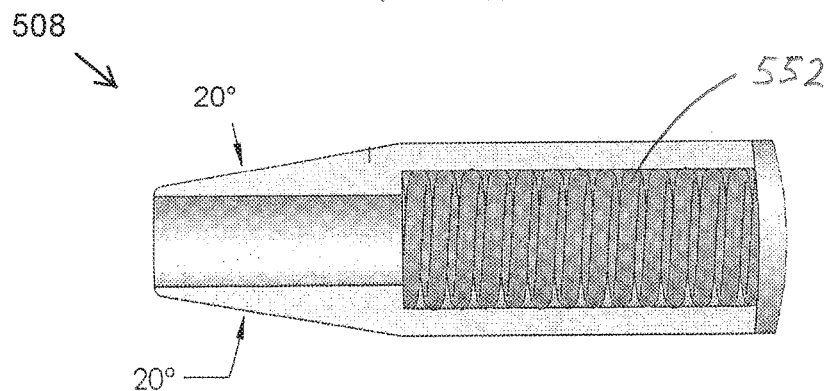
FIG. 25C is an enlarged view of the distal tip of the cannula shown in FIG. 25A.

Referring to FIGS. 25A-25C, various views are provided showing details of exemplary cannula 508 constructed according to aspects of the disclosure. Applicants have found that the unique combination of specific cannula and stylet features disclosed herein provide a soft, kink-resistant cannula for increased user comfort, and one that is reliably self-inserted (i.e. inserted without a needle over the cannula) without collapsing, buckling or crushing. While this cannula and stylet design is described in relation to helical inserter infusion system 400 disclosed above, it should be noted that it may also find useful application in non-helical self-insertion infusion systems, and may be introduced through the skin at any angle from 90 degrees to close to 0 degrees.

In the exemplary embodiment disclosed herein, cannula 508 is formed from a polyether block amide (PEBA) thermoplastic elastomer, such as a PEBA sold under the tradename of Pebax® by Arkema Inc. headquartered in King of Prussia, Pa. Applicants have found that using a Pebax® material having a durometer of 72 D, in combination with other features disclosed herein, provides greatly improved cannula performance over lower durometers such as 63 D. In this embodiment, cannula 508 has a length L of 24.8 mm and an outside diameter of 0.56 mm. Except for a short region at the distal tip of cannula 508 (as shown in FIG. 25C), the inside diameter of the cannula is 0.41 mm. A section extending proximally 0.71 mm from the distal tip of cannula 508 has an inside diameter of 0.26 mm, and a conical taper having an included angle of 20 degrees, as shown in FIG. 25C, A radius of 0.03 mm may be applied to the leading distal edge of the taper. Thus, cannula 508 is open at both ends with a single axial lumen extending between the openings. In other embodiments, the nominal conical taper angle may be between about 10 and about 30 degrees.

In this exemplary embodiment, three holes 550 are formed in cannula 508, each through one wall of the Pebax® only and having a diameter of 0.15 mm. Holes 550 may be placed 2 mm apart from each other and no more than 2 mm from the distal tip of cannula 508. The three holes 550 may be placed evenly around the circumference of cannula 508 such that they are 120 degrees apart. With this axial and circumferential spacing, holes 550 form a helical pattern. In other embodiments (not shown), fewer, more or no holes may be provided, they may have a different diameter or diameters, and various alternative spacing patterns may be used.

As depicted in FIGS. 25A and 25C, a helical coil 552 may be placed inside the central lumen of cannula 508 such that it extends from the proximal end of the cannula up to within 0.71 mm from the distal tip where the cannula has a reduced inside diameter. In this exemplary embodiment, coil 552 is formed from stainless steel 304 wire, and the wire has a diameter of 0.05 mm. Coil 552 is formed to have an outside diameter of 0.41 mm to match the inside diameter of cannula 508, and has an inside diameter of 0.30 mm to match the outside diameter of stylet 506 (shown in FIG. 26.) As shown in FIG. 25A, the length of coil 552 may be divided into two regions A and B, with region A having an axial length of 14 mm (not drawn to scale.) In region A, coil 552 is provided with a pitch of 0.075 mm such that there is a gap of 0.025 mm between adjacent turns of the coil. In region B, coil 552 is provided with a closed pitch equal to the wire diameter (0.05 mm) such that there are no gaps between adjacent turns of the coil. This arrangement allows cannula 508 to have sufficient strength for insertion while remaining highly flexible for user comfort. The open pitch in region A also permits increased fluid flow from the central lumen of cannula 508 laterally outward through holes 550. In other embodiments, the gap between adjacent turns of the coil in distal region A is between about 25% and about 100% of the coil wire diameter. In this exemplary embodiment, coil 552 is wound in a right-hand direction (although shown in the figures as if it were wound in a left-hand direction.)

Referring to FIG. 25B, the length of cannula 508 may be divided into regions C and D, with region D having an axial length of 5 mm (not drawn to scale relative to regions A and B in FIG. 25A or other dimensions.) In this exemplary embodiment, only region C is siliconized to reduce the force needed to insert cannula 508 through the skin of the user. Region D remains inside the base assembly and should not be siliconized. Region C may be siliconized with a silicon dispersion such as MED-4162 sold by NuSil Technology LLC in Carpinteria, Calif. The silicon may be diluted by mixing one part MED-4162 with four parts xylene. After the mixture is applied, it may be heat cured at 260 degrees F.

Figure 26A:
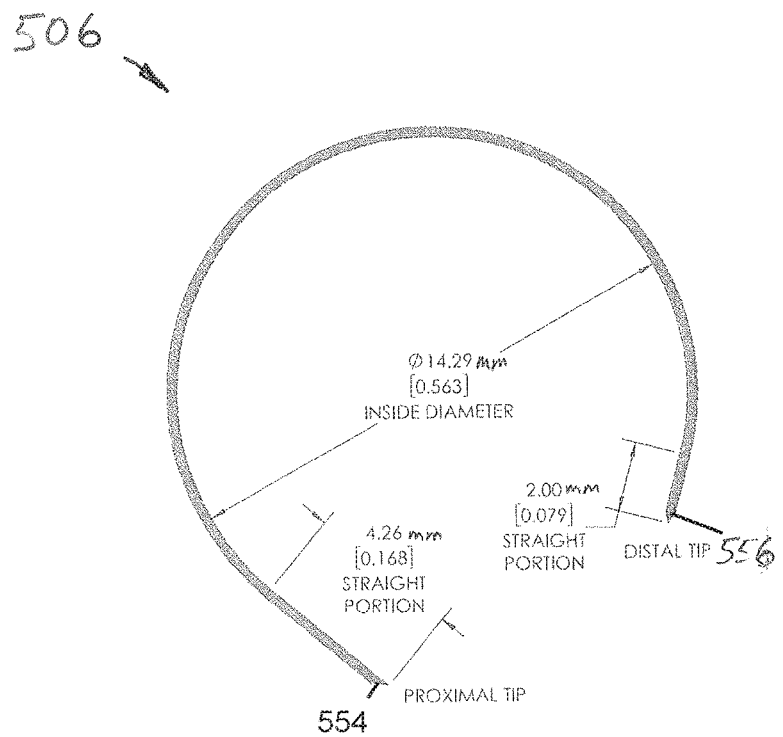
FIG. 26A is a top plan view showing the stylet of the infusion system of FIG. 11.
Figure 26B:
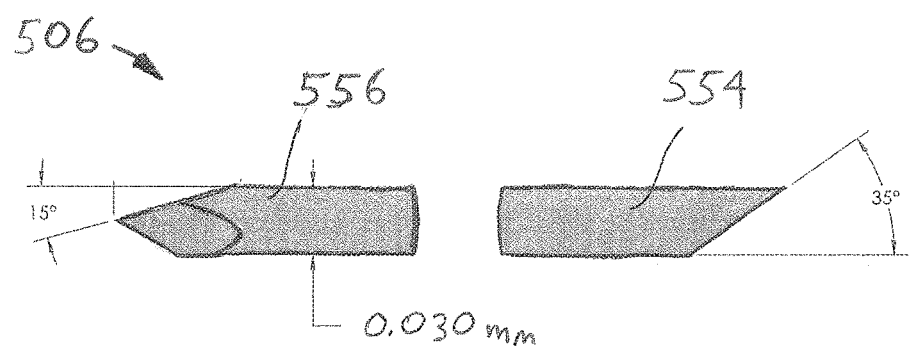
FIG. 26B is a fragmentary side view showing the distal and proximal ends of the stylet shown in FIG. 26A.

Referring to FIGS. 26A and 26B, details of stylet 506 are shown. In this exemplary embodiment, stylet 506 is formed from full hard stainless steel 304 wire having a wire diameter of 0.030 mm. Stylet 506 has an overall axial length of 37.40 mm when in a straight state. The majority of stylet 506 is formed into a curve having an inside diameter of 14.29 mm, as shown in FIG. 26A. A straight portion 4.26 mm long is left at the proximal end 554, and a straight portion 2.00 mm long is left at the distal end 556. As shown in FIG. 26B, a 35 degree bevel is provided on the proximal end 554 of stylet 506, and a 15 degree trocar tip is provided on the distal end 556. The trocar tip has three beveled faces rotated 120 degrees apart from one another around the circumference of the distal tip, with each face having a 15 degree angle and extending proximally 0.57 mm from the distal tip. In other embodiments, the angle of the trocar faces may be larger or smaller than 15 degrees, but it should be less than the desired insertion angle relative to the skin to allow the tip to penetrate the skin. In this exemplary embodiment, the desired insertion angle is 30 degrees.

Figure 26C:
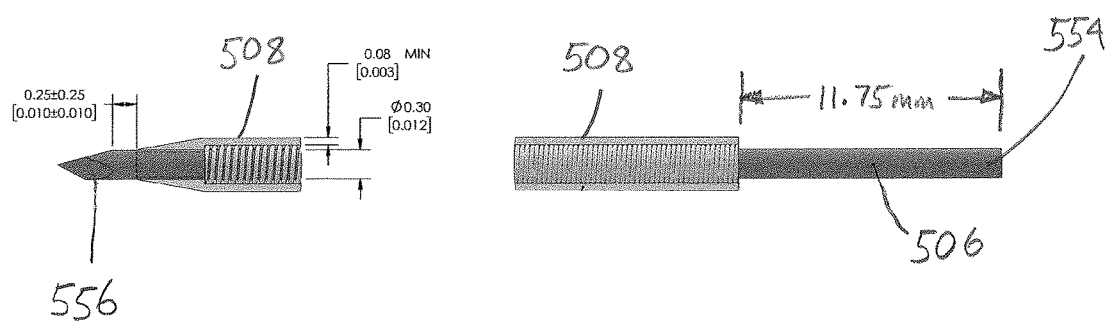
FIG. 26C is a fragmentary side view showing the distal and proximal ends of the cannula shown in FIGS. 25A-25C assembled with the stylet shown in FIGS. 26A and 26B.

Referring to FIG. 26C, cannula 508 is shown assembled over stylet 506. In use, the distal end 556 of stylet 506 protrudes from the distal end of cannula 508 a distance of 0.25 mm (measured from the unsharpened portion rather than the sharp tip), as shown. The proximal end 554 of stylet 506 extends from the proximal end of cannula 508 a distance of 11.75 mm from the beveled tip, as shown.

Figure 27A:
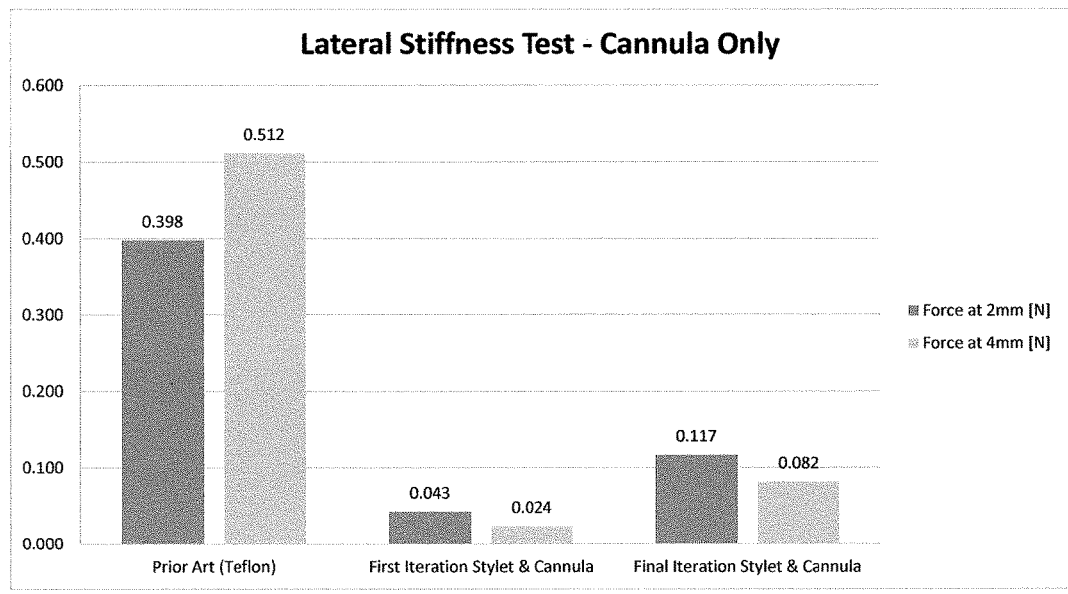
FIGS. 27A and 27B are graphs showing results of lateral stiffness tests performed on the cannula of FIGS. 25A-25C and the cannula and stylet assembly of FIG. 26C, respectively.
Figure 27B:
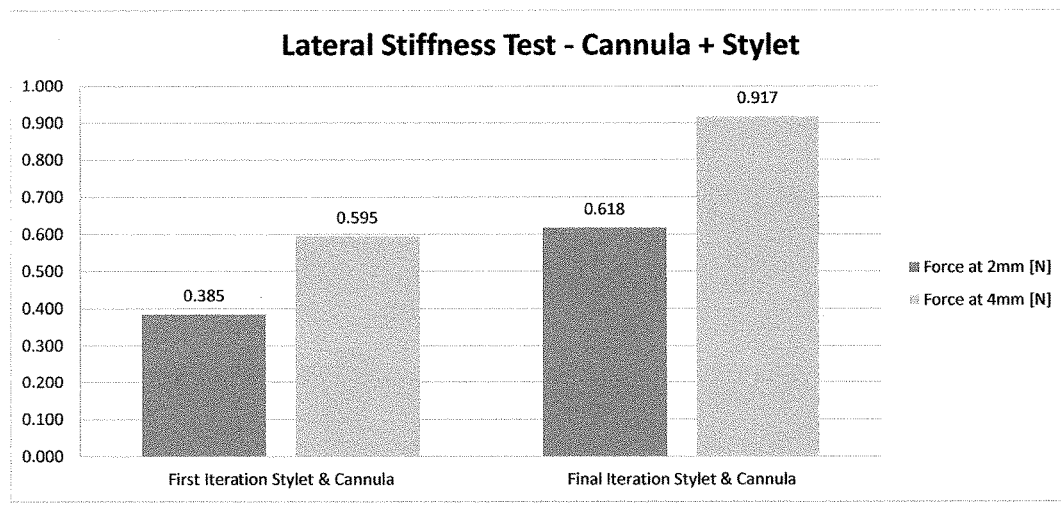

Referring to FIGS. 27A and 27B, graphs showing lateral stiffness test results for cannula 508 and stylet 506 are provided. The graphs compare the test results for cannula 508 and stylet 506 to a previous design version developed by the present applicants, and to commercially available prior art insulin infusion cannulas made of Teflon™. During the testing, the cannulas were held 10 mm from their distal tips while a test force was applied laterally at 5 mm from the tip. The lateral forces, measured in Newtons, required to deflect the distal tip 2 mm and 4 mm were recorded. FIG. 27A shows the test results for the cannulas only, while FIG. 27B shows the test results when stylets were present inside the cannulas. (The prior art cannulas were not tested with stylets.)

Figure 28A:
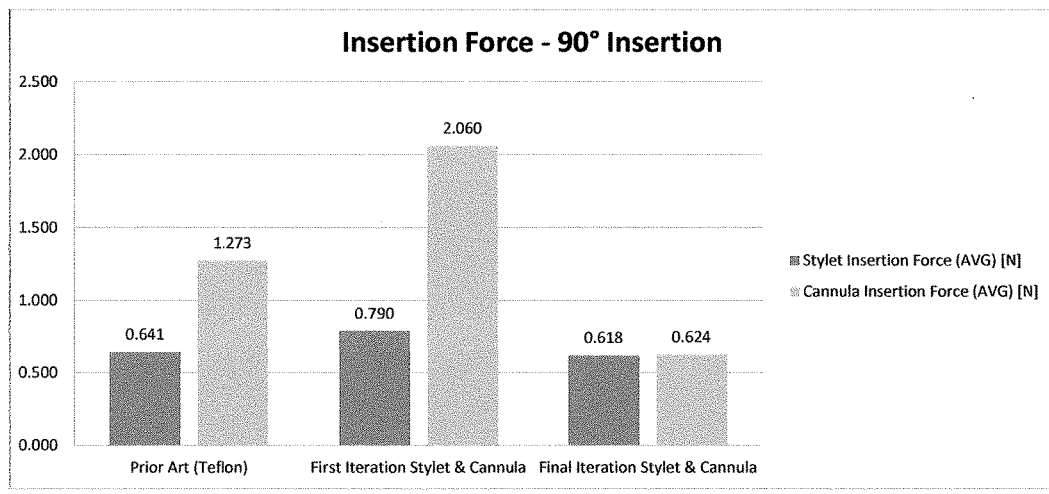
FIGS. 28A and 28B are graphs showing results of insertion force tests performed on the cannula and stylet assembly of FIG. 26C.
Figure 28B:
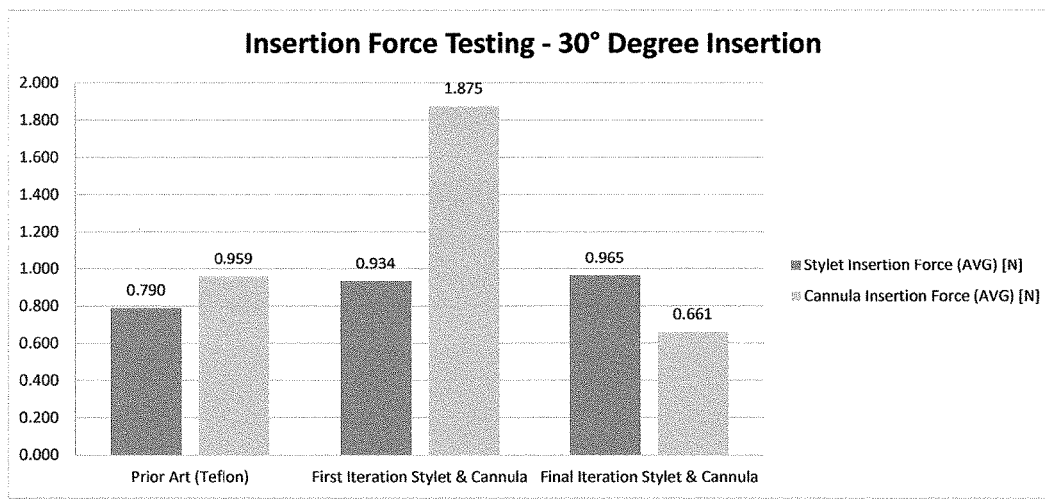

Referring to FIGS. 28A and 28B, graphs showing axial insertion forces for cannula 508 and stylet 506 are provided. The graphs compare the test results for cannula 508 and stylet 506 to the previous design version developed by the present applicants, and to commercially available prior art insulin infusion cannulas made of Teflon™. For FIG. 28A, the tests were conducted at a 90 degree insertion angle (i.e. the stylet and cannula were inserted perpendicular to the skin). For FIG. 28B, the tests were conducted at a 30 degree insertion angle (i.e. the stylet and cannula were inserted 30 degrees above being parallel to the skin).

In order to achieve the favorable results shown in FIGS. 27A-28B for the final iterations of cannula 508 and stylet 506, many countervailing parameters needed to be added or changed relative to the prior art and first iteration designs.

Figure 29A:
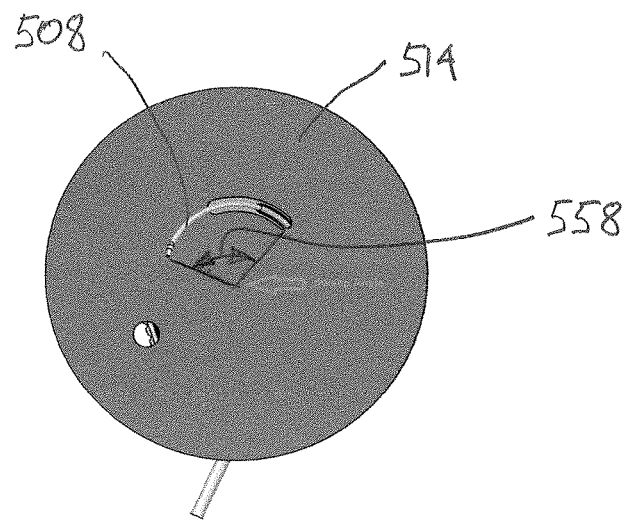
FIG. 29A is a bottom view showing the base assembly of the infusion system of FIG. 11.
Figure 29B:
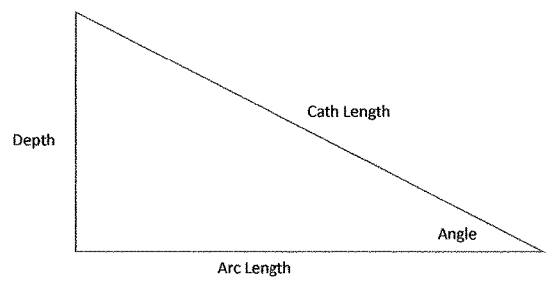
FIG. 29B is a table and diagram showing the trigonometric relationships between parameters of the cannula of the infusion system of FIG. 11.

Referring to FIGS. 29A and 29B, trigonometric parameters for the helical insertion of cannula 508 are provided. FIG. 29A depicts cannula 508 extending in a helical fashion from the bottom of base 514. A sweep angle 558 as shown is formed between the distal tip of cannula 508 and the point where it passes through the outer surface of the skin. FIG. 29B shows the trigonometric relationship between the angle that cannula 508 makes with the surface of the skin, the cannula length under the skin, the depth of the distal tip of the cannula beneath the skin, and the two-dimensional arc length that the cannula projects onto the surface of the skin.

In some embodiments, it is desirable to insert cannula 508 into the skin such that its distal tip resides between 4 and 9 mm below the surface (measured perpendicularly from the surface of the skin.) Because of the slenderness and softness of cannula 508 and stylet 506, and the varying densities of tissue anatomies below the skin, the cannula and stylet are not likely to travel in a perfectly helical path. The exemplary infusion system 400 disclosed herein is designed to insert a 14 mm length of cannula 508 at an angle of 30 degrees below the skin with a nominal helical radius of 7.15 mm such that the distal tip resides 7 mm below the surface, as shown in the middle line of the table in FIG. 29B. The other two lines of the table show the calculated insertion angles and other parameters that may occur when the distal tip instead goes either 4 or 9 mm deep. While the disclosed system 400 is designed to insert the cannula in a nominally helical path, it should be noted that the actual path that the cannula takes may vary. In other embodiments, the disclosed design may be modified (without necessarily departing from the scope of the claims) such that the nominal intended cannula path is partially or entirely spiral (i.e. changing in radius), curved (in two and or three dimensions), helical, straight, have other geometric trajectories, or combinations of the foregoing.

The systems described herein can advantageously allow transcutaneous placement of a soft cannula safely and automatically. The systems advantageously also do not require the disposal of a sharp, contaminated needle, since the stylet can be fully retracted back into the housing. The systems described herein are designed to be single use disposable units, but in other embodiments portions of the system such as the inserter may be made to be multi-use.

The disclosed infusion devices can be used, for example, for insulin delivery and thus may help to reduce the burden of managing diabetes by: (1) extending the wear duration from three to seven or more days, matching insulin pump cartridge and CGM sensor lifetime, (2) preserving infusion sites by minimizing tissue trauma, scar formation and lipodystrophy, (3) reducing the frequency of set failure and unexpected hyperglycemia, (4) providing more predictable insulin response by enhancing absorption, and/or (5) improving blood glucose control with a lower incidence of hypoglycemia.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the FIGS. is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" or "disclosure" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for delivering fluid to a user transcutaneously, the system comprising:
    a base assembly configured to be located on the user's skin;
    a flexible subcutaneous infusion cannula configured to be wound fully within the base assembly prior to insertion;
    an inserter assembly coupled to the base assembly, the inserter assembly being configured to drive the wound flexible subcutaneous infusion cannula from the base assembly through the user's skin at an angle of less than 45° in a nominally helical trajectory; and
    a fluid connection assembly configured to fluidically connect the base assembly to a source of delivery fluid.

2. The system of claim 1, wherein the inserter assembly is removably coupled to the base assembly.

3. The system of claim 1, further comprising a sharp inner stylet configured to extend through the flexible subcutaneous infusion cannula.

4. The system of claim 3, wherein the sharp inner stylet has a pre-set curved shape.

5. The system of claim 3, wherein the inserter assembly includes an automatic retraction mechanism configured to move the sharp inner stylet from an advanced position to a retracted position after completion of a cannula insertion cycle.

6. The system of claim 5, wherein the inserter assembly includes an automatic release mechanism configured to decouple the inserter assembly from the base assembly after completion of a stylet retraction cycle.

7. The system of claim 6, wherein the inserter assembly is configured to automatically perform the cannula insertion cycle, the stylet retraction cycle and a release cycle in succession after a single trigger event without further interaction from the user.

8. The system of claim 7, wherein the inserter assembly includes a single drive spring configured to supply all energy required to drive the cannula insertion cycle, the stylet retraction cycle and the release cycle.

9. The system of claim 1, wherein the base assembly includes an adhesive on at least one surface thereof configured to attach the base assembly to the user's skin.

10. The system of claim 1, wherein the flexible subcutaneous infusion cannula includes an outer tube and an inner reinforcement coil.

11. The system of claim 1, wherein the flexible subcutaneous infusion cannula includes two or more fluid exit holes at or near the distal end thereof.

12. The system of claim 1, wherein the system further comprises packaging for enclosing at least the inserter assembly before use, the packaging including a rotational element, wherein the inserter assembly includes at least one torsion drive spring, and wherein the inserter assembly is configured to automatically charge the drive spring as the rotational element is rotated to open the packaging.

13. The system of claim 1, wherein the fluid connection assembly includes tubing and an element or assembly that changes color when the tubing has been primed with fluid.

14. The system of claim 1, wherein the fluid connection assembly includes a releasable fluid interconnect assembly configured to releasably connect the base assembly to the source of delivery fluid, and wherein the source of delivery fluid is external to the base assembly.

15. The system of claim 14, wherein the releasable fluid interconnect assembly includes a needle and a septum, wherein the fluid interconnect assembly is configured to insert an end of the needle through the septum after a cannula stylet is withdrawn from the septum.

* * * * *